(12) United States Patent
Rosati et al.

(10) Patent No.: US 10,195,091 B2
(45) Date of Patent: Feb. 5, 2019

(54) COMPOSITIONED, TEXTURED NONWOVEN WEBS

(71) Applicant: The Procter & Gamble Company, Cincinnati, OH (US)

(72) Inventors: Rodrigo Rosati, Frankfurt am Main (DE); Jill Orr, Liberty Township, OH (US); John Lee Hammons, Hamilton, OH (US); John Brian Strube, Okeana, OH (US); Shirdish Poondru, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/453,981

(22) Filed: Mar. 9, 2017

(65) Prior Publication Data

US 2017/0258650 A1    Sep. 14, 2017

Related U.S. Application Data

(60) Provisional application No. 62/306,730, filed on Mar. 11, 2016.

(51) Int. Cl.
*A61F 13/511* (2006.01)
*D04H 1/4374* (2012.01)
(Continued)

(52) U.S. Cl.
CPC ...... *A61F 13/51121* (2013.01); *A61F 13/511* (2013.01); *A61F 13/512* (2013.01); *A61F 13/51104* (2013.01); *A61F 13/51305* (2013.01); *A61F 13/537* (2013.01); *B32B 5/26* (2013.01); *D04H 1/42* (2013.01); *D04H 1/4374* (2013.01);
(Continued)

(58) Field of Classification Search
CPC ......... A61F 13/51121; A61F 13/51104; A61F 13/511; A61F 13/5116; A61F 2013/51165; A61F 2013/5103; D04H 1/42; D04H 1/4374; D04H 11/08; B32B 3/00; B32B 3/28; B32B 3/30
See application file for complete search history.

(56) References Cited

U.S. PATENT DOCUMENTS 1,668,322 A    5/1928    Kessler, Jr.
1,867,314 A    7/1932    Gurwick
(Continued)

FOREIGN PATENT DOCUMENTS

DE    19854634 C1    2/2000
EP    0951889 A1    10/1999
(Continued)

OTHER PUBLICATIONS

U.S. Appl. No. 15/698,709, dated Sep. 8, 2017, Aviles, et al.
(Continued)

*Primary Examiner* — Catherine A. Simone
(74) *Attorney, Agent, or Firm* — George H. Leal

(57) ABSTRACT

Disclosed herein are textured nonwoven webs suitable for use in disposable absorbent articles. The textured nonwoven webs have a generally planar first region and a plurality of integrally formed discrete second regions. The textured nonwoven webs also have at least one composition disposed on at least one of the first region or the plurality of discrete second regions.

20 Claims, 44 Drawing Sheets

(51) Int. Cl.
*D04H 11/08* (2006.01)
*D04H 1/42* (2012.01)
*A61F 13/512* (2006.01)
*A61F 13/513* (2006.01)
*A61F 13/537* (2006.01)
*B32B 5/26* (2006.01)
*D04H 1/70* (2012.01)
*A61F 13/15* (2006.01)

(52) U.S. Cl.
CPC ............... *D04H 1/70* (2013.01); *D04H 11/08* (2013.01); *A61F 2013/15284* (2013.01)

(56) References Cited

U.S. PATENT DOCUMENTS

| | | |
|---|---|---|
| 2,226,163 A | 12/1940 | Dufour |
| 2,427,765 A | 9/1947 | Chollar |
| 2,468,400 A | 4/1949 | Huebner |
| 2,864,310 A | 12/1958 | Nelson |
| 3,055,296 A | 9/1962 | Farrow |
| 3,056,384 A | 10/1962 | Beale et al. |
| 3,265,500 A | 8/1966 | Lewis |
| 3,294,016 A | 12/1966 | Kessler et al. |
| 3,301,746 A | 1/1967 | Sanford et al. |
| 3,473,576 A | 10/1969 | Amneus |
| 3,573,164 A | 3/1971 | Friedberg et al. |
| 3,738,269 A | 6/1973 | Wagner |
| 3,759,261 A | 9/1973 | Wang |
| 3,821,068 A | 6/1974 | Shaw |
| 3,896,722 A | 7/1975 | Farrow |
| 3,896,723 A | 7/1975 | Farrow et al. |
| 3,974,025 A | 8/1976 | Ayers |
| 3,994,771 A | 11/1976 | Morgan, Jr. et al. |
| 4,033,258 A | 7/1977 | Farrow |
| 4,041,951 A | 8/1977 | Sanford |
| 4,098,630 A | 7/1978 | Morse |
| 4,191,609 A | 3/1980 | Trokhan |
| 4,191,756 A | 3/1980 | Masi et al. |
| 4,231,370 A | 11/1980 | Mroz et al. |
| 4,239,065 A | 12/1980 | Trokhan |
| 4,243,446 A | 1/1981 | Mathey |
| 4,275,105 A | 6/1981 | Boyd et al. |
| 4,300,981 A | 11/1981 | Carstens |
| 4,333,979 A | 6/1982 | Sciaraffa et al. |
| 4,355,066 A | 10/1982 | Newman |
| 4,361,089 A | 11/1982 | Wittkopf et al. |
| 4,437,408 A | 3/1984 | Arkans |
| 4,440,597 A | 4/1984 | Wells et al. |
| 4,452,141 A | 6/1984 | Mistyurik |
| 4,458,399 A | 7/1984 | Kessler |
| 4,483,053 A | 11/1984 | Hamisch, Jr. |
| 4,526,098 A | 7/1985 | Bachman |
| 4,528,239 A | 7/1985 | Trokhan |
| 4,529,480 A | 7/1985 | Trokhan |
| 4,534,094 A | 8/1985 | Kessler |
| 4,550,681 A | 11/1985 | Zimmer et al. |
| 4,574,732 A | 3/1986 | Verwey et al. |
| 4,599,627 A | 7/1986 | Vollert |
| 4,637,859 A | 1/1987 | Trokhan |
| 4,738,674 A | 4/1988 | Todd et al. |
| 4,766,840 A | 8/1988 | Beckley et al. |
| 4,812,899 A | 3/1989 | Kueppers |
| 4,844,952 A | 7/1989 | Korenkiewicz et al. |
| 4,846,821 A | 7/1989 | Lyons et al. |
| 4,878,977 A | 11/1989 | Kueppers |
| 4,909,879 A | 3/1990 | Ball |
| 4,939,992 A | 7/1990 | Bird |
| 5,082,703 A | 1/1992 | Longobardi |
| 5,161,829 A | 11/1992 | Detrick et al. |
| 5,282,419 A | 2/1994 | Barrois |
| 5,288,348 A | 2/1994 | Modrak |
| 5,316,582 A | 5/1994 | Dubel |
| 5,332,613 A | 7/1994 | Taylor et al. |
| 5,354,289 A | 10/1994 | Mitchell et al. |
| 5,364,504 A | 11/1994 | Smurkoski et al. |
| 5,417,789 A | 5/1995 | Lauritzen |
| 5,429,686 A | 7/1995 | Chiu et al. |
| 5,458,590 A | 10/1995 | Schleinz et al. |
| 5,470,640 A | 11/1995 | Modrak |
| 5,503,076 A | 4/1996 | Yeo |
| 5,529,664 A | 6/1996 | Trokhan et al. |
| 5,549,790 A | 8/1996 | Van Phan |
| 5,556,509 A | 9/1996 | Trokhan et al. |
| 5,580,423 A | 12/1996 | Ampulski et al. |
| 5,609,725 A | 3/1997 | Van Phan |
| 5,629,052 A | 5/1997 | Trokhan et al. |
| 5,637,194 A | 6/1997 | Ampulski et al. |
| 5,672,248 A | 9/1997 | Wendt et al. |
| 5,674,663 A | 10/1997 | McFarland et al. |
| 5,679,222 A | 10/1997 | Rasch et al. |
| 5,693,187 A | 12/1997 | Ampulski et al. |
| 5,695,855 A | 12/1997 | Yeo et al. |
| 5,705,011 A | 1/1998 | Bodford et al. |
| 5,709,775 A | 1/1998 | Trokhan et al. |
| 5,714,041 A | 2/1998 | Ayers et al. |
| 5,733,634 A | 3/1998 | Karel |
| 5,734,800 A | 3/1998 | Herbert et al. |
| 5,766,389 A | 6/1998 | Brandon et al. |
| 5,776,307 A | 7/1998 | Ampulski et al. |
| 5,785,697 A | 7/1998 | Trombetta et al. |
| 5,795,440 A | 8/1998 | Ampulski et al. |
| 5,814,190 A | 9/1998 | Van Phan |
| 5,817,377 A | 10/1998 | Trokhan et al. |
| 5,846,379 A | 12/1998 | Ampulski et al. |
| 5,855,739 A | 1/1999 | Ampulski et al. |
| 5,858,514 A | 1/1999 | Bowers |
| 5,861,082 A | 1/1999 | Ampulski et al. |
| 5,865,950 A | 2/1999 | Vinson et al. |
| 5,871,887 A | 2/1999 | Trokhan et al. |
| 5,897,745 A | 4/1999 | Ampulski et al. |
| 5,900,109 A | 5/1999 | Sanders et al. |
| 5,904,811 A | 5/1999 | Ampulski et al. |
| 5,906,161 A | 5/1999 | Kessler |
| 5,906,710 A | 5/1999 | Trokhan |
| 5,942,085 A | 8/1999 | Neal et al. |
| 5,972,477 A | 10/1999 | Kim et al. |
| 6,033,513 A | 3/2000 | Nakamura |
| 6,048,938 A | 4/2000 | Neal et al. |
| 6,096,412 A | 8/2000 | McFarland et al. |
| 6,127,595 A | 10/2000 | Makoui et al. |
| 6,173,646 B1 | 1/2001 | Tanaka et al. |
| 6,187,138 B1 | 2/2001 | Neal et al. |
| 6,234,078 B1 | 5/2001 | Kessler |
| 6,281,269 B1 | 8/2001 | Schut |
| 6,284,942 B1 | 9/2001 | Rabin |
| 6,307,119 B1 | 10/2001 | Cammarota et al. |
| 6,322,665 B1 | 11/2001 | Sun et al. |
| 6,330,857 B1 | 12/2001 | Maximovsky et al. |
| 6,403,857 B1 | 6/2002 | Gross et al. |
| 6,458,211 B1 | 10/2002 | Wefers et al. |
| 6,477,948 B1 | 11/2002 | Nissing et al. |
| 6,531,027 B1 | 3/2003 | Lender et al. |
| 6,572,575 B1 | 6/2003 | Shimada et al. |
| 6,610,131 B2 | 8/2003 | Harris et al. |
| 6,624,100 B1 | 9/2003 | Pike |
| 6,627,022 B2 | 9/2003 | Fusco |
| 6,651,560 B2 | 11/2003 | Neuhaus |
| 6,993,964 B2 | 2/2006 | Franz et al. |
| 7,306,699 B2 | 12/2007 | Urlaub et al. |
| 7,611,582 B2 | 11/2009 | McNeil et al. |
| 7,648,752 B2 * | 1/2010 | Hoying ............ A61F 13/15707 428/133 |
| 7,703,394 B2 | 4/2010 | Neuhaus |
| 7,736,688 B2 | 6/2010 | Oetjen et al. |
| 7,816,285 B2 | 10/2010 | MacDonald et al. |
| 8,012,297 B2 | 9/2011 | Baldauf |
| 8,153,226 B2 | 4/2012 | Curro et al. |
| 8,158,253 B2 | 4/2012 | Spinks |
| 8,163,132 B2 | 4/2012 | Kien |
| 8,691,041 B2 | 4/2014 | Oetjen |
| 8,943,957 B2 | 2/2015 | McNeil et al. |
| 8,945,334 B2 | 2/2015 | Detjen |
| 9,050,220 B2 | 6/2015 | Digiacomantonio et al. |

(56) References Cited

U.S. PATENT DOCUMENTS

| | | |
|---|---|---|
| 9,102,182 B2 | 8/2015 | McNeil et al. |
| 9,237,973 B2 | 1/2016 | Abuto et al. |
| 9,414,971 B2 | 8/2016 | Oetjen |
| 9,579,924 B2 | 2/2017 | Boegli |
| 9,610,200 B2 | 4/2017 | Oetjen |
| 9,642,752 B2 | 5/2017 | Oetjen |
| 9,707,133 B2 | 7/2017 | Digiacomantonio et al. |
| 2001/0044611 A1 | 11/2001 | Noda et al. |
| 2002/0002358 A1 | 1/2002 | Durrance et al. |
| 2002/0112832 A1 | 8/2002 | Burazin et al. |
| 2003/0065299 A1 | 4/2003 | Carlucci et al. |
| 2003/0114818 A1 | 6/2003 | Benecke et al. |
| 2003/0171729 A1 | 9/2003 | Kaun et al. |
| 2003/0194481 A1 | 10/2003 | Lippelt |
| 2004/0122386 A1 | 6/2004 | Mocadlo |
| 2004/0170813 A1 | 9/2004 | Digiacomantonio et al. |
| 2004/0176736 A1 | 9/2004 | Christon et al. |
| 2005/0281976 A1 | 12/2005 | Curro et al. |
| 2006/0008514 A1 | 1/2006 | Koenig et al. |
| 2007/0026209 A1 | 2/2007 | MacDonald et al. |
| 2007/0049153 A1 | 3/2007 | Dunbar et al. |
| 2008/0036196 A1 | 2/2008 | Steenblik et al. |
| 2008/0132872 A1 | 6/2008 | Trennepohl et al. |
| 2010/0036352 A1 | 2/2010 | Hood et al. |
| 2010/0126366 A1 | 5/2010 | Kasper et al. |
| 2010/0206221 A1 | 8/2010 | Branca et al. |
| 2010/0209664 A1 | 8/2010 | Sato et al. |
| 2010/0233438 A1 | 9/2010 | Stone et al. |
| 2010/0247844 A1* | 9/2010 | Curro .................. A61F 13/512 428/96 |
| 2011/0106035 A1 | 5/2011 | Arora et al. |
| 2011/0112499 A1 | 5/2011 | Trennepohl et al. |
| 2011/0302733 A1 | 12/2011 | Yuan |
| 2012/0222568 A1 | 9/2012 | Byrne et al. |
| 2014/0121621 A1* | 5/2014 | Kirby .................. A61F 13/5126 604/374 |
| 2014/0234575 A1 | 8/2014 | Mitsuno et al. |
| 2014/0296814 A1 | 10/2014 | Gray et al. |
| 2015/0173964 A1 | 6/2015 | Coe et al. |
| 2015/0250662 A1 | 9/2015 | Isele et al. |
| 2015/0343480 A1 | 12/2015 | Byrne et al. |
| 2016/0067118 A1 | 3/2016 | Hammons et al. |
| 2016/0074251 A1 | 3/2016 | Strube et al. |
| 2016/0074252 A1 | 3/2016 | Strube et al. |
| 2016/0074253 A1 | 3/2016 | Strube et al. |
| 2016/0074254 A1 | 3/2016 | Orr et al. |
| 2016/0074255 A1 | 3/2016 | Strube et al. |
| 2016/0074256 A1 | 3/2016 | Strube et al. |
| 2016/0075122 A1 | 3/2016 | Strube et al. |
| 2016/0075123 A1 | 3/2016 | Strube et al. |
| 2016/0076180 A1 | 3/2016 | Strube et al. |
| 2016/0076181 A1 | 3/2016 | Strube et al. |
| 2016/0076182 A1 | 3/2016 | Strube et al. |
| 2016/0076184 A1 | 3/2016 | Orr et al. |
| 2016/0331596 A1 | 11/2016 | Oetjen |
| 2017/0120260 A1 | 5/2017 | Oetjen |
| 2017/0210110 A1 | 7/2017 | Oetjen |
| 2017/0225449 A1 | 8/2017 | Aviles et al. |
| 2017/0258650 A1 | 9/2017 | Rosati et al. |
| 2017/0259524 A1 | 9/2017 | Neton et al. |
| 2017/0259550 A1 | 9/2017 | Neton et al. |
| 2018/0071151 A1 | 3/2018 | Aviles et al. |

FOREIGN PATENT DOCUMENTS

| | | |
|---|---|---|
| EP | 1338262 A1 | 8/2003 |
| EP | 1527898 A1 | 5/2005 |
| EP | 1075948 B1 | 11/2005 |
| EP | 1673225 B1 | 8/2008 |
| GB | 1176321 | 1/1970 |
| GB | 1241793 | 8/1971 |
| GB | 1241794 | 8/1971 |
| GB | 1350059 | 4/1974 |
| GB | 1396282 | 6/1975 |
| GB | 1439458 | 6/1976 |
| GB | 1468360 | 3/1977 |
| GB | 1570545 | 7/1980 |
| GB | 2314292 A1 | 12/1997 |
| WO | WO8400516 A1 | 2/1984 |
| WO | WO9954143 A1 | 10/1999 |
| WO | WO03020835 A1 | 3/2003 |
| WO | WO2007070132 A1 | 6/2007 |
| WO | WO2008103650 A2 | 8/2008 |
| WO | WO2010071543 A1 | 6/2010 |
| WO | WO2012176656 A1 | 12/2012 |

OTHER PUBLICATIONS

Search Report and Written Opinion for PCT/US2017/016324 dated May 30, 2017.

International Search Report for PCT/US2017/021485 dated May 18, 2017.

Hatch, Kathryn, "Nonwoven Fabrics Structures", Textile Science, 1993, p. 363.

Search Report and Written Opinion for PCT/US2017/050603 dated Nov. 7, 2017.

All Office Actions for U.S. Appl. No. 15/674,563, filed Feb. 3, 2017.

All Office Actions for U.S. Appl. No. 15/698,709, filed Sep. 8, 2017.

\* cited by examiner

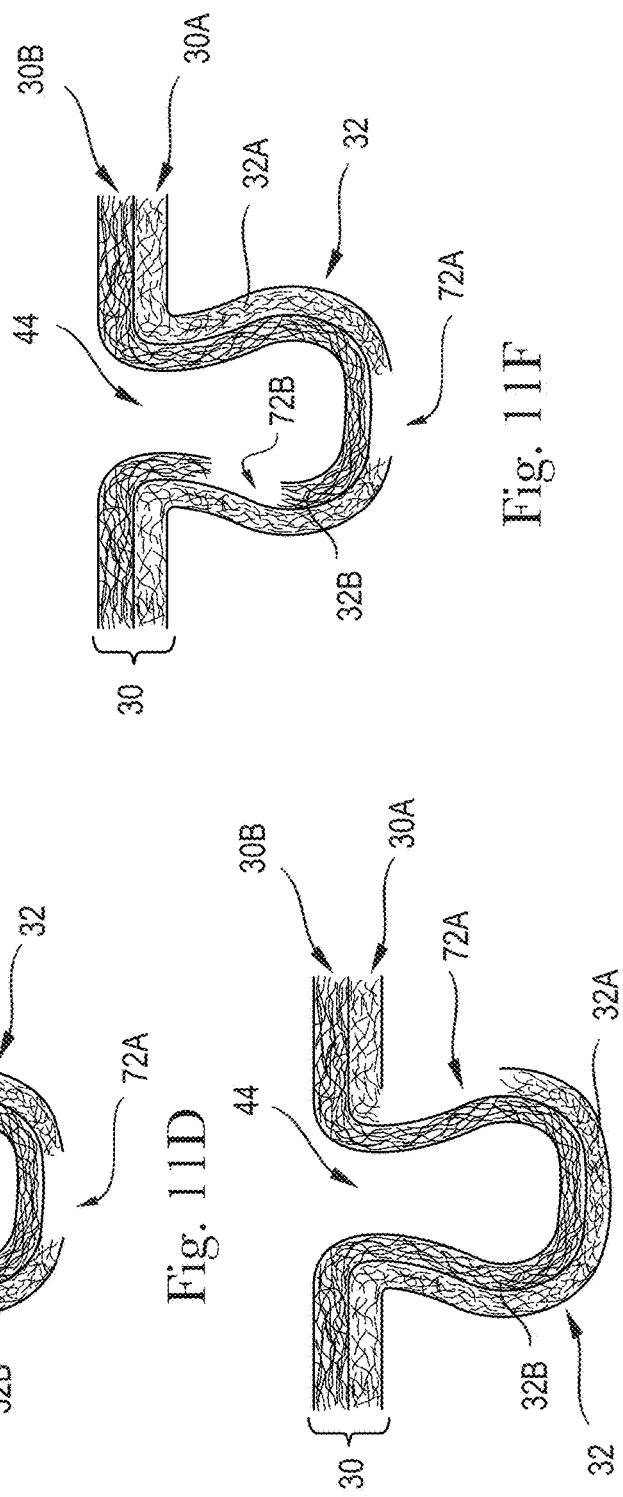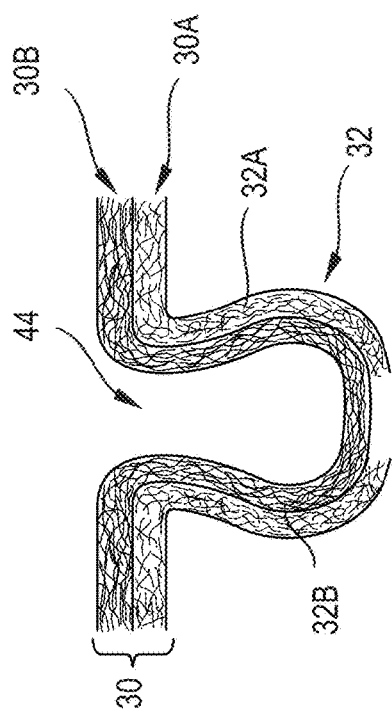

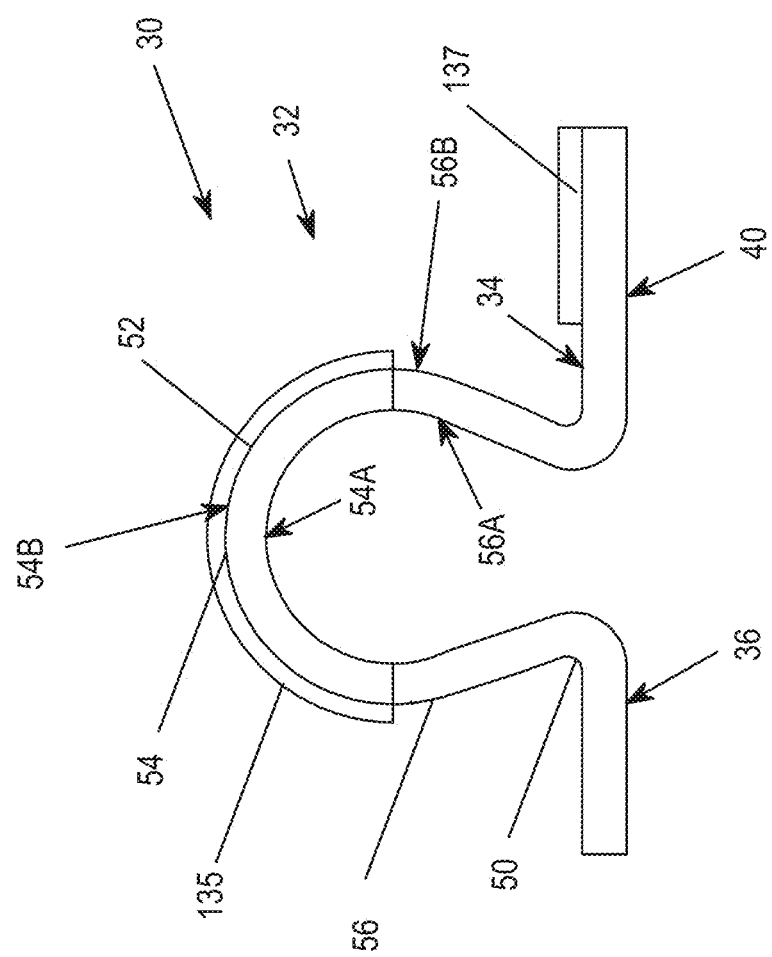
Fig. 18A
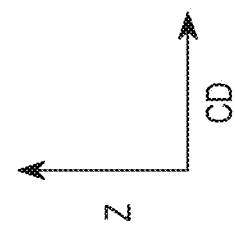

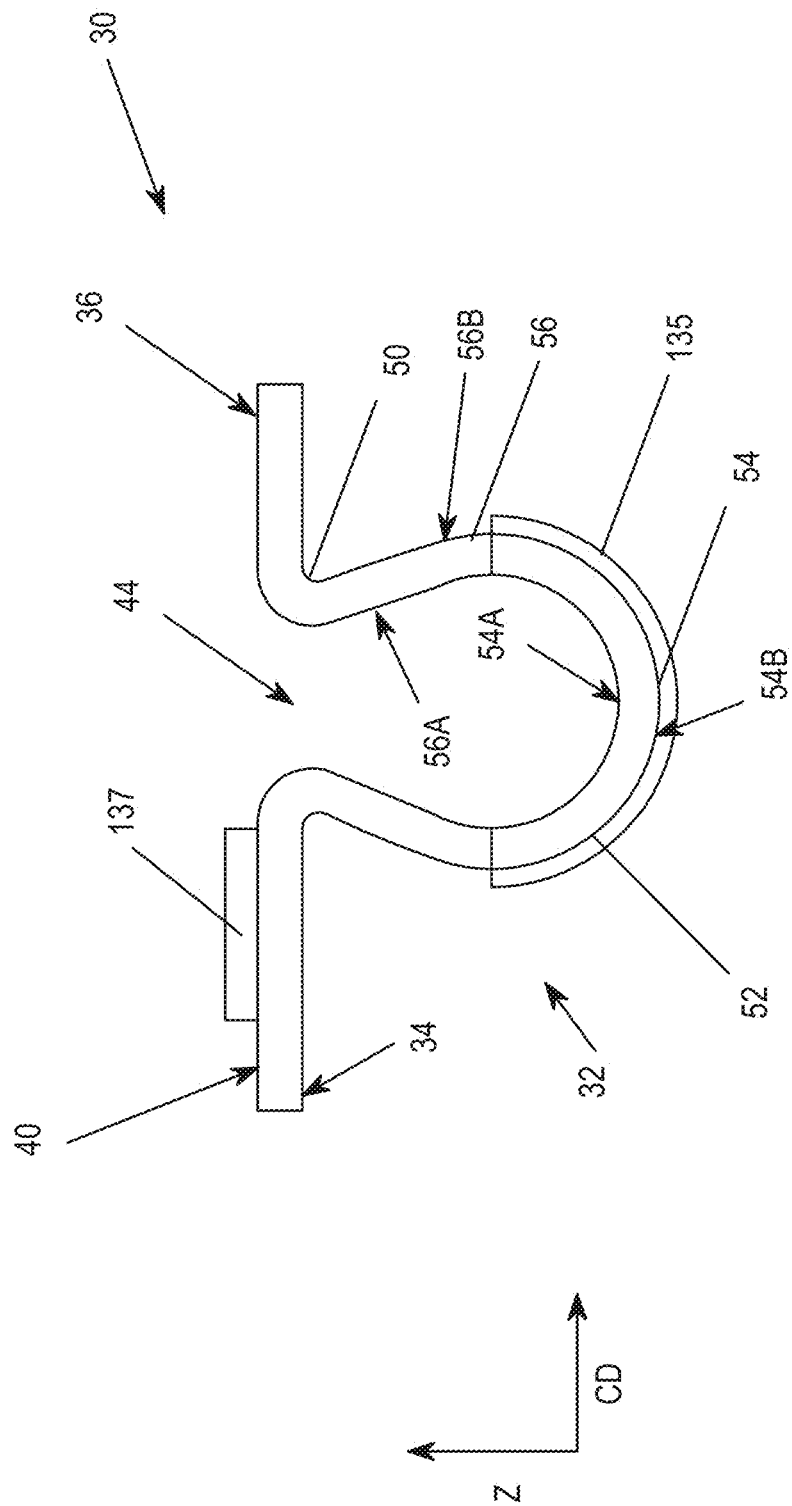

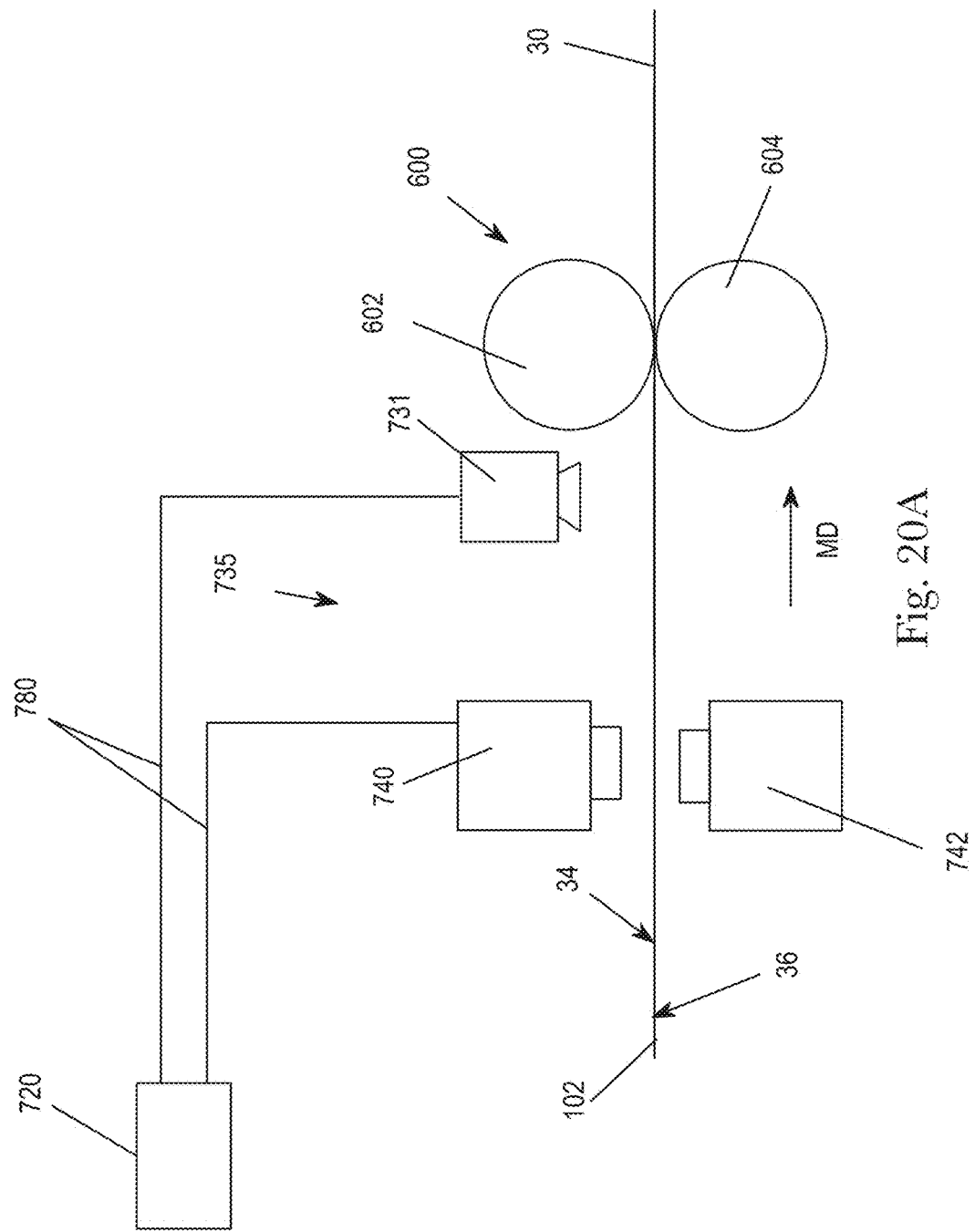

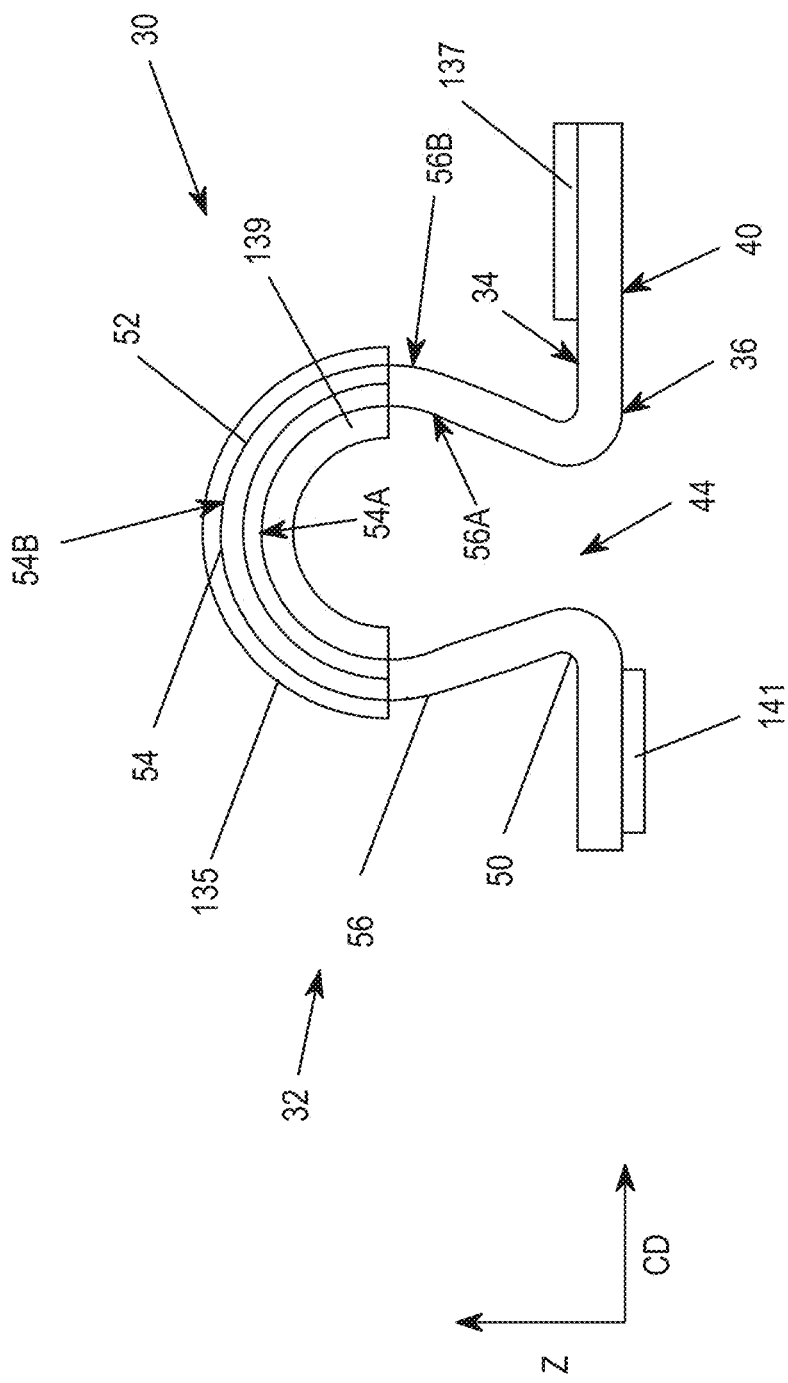

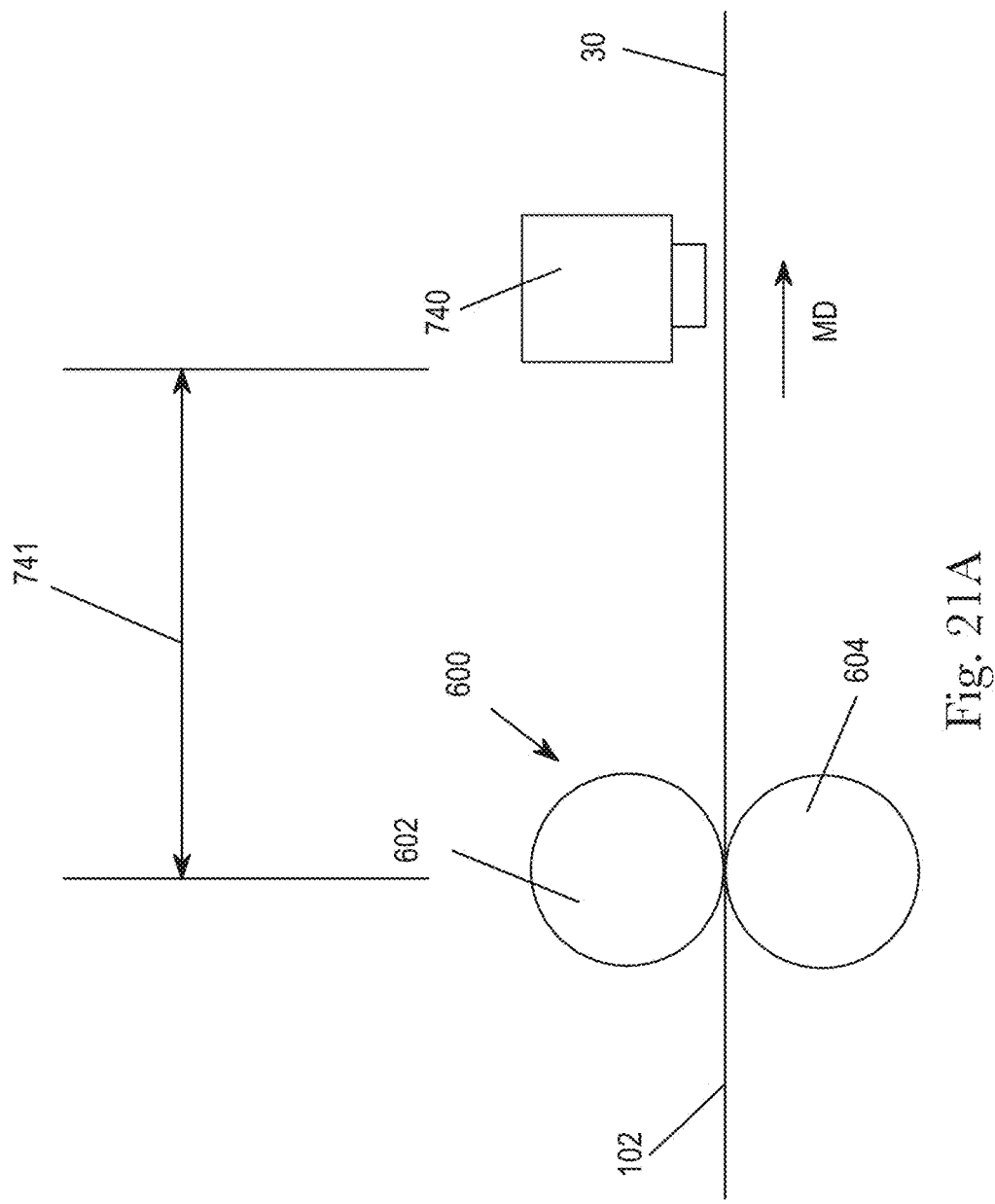

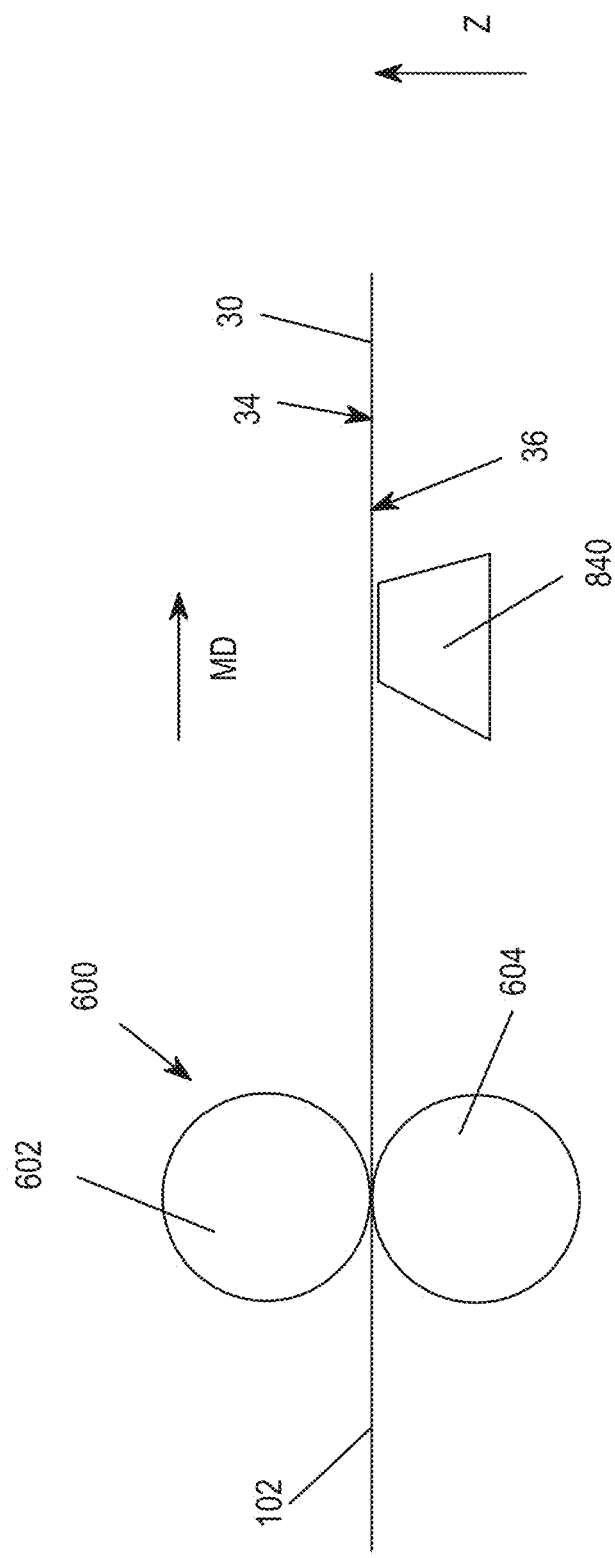

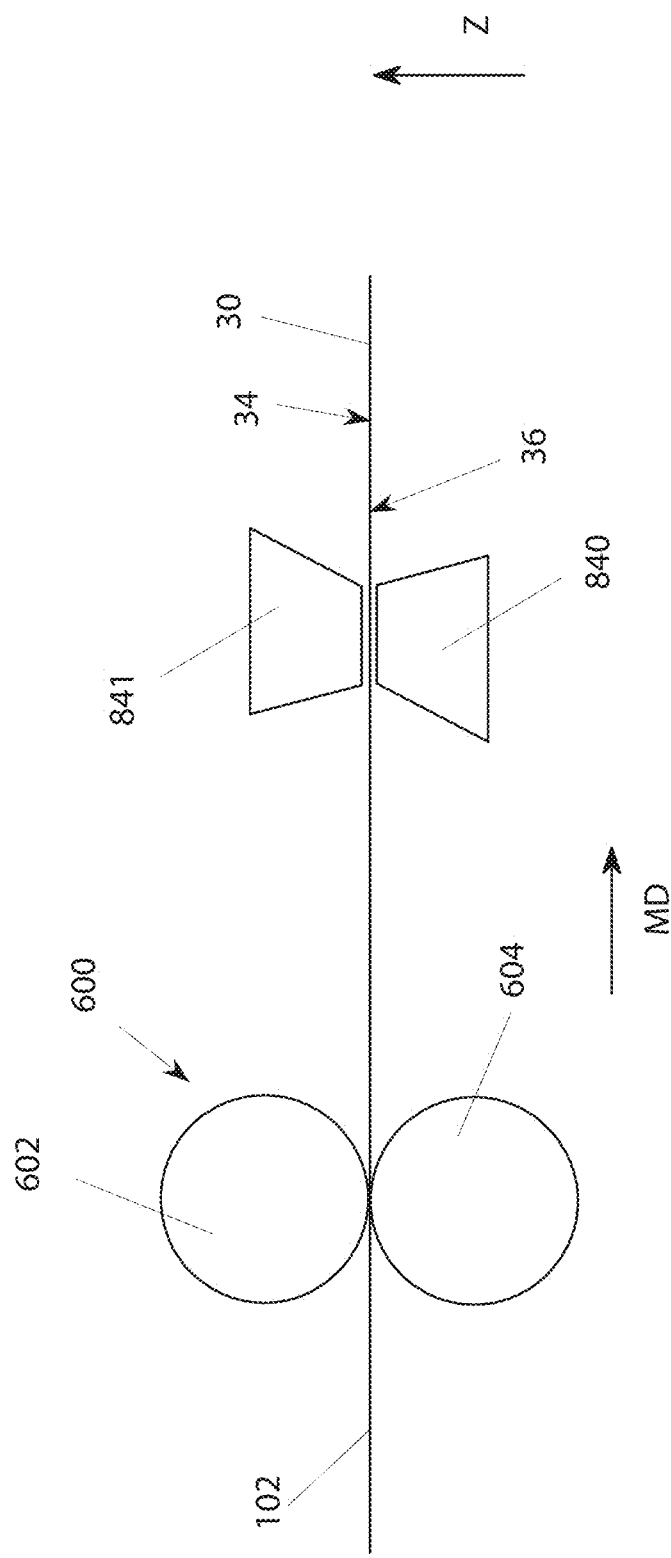

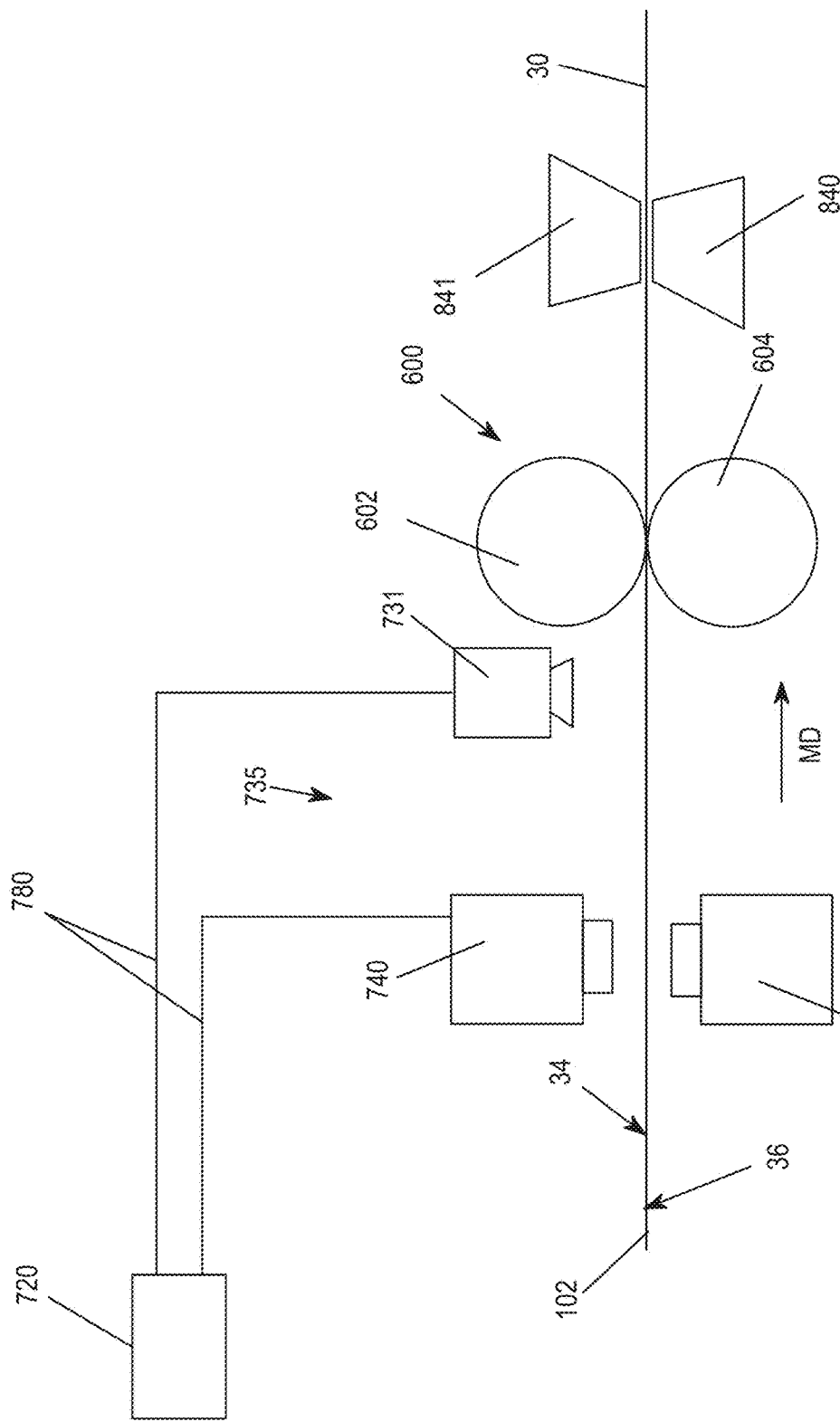

COMPOSITIONED, TEXTURED NONWOVEN WEBS

FIELD OF THE INVENTION

The present invention pertains to the textured nonwoven webs comprising a composition and disposable absorbent articles incorporating the same.

BACKGROUND OF THE INVENTION

Nonwoven webs have been used in a myriad of disposable absorbent articles over the past several years. In some particular absorbent articles, e.g. diapers and feminine hygiene pads, nonwovens may be utilized as a topsheet, backsheet, or some other feature of these particular absorbent articles.

The requirements for absorbent articles may be disparate depending on use. For example, a nonwoven web used as a topsheet for baby diapers may not be suitable for adult incontinence products. Similarly, a nonwoven web suitable as a topsheet for adult incontinence products may not be suitable for feminine hygiene pads.

Additionally, requirements for nonwoven webs in disposable absorbent articles may vary by geography. For example, in one geography an absorbent article with a soft topsheet may be a factor which is foremost in consumer's minds. In another geography, absorbent articles which minimize the amount of rewet may be foremost in consumer's minds. In yet another geography, the speed of acquisition of liquid insults may be foremost in consumer's minds.

It would be beneficial for a nonwoven web to address one or more of the above concerns. It would also be beneficial to have a process which facilitated the production of nonwoven webs capable of addressing one or more of the above concerns.

SUMMARY OF THE INVENTION

Disclosed herein are textured nonwoven webs which can be used in disposable absorbent articles. Some exemplary uses include topsheet, acquisition layer or overwrap for a tampon. The textured nonwoven webs of the present invention, when utilized for example as a topsheet of a disposable absorbent article, can provide a soft feel to the user and can provide quick acquisition of menstrual and/or urine insults. Additionally, as discussed herein, the textured nonwoven webs may be configured in a myriad of ways to increase the soft feel, acquisition, and/or reduce rewet. Additionally, the textured nonwoven webs of the present invention comprise a composition which can be provided to the textured nonwoven webs in a number of regions of the web to enhance the properties of an absorbent article described above. Other benefits and configurations in the textured nonwoven webs and other disposable absorbent articles are discussed hereinafter.

BRIEF DESCRIPTION OF THE DRAWINGS

FIG. 11D is a cross-sectional view taken along the transverse axis of a deformation of an alternative embodiment of a multi-layer nonwoven web shown with the base opening facing upward.

FIG. 11E is a cross-sectional view taken along the transverse axis of a deformation of an alternative embodiment of a multi-layer nonwoven web shown with the base opening facing upward.

FIG. 11F is a cross-sectional view taken along the transverse axis of a deformation of an alternative embodiment of a multi-layer nonwoven web shown with the base opening facing upward.

FIG. 18A is a schematic cross sectional view of an exemplary textured nonwoven web in accordance with the present disclosure comprising a composition site.

FIG. 18B is a schematic cross sectional view of another exemplary textured nonwoven web in accordance with the present disclosure comprising a composition site.

FIG. 20A is a schematic diagram showing another exemplary process for printing compositions on the textured nonwoven webs in accordance with the present disclosure.

FIG. 20B is a schematic cross section of an exemplary textured nonwoven web comprising a plurality of composition sites.

FIG. 21A is a schematic diagram showing exemplary spacing of particular elements in an exemplary apparatus in accordance with the present disclosure.

FIG. 22A is a schematic diagram showing an exemplary process for depositing compositions on a textured nonwoven web in accordance with the present invention.

FIG. 22B is a schematic diagram showing another exemplary process for depositing compositions on a textured nonwoven web in accordance with the present invention.

FIG. 23 is a schematic diagram showing an exemplary process for both printing and depositing compositions on a textured nonwoven web in accordance with the present disclosure.

DETAILED DESCRIPTION OF THE INVENTION

Figure 1:
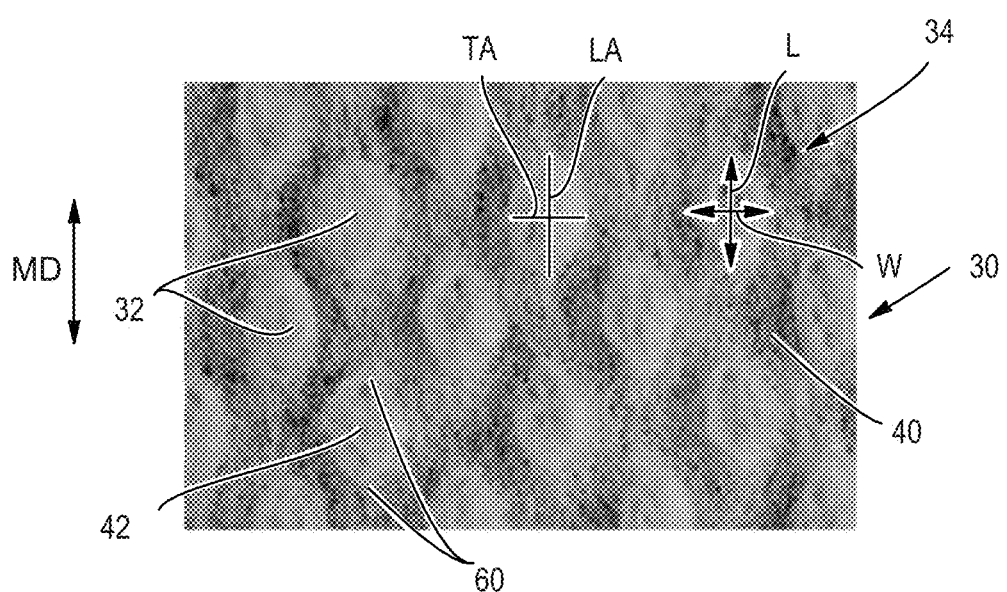
FIG. 1 is a plan view photomicrograph showing one side of the nonwoven material having three-dimensional deformations formed therein, with the protrusions oriented upward.

The textured webs of the present invention comprise composition thereon. The composition may be applied to the textured web in a plurality of discrete sites and/or patterns. In some forms of the present invention, such compositions can increase the hydrophilicity of the textured web in discrete areas on the web. In some forms of the present invention, such compositions can increase the hydrophobicity of the textured web in discrete areas on the web.

The term "absorbent article" includes disposable articles such as sanitary napkins, panty liners, tampons, interlabial devices, wound dressings, diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet. The nonwoven material described herein can comprise at least part of other articles such as scouring pads, wet or dry-mop pads (such as SWIFFER® pads), and the like.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein the term "print file" shall mean any streamed or batched electronic sequence provided to a printer such that all required rendering and formatting has been completed sufficient to allow the printer to execute a print pattern without further prerequisite processing or rendering. Various printers may require that the sequence be provided in specific formats. The sequences may have proprietary layers for either the protocols or the physical layers. Common examples include USB, USB 3.0, USB 3.1, Ethernet 10/100, Ethernet IP, GigE, CameraLink, Coax-Express, LVDS, TTL, RS485, RS422, and Serial Comm; however, the printer may require its own unique protocols instead of industry common protocols.

Textured Nonwoven Webs

The present invention is directed to textured nonwoven webs having discrete three-dimensional deformations, the textured nonwoven web comprising at least a first composition. The deformations provide protrusions on one side of the textured nonwoven webs, and openings on the other side of the textured nonwoven webs. Methods of making the textured nonwoven webs are also disclosed. The textured nonwoven webs can be used in absorbent articles and other articles.

As used herein, the term "nonwoven" refers to a web or material having a structure of individual fibers or threads which are interlaid, but not in a repeating pattern as in a woven or knitted fabric, which latter types of fabrics do not typically have randomly oriented or substantially randomly-oriented fibers. Textured nonwoven webs will have a machine direction (MD) and a cross machine direction (CD) as is commonly known in the art of web manufacture. By "substantially randomly oriented" is meant that, due to processing conditions of precursor webs, there may be a higher amount of fibers oriented in the MD than the CD, or vice versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD.

Textured nonwoven webs and materials are often incorporated into products, such as absorbent articles, at high manufacturing line speeds. Such manufacturing processes can apply compressive and shear forces on the nonwoven webs that may damage certain types of three-dimensional features that have been purposefully formed in such webs. In addition, in the event that the textured nonwoven web is incorporated into a product (such as a disposable diaper) that is made or packaged under compression, it becomes difficult to preserve the three-dimensional character of some types of prior three-dimensional features after the material is subjected to such compressive forces.

Figure 2:
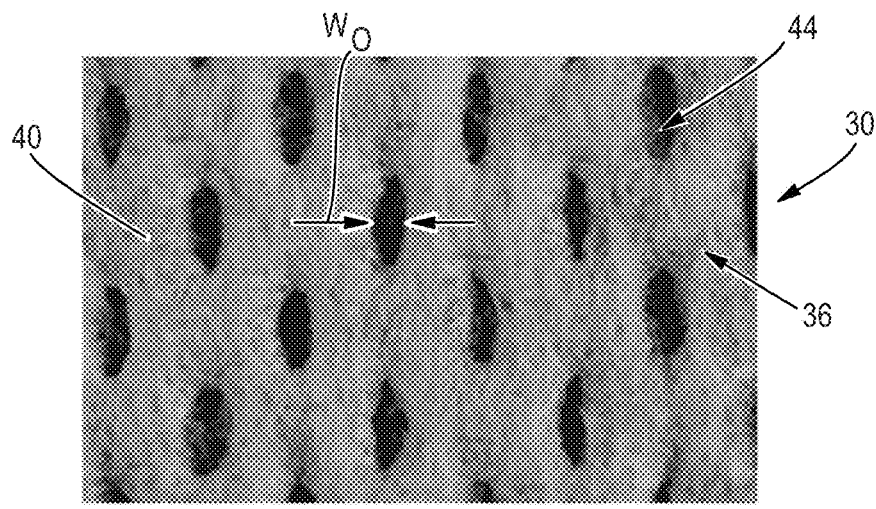
FIG. 2 is a plan view photomicrograph showing the other side of a nonwoven material similar to that shown in FIG. 1, with the openings in the nonwoven facing upward.
Figure 3:
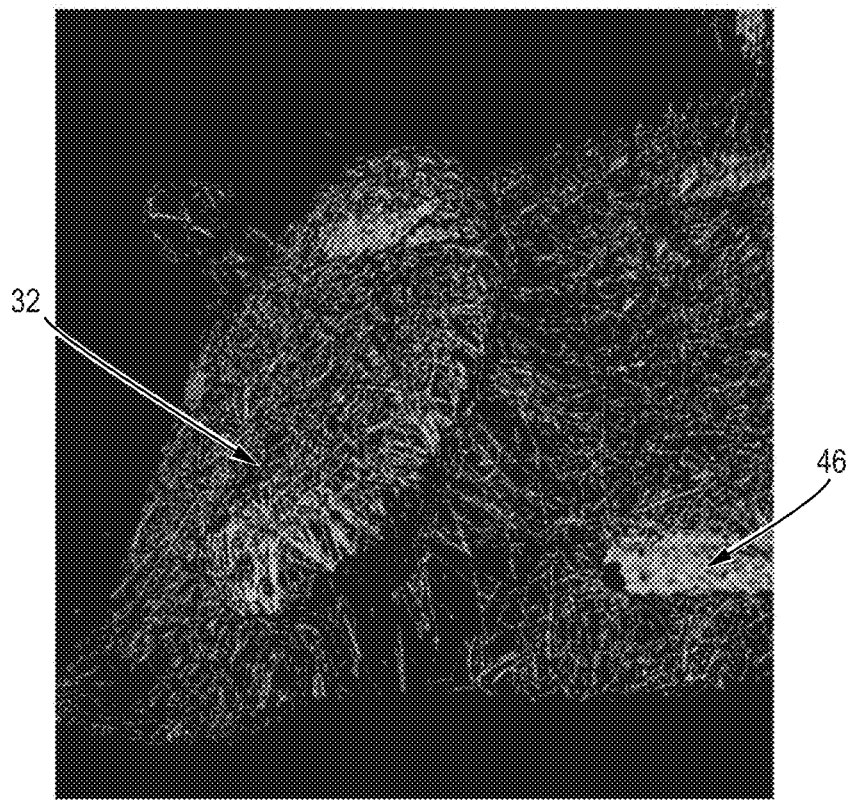
FIG. 3 is a Micro CT scan image showing a perspective view of a protrusion in a single layer nonwoven material.
Figure 4:
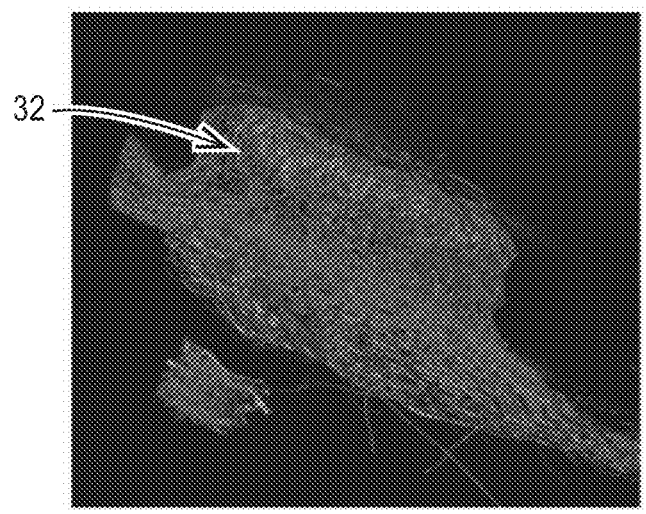
FIG. 4 is a Micro CT scan image showing a side of a protrusion in a single layer nonwoven material.
Figure 5:
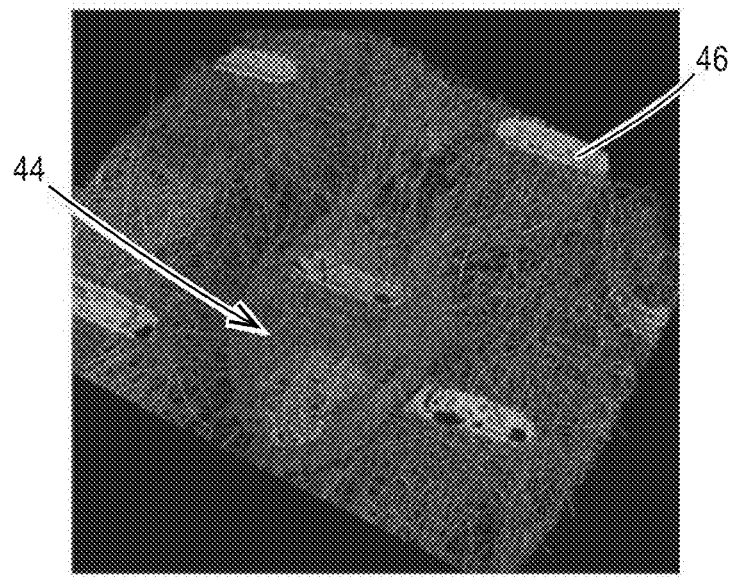
FIG. 5 is a Micro CT scan image showing a perspective view of a deformation with the opening facing upward in a single layer nonwoven material.
Figure 6:
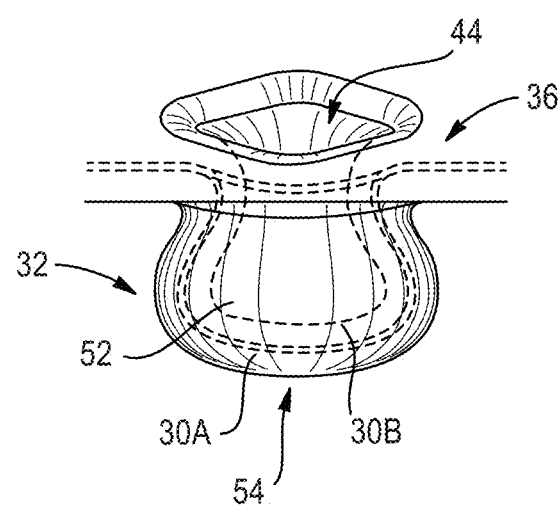
FIG. 6 is a perspective view of a deformation in a two layer nonwoven material with the opening facing upward.

FIGS. 1-15 show examples of textured nonwoven webs 30 with three-dimensional deformations comprising protrusions 32 therein. The textured nonwoven webs 30 have a first surface 34, a second surface 36, and a thickness T therebetween (the thickness being shown in FIG. 8). FIG. 1 shows the first surface 34 of the textured nonwoven web 30 with the protrusions 32 that extend outward from the first surface 34 of the textured nonwoven web 30 oriented upward. FIG. 2 shows the second surface 36 of a textured nonwoven web 30 such as that shown in FIG. 1, having three-dimensional deformations formed therein, with the protrusions oriented downward and the base openings 44 oriented upward. FIG. 3 is a Micro CT scan image showing a perspective view of a protrusion 32. FIG. 4 is a Micro CT scan image showing a side view of a protrusion 32 (of one of the longer sides of the protrusion). FIG. 5 is a Micro CT scan image showing a perspective view of a deformation with the opening 44 facing upward. The textured nonwoven web 30 comprise a plurality of fibers 38 (shown in FIGS. 7, 10 and 11A-11F).

As shown in FIGS. 3 and 5, in some cases, the textured nonwoven web 30 may have a plurality of bonds 46 (such as thermal point bonds) therein to hold the fibers 38 together. Any such bonds 46 are typically present in a precursor material from which the textured nonwoven web 30 are formed.

The protrusions 32 may, in some cases, be formed from looped fibers (which may be continuous) 38 that are pushed outward so that they extend out of the plane of the textured nonwoven web in the positive or negative Z-direction. The protrusions 32 will typically comprise more than one looped fiber. In some cases, the protrusions 32 may be formed from looped fibers and at least some broken fibers. In addition, in the case of some types of nonwoven materials (such as carded materials, which are comprised of shorter fibers), the protrusions 32 may be formed from loops comprising multiple discontinuous fibers. Multiple discontinuous fibers in the form of a loop are shown as layer 30A in FIGS. 11A-11F. The looped fibers may be: aligned (that is, oriented in substantially the same direction); not be aligned; or, the fibers may be aligned in some locations within the protrusions 32, and not aligned in other parts of the protrusions.

In some cases, if male/female forming elements are used to form the protrusions 32, and the female forming elements substantially surround the male forming elements, the fibers in at least part of the protrusions 32 may remain substantially randomly oriented (rather than aligned), similar to their orientation in the precursor web(s). For example, in some cases, the fibers may remain substantially randomly oriented in the cap of the protrusions, but be more aligned in the side walls such that the fibers extend in the Z-direction from the base of the protrusions to the cap. In addition, if the precursor web comprises a multi-layer nonwoven material, the alignment of fibers can vary between layers, and can also vary between different portions of a given protrusion 32 within the same layer.

Referring back to FIGS. 1 and 2, the textured nonwoven web 30 may comprise a generally planar first region 40 and a plurality of discrete integral second regions 42. The term "generally planar" is not meant to imply any particular flatness, smoothness, or dimensionality. Thus, the first region 40 can include other features that provide the first region 40 with a topography. Such other features can include, but are not limited to, small projections, raised network regions around the base openings 44, and other types of features. Thus, the first region 40 is generally planar when considered relative to the second regions 42. The first region 40 can have any suitable plan view configuration. In some cases, the first region 40 is in the form of a continuous inter-connected network which comprises portions that surround each of the deformations.

The plurality of discrete integral second regions 42 comprises the three dimensional deformations described herein. The term "deformation", as used herein, includes both the protrusions 32 on the first surface 34 of the textured nonwoven web 30 and the base openings 44 formed in the second surface 36 of the textured nonwoven web 30. Accordingly, the first region 40 may be termed herein as "undeformed" while the plurality of discrete second regions 42 may be termed "deformed". Both the first surface 34 and the second surface 36 comprise the first region 40.

The base openings 44 are most often not in the form of an aperture or a through-hole. The base openings 44 may instead appear as depressions. The base openings 44 can be analogized to the opening of a bag. A bag has an opening that typically does not pass completely through the bag. In the case of the present nonwoven materials 30, as shown in FIGS. 6-8 and 10, the base openings 44 open into the interior of the protrusions 32.

Figure 7:
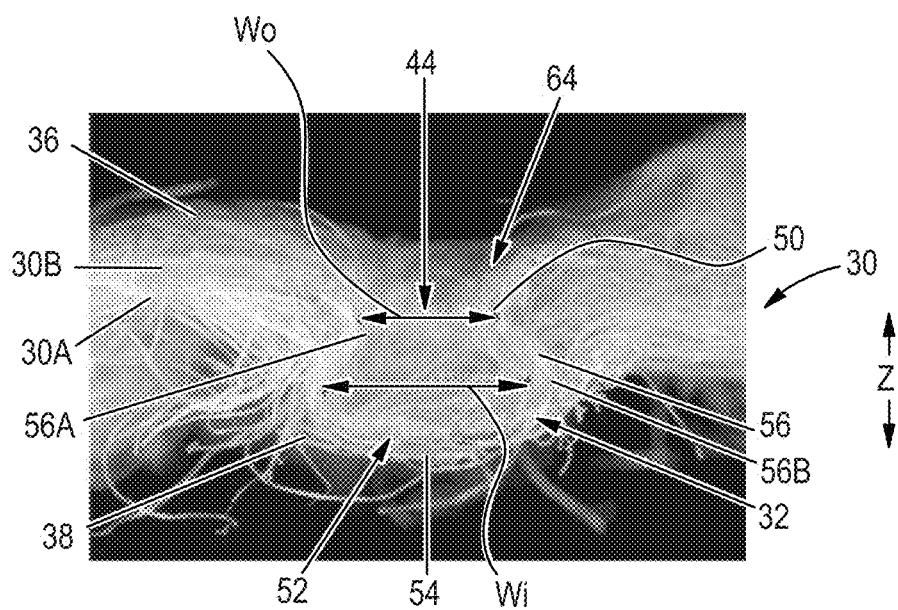
FIG. 7 is a photomicrograph of a cross-section taken along the transverse axis of a deformation showing one example of a multi-layer nonwoven material having a three-dimensional deformation in the form of a protrusion on one side of the material that provides a wide opening on the other side of the material, with the opening facing upward.

FIG. 7 shows one example of a multi-layer textured nonwoven web 30 having a three-dimensional deformation in the form of a protrusion 32 on one side of the material that provides a wide base opening 44 on the other side of the material. The dimensions of "wide" base openings are described in further detail below. In this case, the base opening 44 is oriented upward in the figure. When there is more than one nonwoven layer, the individual layers can be designated 30A, 30B, etc. The individual layers 30A and 30B each have first and second surfaces, which can be designated similarly to the first and second surfaces 34 and 36 of the nonwoven material (e.g., 34A and 36A for the first and second surfaces of the first layer 30A; and, 34B and 36B for the first and second surfaces of the second layer 30B).

Figure 8:
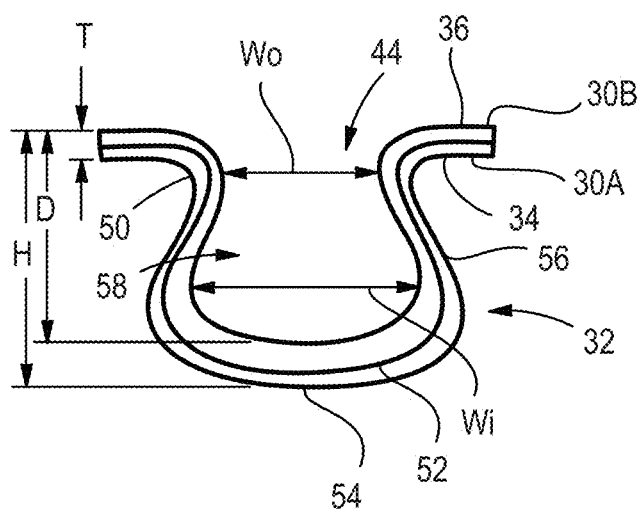
FIG. 8 is a schematic view of the protrusion shown in FIG. 7.
Figure 11C:
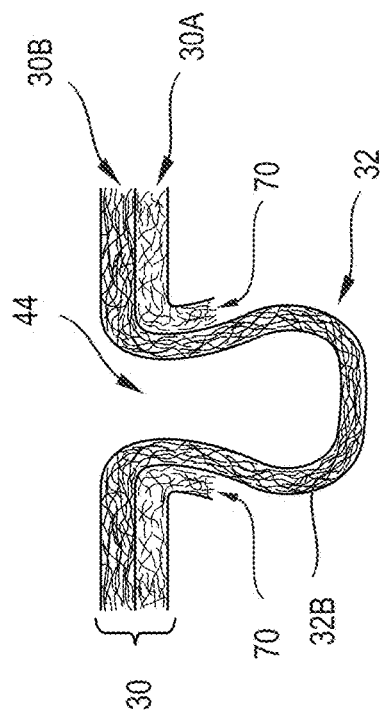
FIG. 11C is a cross-sectional view taken along the transverse axis of a deformation of an alternative embodiment of a multi-layer nonwoven web shown with the base opening facing upward.

As shown in FIGS. 7 and 8, the protrusions 32 comprise: a base 50 proximate the first surface 34 of the textured nonwoven web 30; an opposed enlarged distal portion or cap portion, or "cap" 52, that extends to a distal end 54; side walls (or "sides") 56; an interior 58; and a pair of ends 60 (the latter being shown in FIG. 1). The "base" 50 of the protrusions 32 comprises the narrowest portion of the protrusion when viewed from one of the ends of the protrusion. The term "cap" does not imply any particular shape, other than it comprises the wider portion of the protrusion 32 that includes and is adjacent to the distal end 54 of the protrusion 32. The side walls 56 have an inside surface 56A and an outside surface 56B. As shown in FIGS. 11 and 12, the side walls 56 transition into, and may comprise part of the cap 52. Therefore, it is not necessary to precisely define where the side walls 56 end and the cap 52 begins. The cap 52 will have a maximum interior width, $W_I$, between the inside surfaces 56A of the opposing side walls 56. The cap 52 will also have a maximum exterior width W between the outside surfaces 56B of the opposing side walls 56. The ends 60 (shown in FIG. 1) of the protrusions 32 are the portions of the protrusions that are spaced furthest apart along the longitudinal axis, L, of the protrusions.

Referring back to FIGS. 7 and 8, the narrowest portion of the protrusion 32 defines the base opening 44. The base opening 44 has a width $W_O$. The base opening 44 may be located (in the z-direction) between the plane defined by the second surface 36 of the material and the distal end 54 of the protrusion. The textured nonwoven web 30 may have an opening in the second surface 36 (the "second surface opening" 64) that transitions into the base opening 44 (and vice versa), and is the same size as, or larger than the base opening 44. The base opening 44 will, however, generally be discussed more frequently herein since its size will often be more visually apparent to the consumer in those embodiments where the textured nonwoven web 30 is placed in an article with the base openings 44 visible to the consumer. It should be understood that in some forms of the present invention, such as those in which the base openings 44 face outward (for example, toward a consumer and away from an absorbent core in an absorbent article), it may be desirable for the base openings 44 not to be covered and/or closed off by another web.

Still referring to FIGS. 7 and 8, the protrusions 32 have a depth D measured from the second surface 36 of the textured nonwoven web to the interior of the protrusion at the distal end 54 of the protrusions. The protrusions 32 have a height H measured from the second surface 36 of the textured nonwoven web to the distal end 54 of the protrusions. In most cases the height H of the protrusions 32 will be greater than the thickness T of the first region 40. The relationship between the various portions of the deformations may be such that as shown in FIG. 7, when viewed from the end, the maximum interior width $W_i$ of the cap 52 of the protrusions is wider than the width, $W_O$, of the base opening 44. In some forms, a ratio of the circumference of the protrusions 32 to the length of the second surface opening 64 is less than 4 to 1. Details regarding the measurement of this ratio are provided in the section entitled "Test Methods."

The protrusions 32 may be of any suitable shape. Since the protrusions 32 are three-dimensional, describing their shape depends on the angle from which they are viewed. When viewed from above (that is, perpendicular to the plane of the web, or plan view) such as in FIG. 1, suitable shapes include, but are not limited to: circular, diamond-shaped, rounded diamond-shaped, U.S. football-shaped, oval-shaped, clover-shaped, heart-shaped, triangle-shaped, tear-drop shaped, and elliptical-shaped. (The base openings 44 will typically have a shape similar to the plan view shape of the protrusions 32.) In other cases, the protrusions 32 (and base openings 44) may be non-circular. The protrusions 32 may have similar plan view dimensions in all directions, or the protrusions may be longer in one dimension than another. That is, the protrusions 32 may have different length and width dimensions. If the protrusions 32 have a different length than width, the longer dimension will be referred to as the length of the protrusions. The protrusions 32 may, thus, have a ratio of length to width, or an aspect ratio. The aspect ratios can range from about 1.1:1 to about 10:1.

Referring back to FIG. 1, the protrusions 32 may have a width, W, that varies from one end 60 to the opposing end 60 when the protrusions are viewed in plan view. The width W may vary with the widest portion of the protrusions in the middle of the protrusions, and the width of the protrusions decreasing at the ends 60 of the protrusions. In other cases, the protrusions 32 could be wider at one or both ends 60 than in the middle of the protrusions. In still other cases, protrusions 32 can be formed that have substantially the same width from one end of the protrusion to the other end of the protrusion. If the width of the protrusions 32 varies along the length of the protrusions, the portion of the protrusion where the width is the greatest is used in determining the aspect ratio of the protrusions.

The protrusions 32 have a length L that is greater than their width W, the length of the protrusions may be oriented in any suitable direction relative to the nonwoven material 30. For example, the length of the protrusions 32 (that is, the longitudinal axis, LA, of the protrusions) may be oriented in the machine direction, the cross-machine direction, or any desired orientation between the machine direction and the cross-machine direction. The protrusions 32 also have a transverse axis TA generally orthogonal to the longitudinal axis LA in the MD-CD plane. As shown in FIGS. 1 and 2, the longitudinal axis LA may be parallel to the MD. In some forms, all the spaced apart protrusions 32 may have generally parallel longitudinal axes LA.

The protrusions 32 may have any suitable shape when viewed from the side. Suitable shapes include those in which there is a distal portion or "cap" with an enlarged dimension and a narrower portion at the base when viewed from at least one side. The term "cap" is analogous to the cap portion of a mushroom. (The cap does not need to resemble that of any particular type of mushroom. In addition, the protrusions 32 may, but need not, have a mushroom-like stem portion.) In some cases, the protrusions 32 may be referred to as having a bulbous shape when viewed from the end 60, such as in FIG. 11. The term "bulbous", as used herein, is intended to refer to the configuration of the protrusions 32 as having a cap 52 with an enlarged dimension and a narrower portion at the base when viewed from at least one side (particularly when viewing from one of the shorter ends 60) of the protrusion 32. The term "bulbous" is not limited to protrusions that have a circular or round plan view configuration that is joined to a columnar portion. The bulbous shape, in as shown (where the longitudinal axis LA of the deformations 32 is oriented in the machine direction), may be most apparent if a section is taken along the transverse axis TA of the deformation (that is, in the cross-machine direction). The bulbous shape may be less apparent if the deformation is viewed along the length (or longitudinal axis LA) of the deformation such as in FIG. 4.

Referring to FIGS. 3-8, the protrusions 32 may comprise fibers 38 that at least substantially surround the sides of the protrusions. This means that there are multiple fibers that extend (e.g., in the Z-direction) from the base 50 of the protrusions 32 to the distal end 54 of the protrusions, and contribute to form a portion of the sides 56 and cap 52 of a protrusion. In some cases, the fibers may be substantially aligned with each other in the Z-direction in the sides 56 of the protrusions 32. The phrase "substantially surround", thus, does not require that each individual fiber be wrapped in the X-Y plane substantially or completely around the sides of the protrusions. If the fibers 38 are located completely around the sides of the protrusions, this would mean that the fibers are located 360° around the protrusions. The protrusions 32 may be free of large openings at their ends 60, such as those openings 18 at the leading end and trailing end of the tufts shown in FIG. 1. In some cases, the protrusions 32 may have an opening at only one of their ends, such as at their trailing end. The protrusions 32 also differ from embossed structures such as shown in FIG. 4. Embossed structures typically do not have distal portions that are spaced perpendicularly away (that is, in the Z-direction) from their base that are wider than portions that are adjacent to their base, as in the case of the cap 52 on the present protrusions 32.

The protrusions 32 may have certain additional characteristics. Now referring to FIGS. 7 and 8, the protrusions 32 may be substantially hollow. As used herein, the term "substantially hollow" refers to structures which the protrusions 32 are substantially free of fibers in interior of protrusions. The term "substantially hollow", does not, however, require that the interior of the protrusions must be completely free of fibers. Thus, there can be some fibers inside the protrusions. "Substantially hollow" protrusions are distinguishable from filled three-dimensional structures, such as those made by laying down fibers, such as by airlaying or carding fibers onto a forming structure with recesses therein.

The sidewalls 56 of the protrusions 32 can have any suitable configuration. The configuration of the side walls 56, when viewed from the end of the protrusion such as in FIG. 7, can be linear or curvilinear, or the side walls can be formed by a combination of linear and curvilinear portions. The curvilinear portions can be concave, convex, or combinations of both. For example, the side walls 56 may comprise portions that are curvilinear concave inwardly near the base of the protrusions and convex outwardly near the cap of the protrusions. The sidewalls 56 and the area around the base opening 44 of the protrusions may, under 20× magnification, have a visibly significantly lower concentration of fibers per given area (which may be evidence of a lower basis weight or lower opacity) than the portions of the nonwoven in the unformed first region 40. The protrusions 32 may also have thinned fibers in the sidewalls 56. The fiber thinning, if present, will be apparent in the form of necked regions in the fibers 38 as seen in scanning electron microscope (SEM) images taken at 200× magnification. Thus, the fibers may have a first cross-sectional area when they are in the undeformed nonwoven precursor web, and a second cross-sectional area in the side walls 56 of the protrusions 32 of the deformed nonwoven web, wherein the first cross-sectional area is greater than the second cross-sectional area. The side walls 56 may also comprise some broken fibers as well. In some embodiments, the side walls 56 may comprise greater than or equal to about 30%, alternatively greater than or equal to about 50% broken fibers.

In some forms, the distal end 54 of the protrusions 32 may be comprised of original basis weight, non-thinned, and non-broken fibers. If the base opening 44 faces upward, the distal end 54 will be at the bottom of the depression that is formed by the protrusion. The distal end 54 will be free from apertures formed completely through the distal end. Thus, the textured nonwoven web may be nonapertured. The term "apertures", as used herein, refers to holes formed in the nonwovens after the formation of the nonwovens, and does not include the pores typically present in nonwovens. The term "apertures" also does not refer to irregular breaks (or interruptions) in the nonwoven material(s) such as shown in FIGS. 11D-11F resulting from localized tearing of the material(s) during the process of forming deformations therein, which breaks may be due to variability in the precursor material(s). The distal end 54 may have relatively greater fiber concentration in comparison to the remaining portions of the structure that forms the protrusions. The fiber concentration can be measured by viewing the sample under a microscope and counting the number of fibers within an area. As described in greater detail below, however, if the nonwoven web is comprised of more than one layer, the concentration of fibers in the different portions of the protrusions may vary between the different layers.

The protrusions 32 may be of any suitable size. The size of the protrusions 32 can be described in terms of protrusion length, width, caliper, height, depth, cap size, and opening size. (Unless otherwise stated, the length L and width W of the protrusions are the exterior length and width of the cap 52 of the protrusions.) The dimensions of the protrusions and openings can be measured before and after compression (under a pressure of 1 kPa, 4 kPa, 7 kPa or 35 KPa, whichever is specified) in accordance with the Accelerated Compression Method described in the Test Methods section. The protrusions have a caliper that is measured between the same points as the height H, but under a 0.5 kPa load, in accordance with the Accelerated Compression Method. All dimensions of the protrusions and openings other than caliper (that is, length, width, height, depth, cap size, and opening size) are measured without pressure applied at the time of making the measurement using a microscope at 20× magnification.

In some forms, the length of the cap 52 may be in a range from about 1.5 mm to about 10 mm. In some forms, the width of the cap (measured where the width is the greatest) may be in a range from about 1.5 mm to about 5 mm. The cap portion of the protrusions may have a plan view surface area of at least about 3 mm$^2$. In some forms, the protrusions may have a pre-compression height H that is in a range from about 1 mm to about 10 mm, alternatively from about 1 mm to about 6 mm. In some forms, the protrusions may have a post-compression height H that is in a range from about 0.5 mm to about 6 mm, alternatively from about 0.5 mm to about 1.5 mm. In some embodiments, the protrusions may have a depth D, in an uncompressed state that is in a range from about 0.5 mm to about 9 mm, alternatively from about 0.5 mm to about 5 mm. In some forms, the protrusions may have a depth D, after compression that is in a range from about 0.25 mm to about 5 mm, alternatively from about 0.25 mm to about 1 mm.

The textured nonwoven web 30 can comprise a composite or laminate of two or more nonwoven materials that are joined together. In such a case, the fibers and properties of the first layer will be designated accordingly (e.g., the first layer is comprised of a first plurality of fibers), and the fibers and properties of the second and subsequent layers will be designated accordingly (e.g., the second layer is comprised of a second plurality of fibers). In a two or more layer structure, there are a number of possible configurations the layers may take following the formation of the deformations therein. These will often depend on the extensibility of the nonwoven materials used for the layers. It is desirable that at least one of the layers have deformations which form protrusions 32 as described herein in which, along at least one cross-section, the width of the cap 52 of the protrusions is greater than the width of the base opening 44 of the deformations. For example, in a two layer structure where one of the layers will serve as the topsheet of an absorbent article and the other layer will serve as an underlying layer (such as an acquisition layer or a secondary topsheet), the layer that has protrusions therein may comprise the topsheet layer. As another example, the acquisition layer or secondary topsheet may comprise the protrusions and face away from a wearer, i.e. toward an absorbent core. The layer that most typically has a bulbous shape will be the one which is in contact with the male forming member during the process of deforming the web. FIGS. 11A-11F show different alternative embodiments of three-dimensional protrusions 32 in multiple layer materials.

Figure 11A:
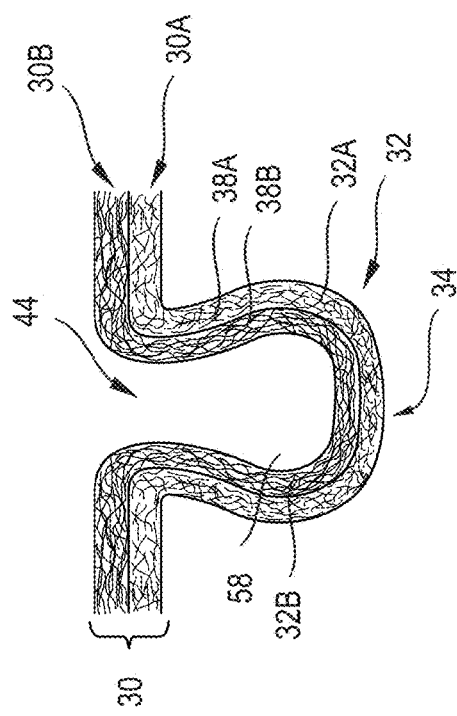
FIG. 11A is a cross-sectional view taken along the transverse axis of a deformation of one embodiment of a multi-layer nonwoven web shown with the base opening facing upward.
Figure 12:
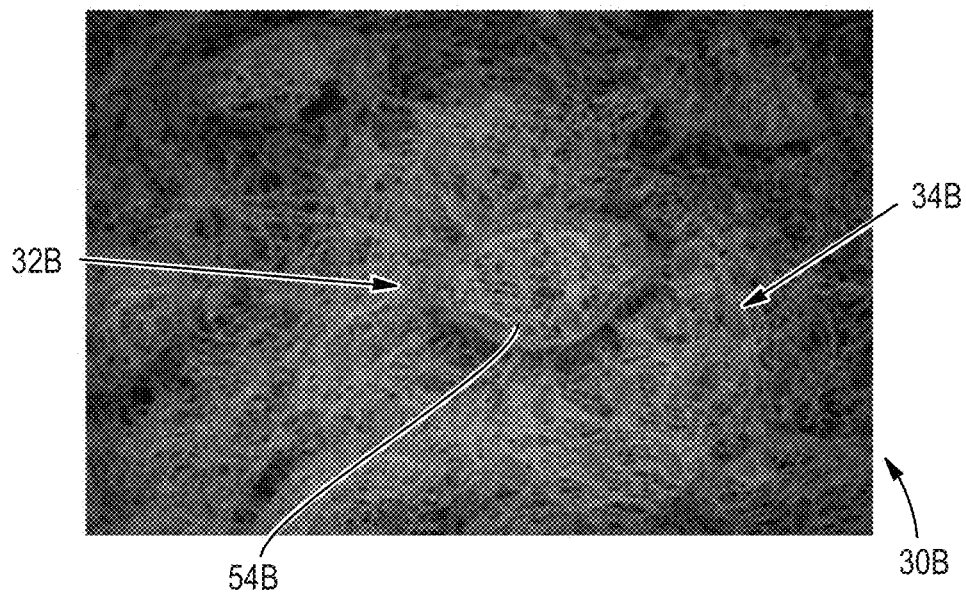
FIG. 12 is a plan view photomicrograph of a nonwoven web with the protrusions oriented upward showing the concentration of fibers in one layer of a two layer structure.

In certain forms, such as shown in FIGS. 7, 8, and 11A, similar-shaped looped fibers may be formed in each layer of multiple layer nonwoven materials, including in the layer 30A that is spaced furthest from the discrete male forming elements during the process of forming the protrusions 32 therein, and in the layer 30B that is closest to the male forming elements during the process. In the protrusions 32, portions of one layer such as 30B may fit within the other layer, such as 30A. These layers may be referred to as forming a "nested" structure in the protrusions 32. Formation of a nested structure may require the use of two (or more) highly extensible nonwoven precursor webs. In the case of two layer materials, nested structures may form two complete loops, or (as shown in some of the following drawing figures) two incomplete loops of fibers.

As shown in FIG. 11A, a three-dimensional protrusion 32 comprises a primary protrusion 32A formed in the first layer 30A and a secondary protrusion 32B formed in the second layer 30B. In one form, the first layer 30A may be incorporated into an absorbent article as an acquisition layer or secondary topsheet, and the second layer 30B may be a topsheet, and the protrusions formed by the two layers may fit together (that is, are nested). In such forms, the protrusions 32A and 32B formed by the first and second layers 30A and 30B fit closely together. The three-dimensional primary protrusion 32A comprises a plurality of fibers 38A and the three-dimensional secondary protrusion 32B comprises a plurality of fibers 38B. The three-dimensional secondary protrusion 32B is nested into the three-dimensional primary protrusion 32A. As shown, the fibers 38A in the first layer 30A are shorter in length than the fibers 38B in the second layer 30B. In other forms, the relative length of fibers in the layers may be the same, or in the opposite relationship wherein the fibers in the first layer are longer than those in the second layer. In addition, for any forms of the present invention described herein, the nonwoven layers can be inverted when incorporated into an absorbent article, or other article, so that the protrusions 32 face upward (or outward). In such a case, the material suitable for the topsheet will be used in layer 30A, and material suitable for the underlying layer will be used in layer 30B.

Figure 11B:
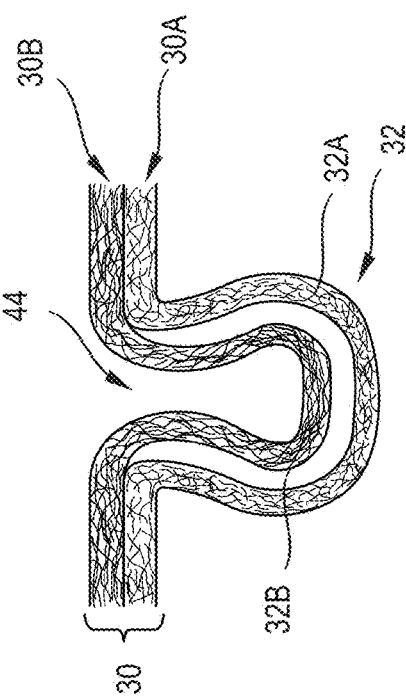
FIG. 11B is a cross-sectional view taken along the transverse axis of a deformation of an alternative embodiment of a multi-layer nonwoven web shown with the base opening facing upward.

FIG. 11B shows that the nonwoven layers need not be in a contacting relationship within the entirety of the protrusion 32. Thus, the protrusions 32A and 32B formed by the first and second layers 30A and 30B may have different heights and/or widths. The two materials may have substantially the same shape in the protrusion 32 as shown in FIG. 11B (where one of the materials has the same curvature as the other). In other forms, however, the layers may have different shapes. It should be understood that FIG. 11B shows only one possible arrangement of layers, and that many other variations are possible, but that as in the case of all the figures, it is not possible to provide a drawing of every possible variation.

As shown in FIG. 11C, one of the layers, such as first layer 30A (e.g., an acquisition layer or secondary topsheet) may be ruptured in the area of the three-dimensional protrusion 32. As shown in FIG. 11C, the protrusions 32 are only formed in the second layer 30B (e.g., the topsheet) and extend through openings in the first layer 30A. That is, the three-dimensional protrusion 32B in the second layer 30B interpenetrates the ruptured first layer 30A. Such a structure may place the topsheet in direct contact an underlying distribution layer or absorbent core, which may lead to improved dryness. In such an embodiment, the layers are not considered to be "nested" in the area of the protrusion. (In the other embodiments shown in FIGS. 11D-11F, the layers would still be considered to be "nested".) Such a structure may be formed if the material of the second layer 30B is much more extensible than the material of the first layer 30A. In such a case, the openings can be formed by locally rupturing first precursor web by the process described in detail below. The ruptured layer may have any suitable configuration in the area of the protrusion 32. Rupture may involve a simple splitting open of first precursor web, such that the opening in the first layer 30A remains a simple two-dimensional aperture. However, for some materials, portions of the first layer 30A can be deflected or urged out-of-plane (i.e., out of the plane of the first layer 30A) to form flaps 70. The form and structure of any flaps is highly dependent upon the material properties of the first layer 30A. Flaps can have the general structure shown in FIG. 11C. In other embodiments, the flaps 70 can have a more volcano-like structure, as if the protrusion 32B is erupting from the flaps.

Alternatively, as shown in FIG. 11D-11F, one or both of the first layer 30A and the second layer 30B may be interrupted (or have a break therein) in the area of the three-dimensional protrusion 32. FIGS. 11D and 11E show that the three-dimensional protrusion 32A of the first layer 30A may have an interruption 72A therein. The three-dimensional protrusion 32B of the non-interrupted second layer 30B may coincide with and fit together with the three-dimensional protrusion 32A of the interrupted first layer 30A. Alternatively, in some forms, as shown in FIG. 11F, both the first and second layers 30A and 30B may have interruptions, or breaks, therein (72A and 72B, respectively). In such forms, the interruptions in the layers 30A and 30B are in different locations in the protrusion 32. FIGS. 11D-

11F show unintentional random or inconsistent breaks in the materials typically formed by random fiber breakage, which are generally misaligned and can be in the first or second layer, but are not typically aligned and completely through both layers. Thus, there typically will not be an aperture formed completely through all of the layers at the distal end 54 of the protrusions 32.

For dual layer and other multiple layer structures, the basis weight distribution (or the concentration of fibers) within the deformed material 30, as well as the distribution of any thermal point bonds 46 can be different between the layers. As used herein, the term "fiber concentration" has a similar meaning as basis weight, but fiber concentration refers to the number of fibers/given area, rather than g/area as in basis weight. In the case of bond sites 46, the fibers may be melted which may increase the density of the material in the bond sites 46, but the number of fibers will typically be the same as before melting.

Some such dual and multiple layer nonwoven materials may be described in terms of such differences between layers, without requiring one or more of the other features described herein (such as characteristics of the cap portion; controlled collapse under compression; and varying width of the protrusions). Of course such dual and multiple layer nonwoven materials may have any of these other features.

In such dual and multiple layer nonwoven materials each of the layers comprises a plurality of fibers, and in certain embodiments, the protrusions 32 will be formed from fibers in each of the layers. For example, one of the layers, a first layer, may form the first surface 34 of the textured nonwoven web 30, and one of the layers, a second layer, may form the second surface 36 of the textured nonwoven web 30. A portion of the fibers in the first layer form part of: the first region 40, the side walls 56 of the protrusions, and the distal ends 54 of the protrusions 32. A portion of the fibers in the second layer form part of: the first region 40, the side walls 56 of the protrusions, and the distal ends 54 of the protrusions 32.

Figure 13:
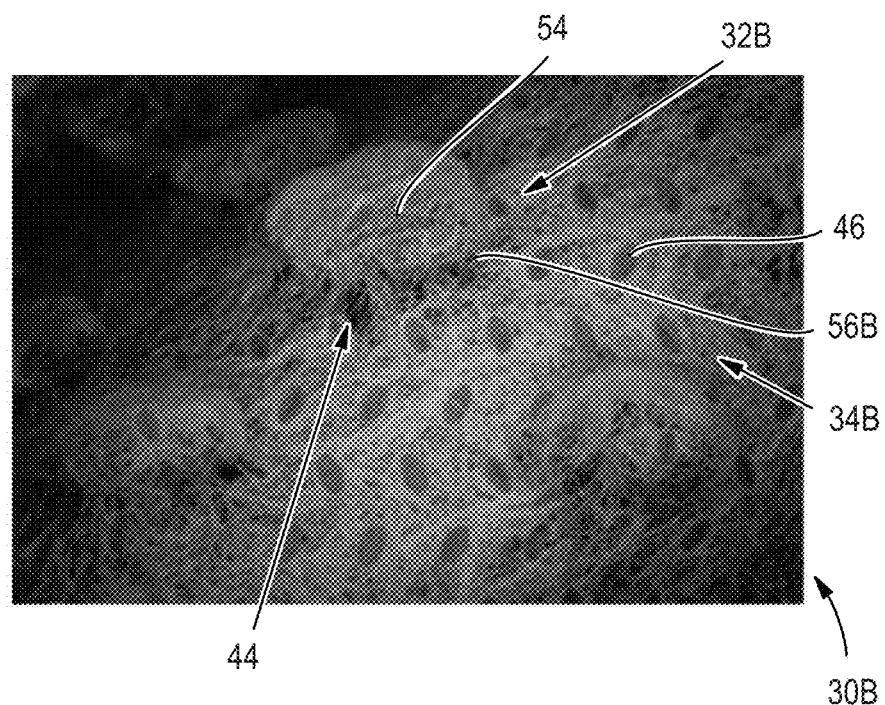
FIG. 13 is a perspective view photomicrograph showing the reduced fiber concentration in the side walls of the protrusions in a layer similar to that shown in FIG. 12.
Figure 14:
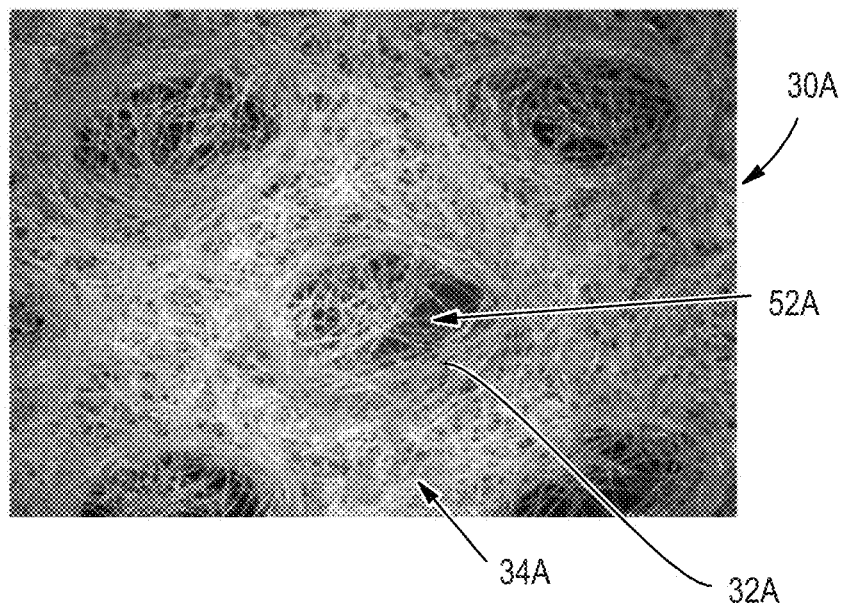
FIG. 14 is a plan view photomicrograph of a nonwoven web with the protrusions oriented upward showing the reduced concentration of fibers in the cap of a protrusion in the other layer (i.e. vs. the layer shown in FIG. 12) of a two layer structure.
Figure 15A:
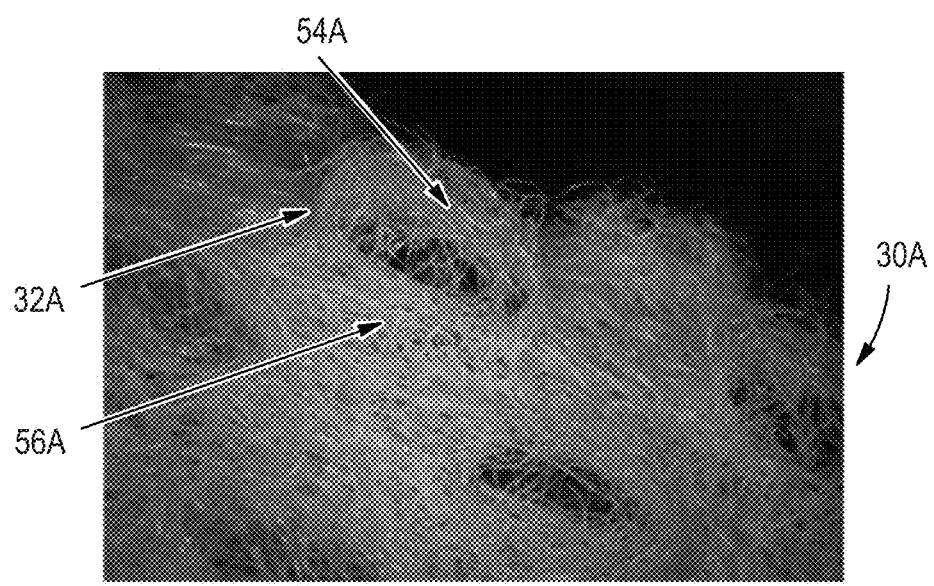
FIG. 15A is a perspective view photomicrograph showing the decreased fiber concentration in the side walls of the protrusions in a layer similar to that shown in FIG. 14.
Figure 15B:
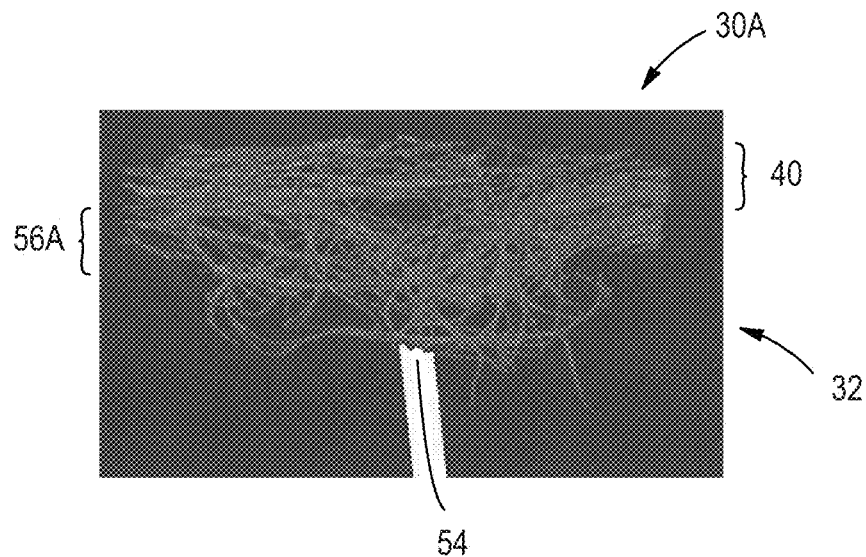
FIG. 15B is a Micro CT scan image showing the side of a protrusion in a single layer of nonwoven material with the protrusion oriented downward.
Figure 15C:
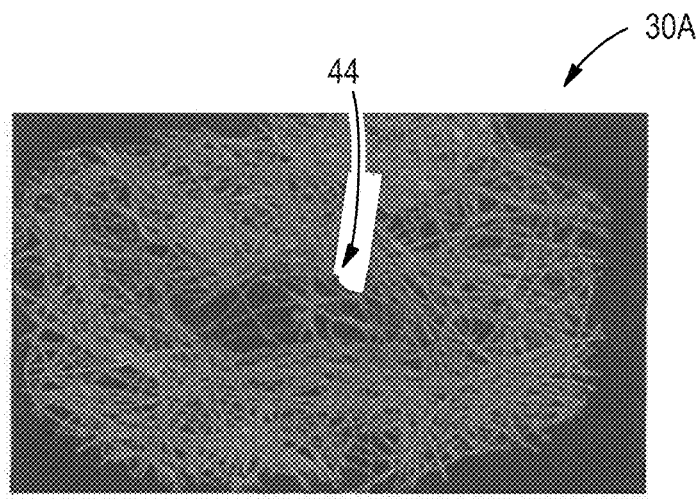
FIG. 15C is a Micro CT scan plan view image showing the base opening of a deformation in a single layer of nonwoven material.

As shown in FIG. 12, the nonwoven layer in contact with a male forming element (e.g., 30B) may have a large portion at the distal end 54B of the protrusion 32B with a similar basis weight to the original nonwoven (that is, to the first region 40). As shown in FIG. 13, the basis weight in the sidewalls 56B of the protrusion 32B and near the base opening 44 may be lower than the basis weight of the first region 40 of the nonwoven layer and the distal end 54 of the protrusion 32B. As shown in FIG. 14, the nonwoven layer in contact with a female forming element (e.g., 30A) may, however, have significantly less basis weight in the cap 52A of the protrusion 32A than in the first region 40 of the nonwoven layer. As shown in FIG. 15A, the sidewalls 56A of the protrusion 32A may have less basis weight than the first region 40 of the nonwoven. FIGS. 15B and 15C show that the nonwoven layer 30A in contact with the female forming element may have a fiber concentration that is greatest in the first region 40 (at the upper part of the image in FIG. 15B) and lowest at the distal end 54 of the protrusion 32. The fiber concentration in the side wall 56A, in this case, may be less than that of the first region 40, but greater than that at the distal end 54 of the protrusion 32.

Forming deformations in the nonwoven material may also affect the bonds 46 (thermal point bonds) within the layer (or layers). In some forms, the bonds 46 within the distal end 54 of the protrusions 32 may remain intact (not be disrupted) by the deformation process that formed the protrusions 32. In the side walls 56 of the protrusions 32, however, the bonds 46 originally present in the precursor web may be disrupted.

When it is said that the bonds 46 may be disrupted, this can take several forms. The bonds 46 can be broken and leave remnants of a bond. In other cases, such as where the nonwoven precursor material is underbonded, the fibers can disentangle from a lightly formed bond site (similar to untying a bow), and the bond site will essentially disappear. In some cases, after the deformation process, the side walls 56 of at least some of the protrusions 32 may be substantially free (or completely free) of thermal point bonds.

Numerous forms of dual layer and other multiple layer structures are possible. For example, a nonwoven layer 30B such as that shown in FIGS. 12 and 13 could be oriented with its base openings facing upward, and could serve as a topsheet of a dual or multiple layer nonwoven structure (with at least one other layer serving as an acquisition layer or secondary topsheet). In such forms, the bonds 46 within first region 40 of nonwoven layer 30B and the distal end 54 of the protrusions 32 remain intact. In the side walls 56 of the protrusions 32, however, the bonds 46 originally present in the precursor web are disrupted such that the side walls 56 are substantially free of thermal point bonds. Such a topsheet could be combined with an acquisition layer or secondary topsheet in which the concentration of fibers within the layer 30A in the first region 40 and the distal end 54 of the protrusions 32 is also greater than the concentration of fibers in the side walls 56 of the protrusions 32.

For the sake of simplicity, a secondary topsheet in an absorbent article can be configured similar to the acquisition layer. In other forms, the acquisition layer 30A described in the preceding paragraph may have thermal point bonds 46 within first region 40 of nonwoven layer 30B and the distal end 54 of the protrusions 32 that remain intact. In the side walls 56 of the protrusions 32, however, the bonds 46 originally present in the precursor web comprising the acquisition layer 30A are disrupted such that the side walls 56 of the acquisition layer 30A are substantially free of thermal point bonds. In other cases, the thermal point bonds in the acquisition layer 30A at the top of the protrusions 32 may also be disrupted so that the distal end 54 of at least some of the protrusions are substantially or completely free of thermal point bonds.

In other forms, a dual layer or multiple layer structure may comprise a topsheet and an acquisition layer that is oriented with its base openings facing upward in which the concentration of fibers at the distal end 54 of each layer (relative to other portions of the layer) differs between layers. For example, in one specific form of the present invention, in the layer that forms the topsheet (second layer), the concentration of fibers in the first region and the distal ends of the protrusions are each greater than the concentration of fibers in the side walls of the protrusions. In the layer that forms the acquisition layer (first layer), the concentration of fibers in the first region of the acquisition layer may be greater than the concentration of fibers in the distal ends of the protrusions. In a variation of this embodiment, the concentration of fibers in the first region of the first layer (acquisition layer) is greater than the concentration of fibers in the side walls of the protrusions in the first layer, and the concentration of fibers in the side walls of the protrusions in the first layer is greater than the concentration of fibers forming the distal ends of the protrusions in the first layer. In some embodiments in which the first layer comprises a spunbond nonwoven material (in which the precursor material had thermal point bonds distributed substantially evenly throughout), a portion of the fibers that form the first region in the first layer comprise thermal point bonds, and the portion of the fibers in the first layer forming the side walls and distal ends of at least some of the protrusions may be substantially free of thermal point bonds. In such forms, in at least some of the protrusions, at least some of the fibers in the first layer may form a nest or circle around (that is, encircle) the perimeter of the protrusion at the transition between the wide wall and the base of the protrusion as shown in FIG. 15A.

The base openings 44 can be of any suitable shape and size. The shape of the base opening 44 will typically be similar to, or the same as, the plan view shape of the corresponding protrusions 32. And, for those forms—where the base openings 44 face outward toward a consumer—it is believed that the base openings 44 should be sufficiently large such that fluid insults are readily acquired. It is believed that the base openings may have width dimension of greater than about 1 mm, greater than about 1.5 mm, greater than about 2.5 mm, less than about 4 mm, specifically including all values within these ranges and any ranges created thereby. The base openings 44 may have a dimension (as measured according to the Opening Dimension Test Method disclosed herein) which is greater than about 1 mm, greater than about 1.5 mm, greater than about 2.5 mm, less than about 5 mm, specifically including all values within these ranges and any ranges created thereby. The base openings 44 may have an aspect ratio that ranges from about 1:1 to 20:1, alternatively from about 1:1 to 10:1. Measurements of the dimensions of the base opening can be made on a photomicrograph. When the size of the width of the base opening 44 is specified herein, it will be appreciated that if the openings are not of uniform width in a particular direction, the width, $W_O$, is measured at the widest portion as shown in FIG. 2. The textured nonwoven web of the present invention and the method of making the same may create deformations with a wider opening than certain prior structures which have a narrow base. This allows the base openings 44 to be more visible to the naked eye. The width of the base opening 44 is of interest because, being the narrowest portion of the opening, it will be most restrictive of the size of the opening. The deformations retain their wide base openings 44 after compression perpendicular to the plane of the first region 40. Additionally, for those forms where the textured nonwoven web 30 forms a portion of a topsheet of a disposable absorbent article—such that the base openings 44 form a portion of the wearer-facing surface of the article—appropriately sized base openings can allow for better acquisition speed of liquid insults. It is believed that where the base openings 44 are appropriately sized as described above, good acquisition speed of liquid insults can be achieved. In contrast, where the base openings 44 are not sufficiently large, acquisition speed of liquid insults may be detrimentally impacted.

Moreover, the appropriate size of the base openings 44 can vary depending upon the application of the textured nonwoven web 30. For example, in the context of baby diapers, the expected volume of liquid insult from a newborn may be very different from that of a child near the toilet training stage. Accordingly, the base openings 44—when oriented toward the wearer—may be a first size in the absorbent article for the newborn and may be a second size in the absorbent article for the older child. The second size of the base openings 44 may be larger than the first size. Similarly, in the context of adult incontinence, the base openings 44 may be a third size which is larger than the second size and the first size. And, in the context of menstrual pads and/or sanitary napkins, the expected volume of liquid insults may be much less than that of any of the foregoing. In such cases the base openings 44 may be a fourth size which is smaller than the third size and may be smaller than the second size. And, in some forms, may be smaller than the first size.

Figure 10A:
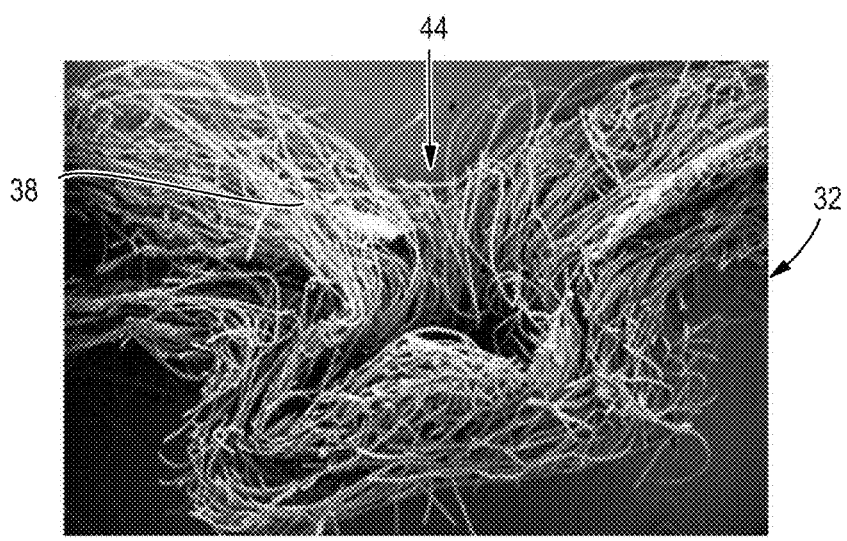
FIG. 10A is a photomicrograph of the cross-section of a protrusion taken along the transverse axis of the protrusion showing the protrusion after it has been subjected to compression.
Figure 10B:
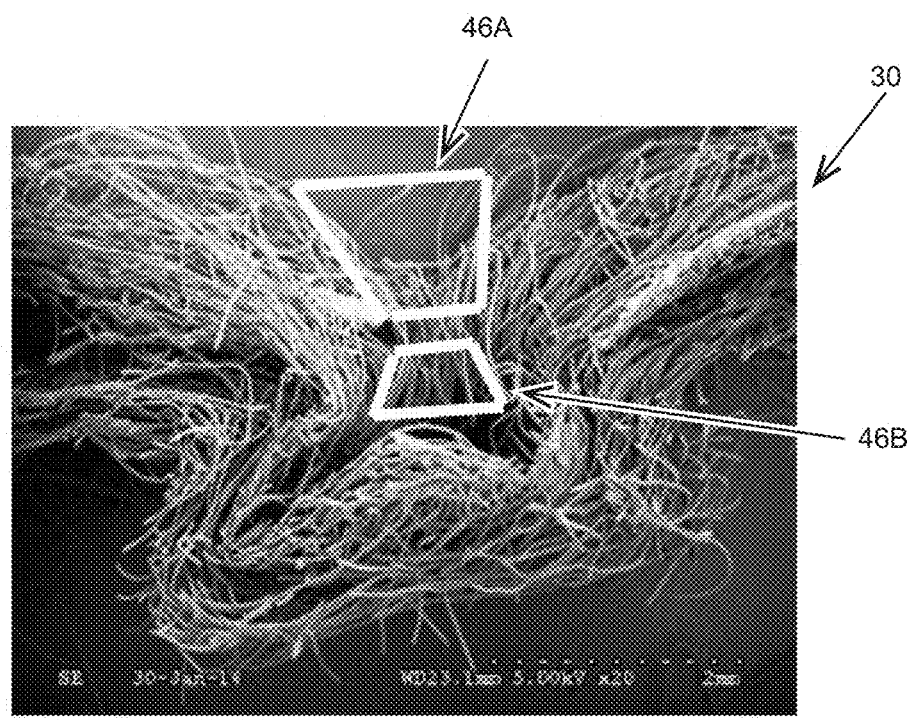
FIG. 10B is the photomicrograph of FIG. 10A highlighting the base opening and interior of the protrusion.

Now referring to FIGS. 7, 8, and 10B, the opening in the second surface 36 (the "second surface opening" 64) that transitions into the base opening 44 (and vice versa), may be larger than the base opening 44 after compression of the textured nonwoven web 30 as described herein. Generally, a transition from the surface opening 64 to the base opening 44 can take on a conical or frustoconical shape, i.e. frustum 46A, where the base of the frustum 46A is oriented toward the second surface opening 64. Past the base opening 44, the interior of the protrusion 32 may form a second frustum 46B which has a base oriented toward the distal end 54 of the protrusion 32.

The deformations may compress under load. In some cases, it may be desirable that the load is low enough so that, if the nonwoven is worn against a wearer's body, with the deformations in contact with the wearer's body, the deformations will be soft and will not imprint the skin. This applies in cases where either the protrusions 32 or the base openings 44 are oriented so that they are in contact with the wearer's body. For example, it may be desirable for the deformations to compress under pressures of 2 kPa or less. In other cases, it will not matter if the deformations imprint the wearer's skin. It may be desirable for at least one of the protrusions 32 in the nonwoven material 30 to collapse or buckle in the controlled manner described below under the 7 kPa load when tested in accordance with the Accelerated Compression Method in the Test Methods section below. Alternatively, at least some, or in other cases, a majority of the protrusions 32 may collapse in the controlled manner described herein. Alternatively, substantially all of the protrusions 32 may collapse in the controlled manner described herein. The ability of the protrusions 32 to collapse may also be measured under a load of 35 kPa, 7 kPa or 1 kPa. The 1 kPa, 4 kPa, 7 kPa and 35 kPa loads simulate manufacturing and compression packaging conditions. Wear conditions can range from no or limited pressure (if the wearer is not sitting on the absorbent article) up to 2 kPa, 7 kPa, or more.

Figure 9:
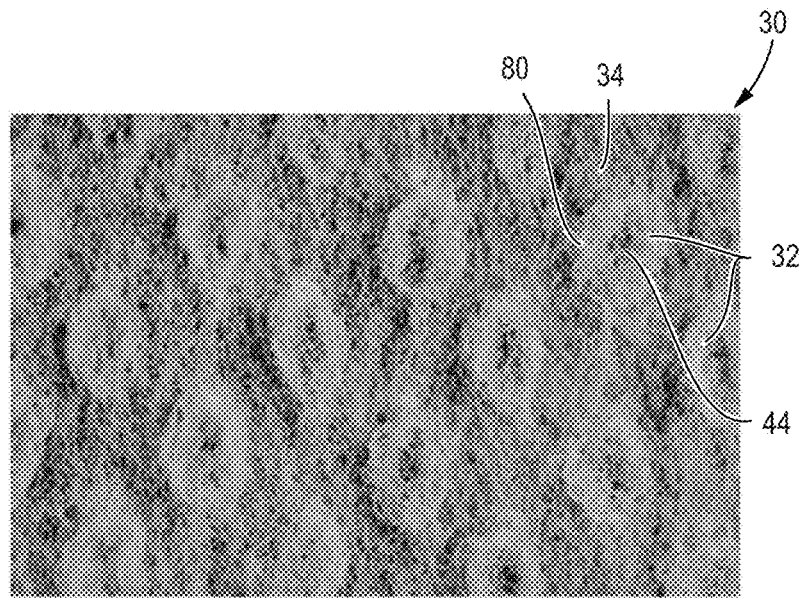
FIG. 9 is a plan view photomicrograph from the protrusion side of a material after it has been subjected to compression showing the high fiber concentration region around the perimeter of the protrusion.

The protrusions 32 may collapse in a controlled manner after compression to maintain the wide opening 44 at the base. FIG. 9 shows the first surface 34 of a nonwoven material 30 according to the present invention after it has been subjected to compression. FIG. 10A is a side view of a single downwardly-oriented protrusion 32 after it has been subjected to compression. As shown in FIG. 9, when the protrusions 32 have been compressed, there appears to be a higher concentration of fibers in the form of a ring of increased opacity 80 around the base opening 44. When a compressive force is applied to the nonwoven materials, the side walls 56 of the protrusions 32 may collapse in a more desirable/controlled manner such that the side walls 56 become concave and fold into regions of overlapping layers (such as into an s-shape/accordion-shape). The ring of increased opacity 80 represents folded layers of material. In other words, the protrusions 32 may have a degree of dimensional stability in the X-Y plane when a Z-direction force is applied to the protrusions. It is not necessary that the collapsed configuration of the protrusions 32 be symmetrical, only that the collapsed configuration prevent the protrusions 32 from flopping over or pushing back into the original plane of the nonwoven, and significantly reducing the size of the base opening (for example, by 50% or more). For example, as shown in FIG. 10A, the left side of the protrusion 32 can form a z-folded structure, and the right side of the protrusion does not, but still appears, when viewed from above, to have higher opacity due to a degree of overlapping of the material in the folded portion. Without wishing to be bound to any particular theory, it is believed that the wide base opening 44 and large cap 52 (greater than the width of the base opening 44), combined with the lack of a pivot point, causes the protrusions 32 to collapse in a controlled manner (prevents the protrusion 32 from flopping over). Thus, the protrusions 32 are free of a hinge structure that would otherwise permit them to fold to the side when compressed. The large cap 52 also prevents the protrusion 32 from pushing back into the original plane of the nonwoven.

The deformations can be disposed in any suitable density across the surface of the nonwoven material 30. The deformations may, for example, be present in a density of: from about 5 to about 100 deformations; alternatively from about 10 to about 50 deformations; alternatively from about 20 to about 40 deformations, in an area of 10 cm$^2$.

The deformations can be disposed in any suitable arrangement across the plane of the nonwoven material. Suitable arrangements include, but are not limited to: staggered arrangements, and zones.

Additionally, for those forms where the textured nonwoven web 30 forms a portion of a topsheet of a disposable absorbent article—such that the distal end 54 of the protrusions 32 form a portion of the wearer-facing surface of the article—appropriate density of protrusions 32 can allow for better acquisition speed of liquid insults. It is believed that where the protrusions 32 have the appropriate density, good acquisition speed of liquid insults can be achieved. In contrast, where the protrusions 32 have a high density, acquisition speed of liquid insults may be detrimentally impacted.

Moreover, the appropriate density of the protrusions 32 can vary depending upon the application of the textured nonwoven web 30. For example, in the context of baby diapers, the expected volume of liquid insult from a newborn may be very different from that of a child near the toilet training stage. Accordingly, the protrusions 32—when oriented toward the wearer—may have a first density in the absorbent article for the newborn and may be a second density in the absorbent article for the older child. The second density of the protrusions 32 may be less than the first density. Similarly, in the context of adult incontinence, the protrusions 32 may have a third density which is less than the second density and the first density. And, in the context of menstrual pads and/or sanitary napkins, the expected volume of liquid insults may be much less than that of any of the foregoing. In such cases the protrusions 32 may have a fourth density which is greater than the third density and may be greater than the second density. And, in some forms, may be greater than the first density.

Figure 24:
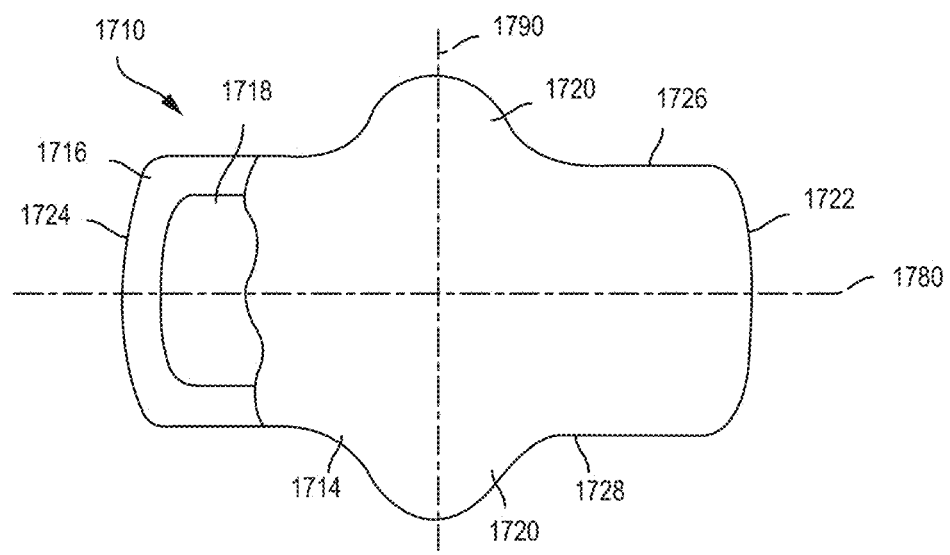
FIG. 24 is a top view of a feminine hygiene article, i.e. sanitary napkin, constructed in accordance with the present disclosure.
Figure 25:
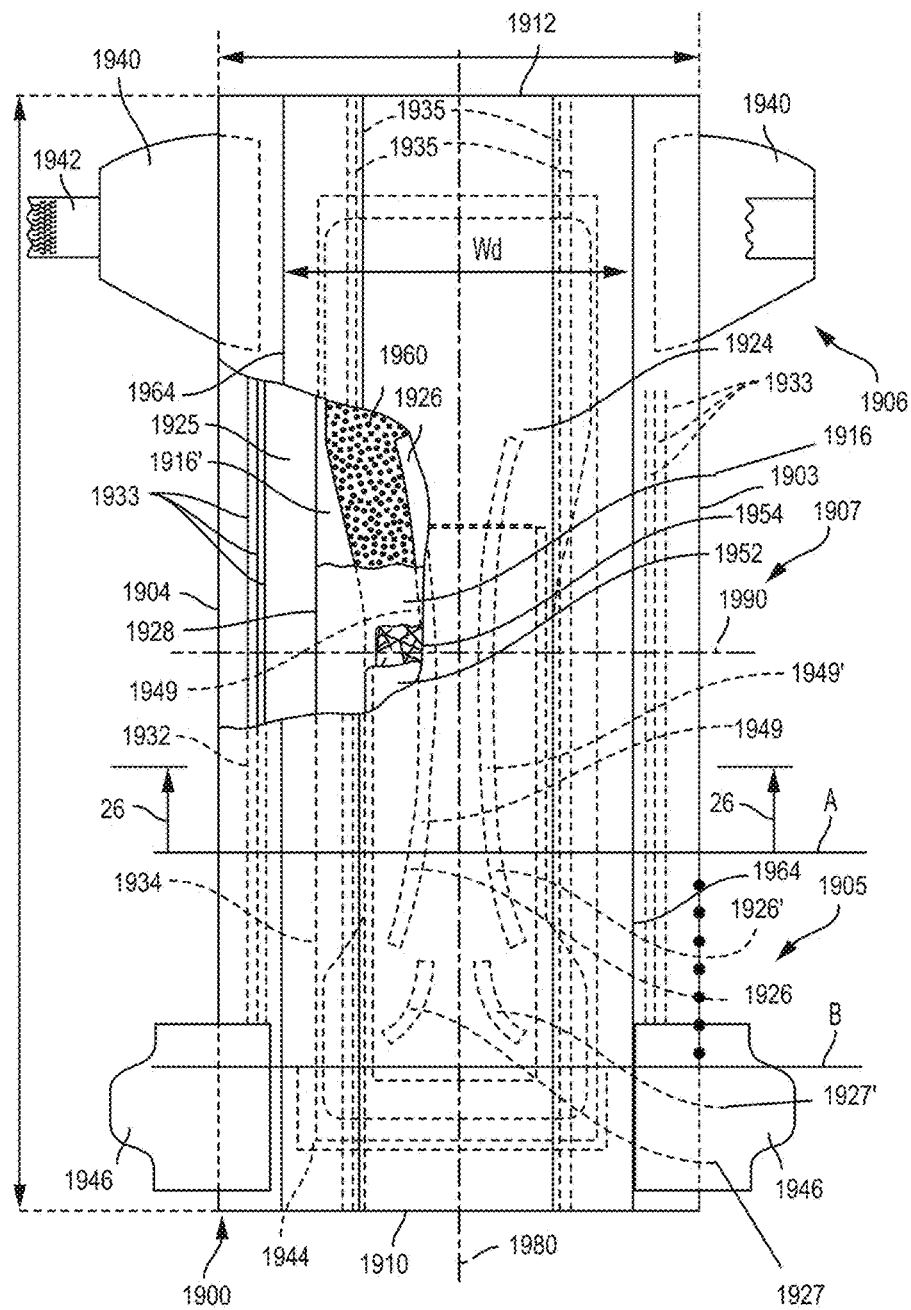
FIG. 25 is a top view of an absorbent article with some layers partially removed in accordance with the present disclosure.

The nonwoven webs 30 described herein can comprise any suitable component or components of an absorbent article. For example, the textured nonwoven webs can comprise the topsheet of an absorbent article as shown in FIGS. 24 and 25, or, if the nonwoven web 30 comprises more than one layer, the nonwoven web can comprise a combined topsheet 1714 or 1924 and acquisition layer of an absorbent article, such as a sanitary pad 1710 or diaper 1900. Each of the sanitary pad 1710 and diaper 1900 shown in FIGS. 24 and 25 may also comprises an absorbent core, a backsheet, and a distribution layer. Details regarding the sanitary pad 1710 and diaper 1900 are discussed further hereafter.

The textured nonwoven webs of the present disclosure may also form an outer cover of an absorbent article, such as backsheet. The textured nonwoven webs 30 can be placed in an absorbent article with the protrusions 32 in any suitable orientation. For example, the protrusions 32 can be oriented up or down. In other words, the protrusions 32 may be oriented toward the absorbent core. Thus, for example, it may be desirable for the protrusions 32 to point inward toward the absorbent core in a diaper and/or sanitary pad (that is, away from a body-facing side and toward the garment-facing side), or other absorbent article. For those forms of the present invention where the topsheet and the acquisition layer comprise protrusions facing toward the absorbent core, the acquisition layer may have lower fiber density in its distal end as compared to the fiber density of the undeformed region of the acquisition layer.

Alternatively, the protrusions 32 may be oriented so that they extend away from the absorbent core of the absorbent article. In still other forms, the nonwoven webs 30 can be made so that they have some protrusions 32 that are oriented upward, and some that are oriented downward. Without wishing to be bound to any particular theory, it is believed that such a structure may be useful in that the protrusions that are oriented upward can be more effective for cleaning the body from exudates, while the protrusions that are oriented downward can be more effective for absorption of exudates into the absorbent core. Therefore, without being bound to theory, a combination of these two protrusion orientations will offer advantage that the same product can fulfill the two functions.

As noted previously, the textured nonwoven webs 30 of the present invention may comprise two or more layer nonwoven structure. Such structures may provide fluid handling benefits. For example, if the layers are integrated together, and the protrusions 32 are oriented toward the absorbent core, they may also provide a dryness benefit. It may be desirable, on the other hand, for the protrusions 32 to point outward, away from the absorbent core in a pad for a wet or dry mop to provide a cleaning benefit. In some embodiments, when the nonwoven web 30 is incorporated into an absorbent article, the underlying layers can be either substantially, or completely free, of tow fibers. Suitable underlying layers that are free of tow fibers may, for example, comprise a layer or patch of cross-linked cellulose fibers. In some cases, it may be desirable that the nonwoven material 30 is not entangled with (that is, is free from entanglement with) another web.

Composition Sites

As mentioned previously, textured nonwoven webs of the present invention may comprise composition(s) disposed in a plurality of composition sites and/or in a pattern. Forms of the present invention are contemplated where textured webs of the present invention comprise a first plurality of composition sites and a second plurality of composition sites, wherein the first plurality of composition sites comprise a first composition and the second plurality of composition sites comprise a second composition. For example, the first composition may be more hydrophilic than the second composition. As another example, the first composition may be more hydrophobic than the second composition—specific examples of hydrophilic and/or hydrophobic composition sites are discussed herein. And, forms of the present invention are contemplated where textured nonwoven webs may comprise the first plurality of composition sites sans the second plurality of composition sites or vice versa. As noted herein, a third plurality of composition sites may be applied to a web in some forms. The third plurality of composition sites may be in addition to or sans the first plurality of composition sites and/or the second plurality of composition sites. Additional composition sites may be provided on the textured nonwoven webs of the present invention.

As shown in FIGS. 17A-18B the composition sites described herein may be applied to the textured nonwoven web in an array of discrete sites as a plurality of interconnected sites. Forms of the present invention are contemplated where the composition sites applied to the textured nonwoven web may be in the form of a plurality of stripes. And, while the plurality of stripes may be discrete from one another, forms are contemplated where the plurality of stripes are, at least in part, interconnected with one another. In such forms, each of the plurality of stripes may be registered with protrusions 32.

Regarding FIGS. 17A-18B, in some forms, the textured nonwoven web 30 may comprise the protrusions 32 as described heretofore and a plurality of first composition sites 135 comprising a first composition. The depictions of the first composition sites 135 have been exaggerated in FIGS. 18A and 18B for ease of explanation. The first composition sites 135 may be disposed on the distal end 54 of the protrusion 32 and a portion of the sidewalls 56. In some forms, the first composition site 135 may be disposed on the cap 52 of the protrusion 32. Forms of the present invention are contemplated where the first composition site 135 is disposed only on the sidewalls 56 or only on the distal ends 54 of the protrusions 32. Additionally, forms of the present invention are contemplated where less than 100 percent of the protrusions 32 comprise the first composition site 135. For example, in some forms, less than 90 percent, less than 80 percent, less than 70 percent, less than 60 percent, less than 50 percent, less than 40 percent, less than 30 percent of the protrusions have a corresponding first composition site 135, specifically reciting all values within these ranges and any ranges created thereby.

Additionally, in some forms, the textured nonwoven webs 30 of the present invention may further comprise a plurality of second composition sites 137. As shown, the plurality of second composition sites 137 may be disposed in the first region 40 of the textured nonwoven web 30. And, in some forms, as shown in FIG. 18A, the second plurality of composition sites 137 may be disposed on the first surface 34 of the textured nonwoven web 30. Similar to the above, the depictions of the second composition sites 137 in FIGS. 18A and 18B have been exaggerated for ease of explanation.

Figure 17A:
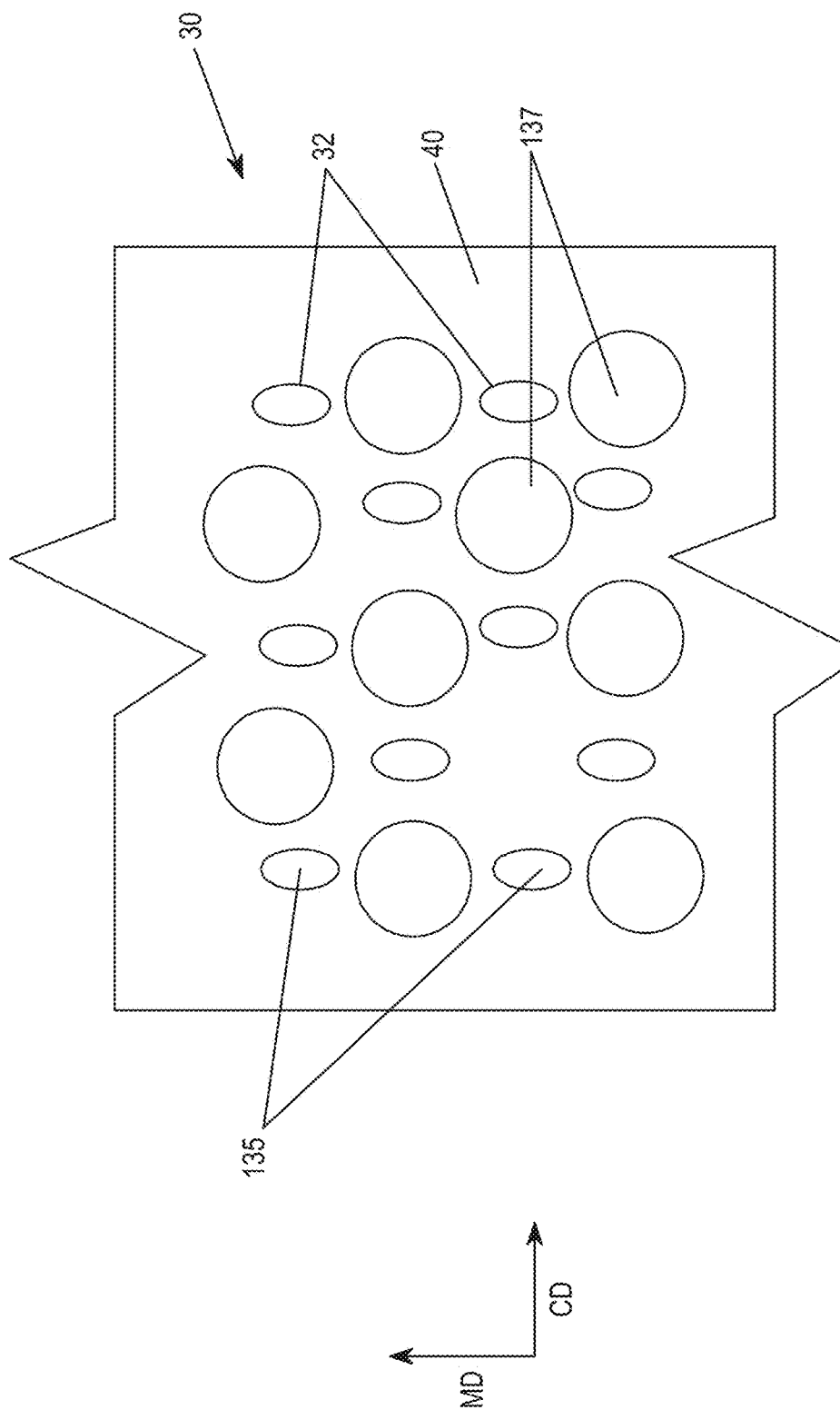
FIG. 17A is a schematic plan view showing an exemplary textured nonwoven web in accordance with the present disclosure.
Figure 17B:
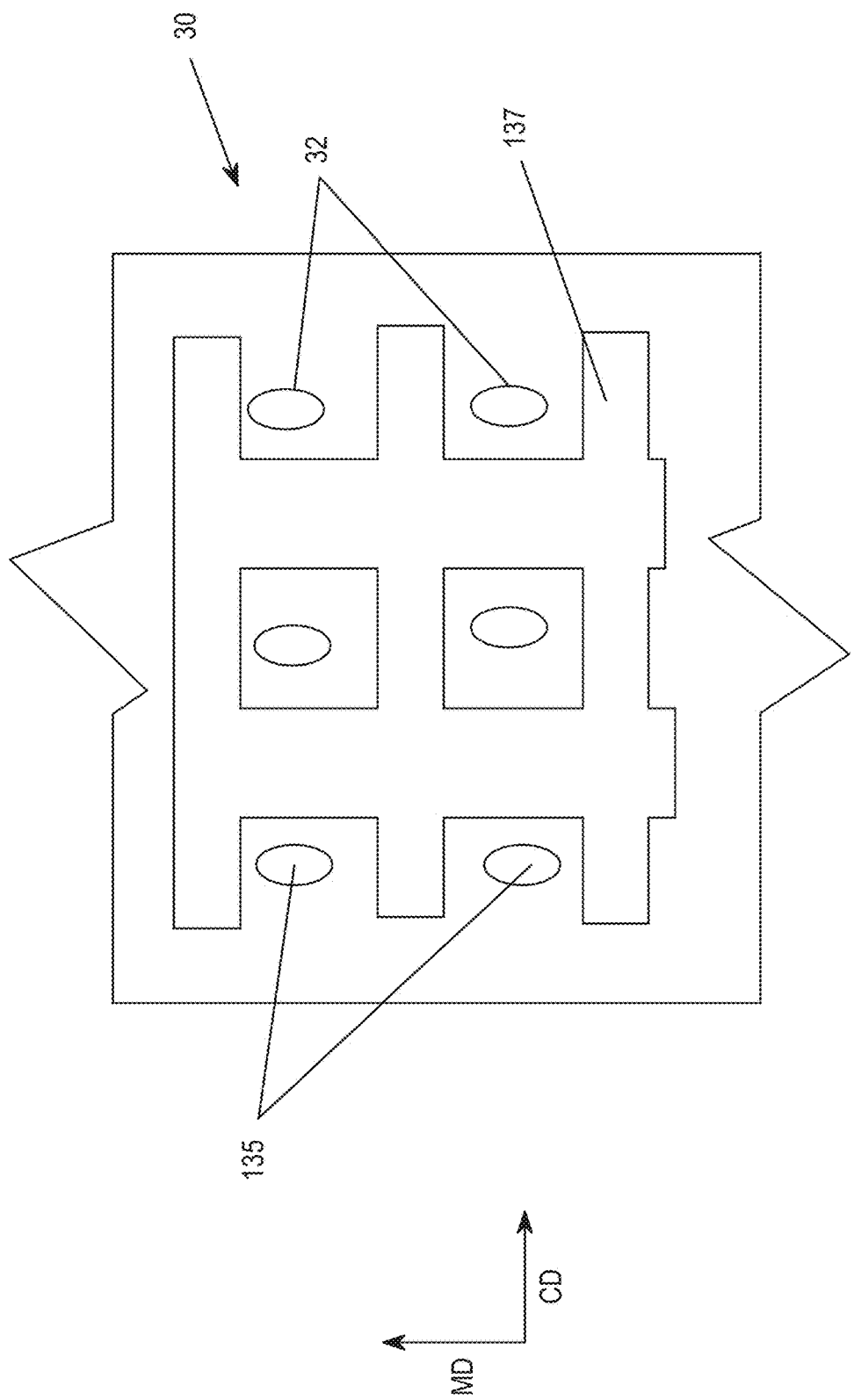
FIG. 17B is a schematic plan view showing another exemplary textured nonwoven web in accordance with the present disclosure.

Regarding FIGS. 17A, 17B, and 18A, in some forms of the present invention, the second plurality of composition sites 137 may be discrete areas of composition deposition. In other forms, as shown with regard to FIG. 17B, the second plurality of composition sites 137 may interconnect to form a grid like pattern which surrounds at least a portion of the protrusions 32 in the textured nonwoven web 30.

In such forms, the first composition site 135 may comprise a hydrophobic composition while the second composition site 137 comprises a hydrophilic composition. In some forms, the first composition may be more hydrophobic than the second composition. And, the first composition may be more hydrophobic than the constituent chemistry of the plurality of fibers of the textured nonwoven web 30. Similarly, the second composition may be more hydrophilic than the constituent chemistry of the plurality of fibers of the textured nonwoven web 30. And for those forms where the textured nonwoven web 30 comprises the first layer 30A and the second layer 30B (shown in FIGS. 11A-11F), the first composition may be more hydrophobic than at least the plurality of fibers of the first layer 30A and/or the second layer 30B. Similarly, the second composition may be more hydrophilic than at least the plurality of fibers of the first layer 30A and/or the second layer 30B.

Additionally, forms of the present invention are contemplated where the first plurality of composition sites 135 are provided sans the second plurality of composition sites 137. In such configurations, the first composition may be more hydrophobic than the constituent chemistry of the plurality of fibers of the textured nonwoven web 30. And, in such configurations, the plurality of fibers of the textured nonwoven web 30 may comprise hydrophilic fibers. Other forms are contemplated where the second plurality of composition sites 137 are provided sans the first plurality of composition sites. In such forms, second composition may be more hydrophilic than the constituent chemistry of the plurality of fibers of the textured nonwoven web 30. And, in such configurations, the plurality of fibers of the textured nonwoven web may comprise hydrophobic fibers.

Referring to FIG. 18A, in such forms, the application of a hydrophobic composition onto the distal ends 54 of the textured nonwoven webs 30 can be beneficial, particularly in the absorbent article context. Where the textured nonwoven webs 30 of the present invention form a portion of a topsheet of an absorbent article—such that the distal ends 54 of the protrusions 32 are oriented away from an absorbent core—the first plurality of composition sites 135 can provide improved dryness to the wearer of the absorbent article. And, because the protrusions are discrete and spaced apart to some extent, this can allow for sufficient fluid acquisition by the textured nonwoven webs 30. And, as noted above, the first surface 34 in the first region 40 may comprise a hydrophilic composition. This additional composition can further improve fluid acquisition time. Additionally, within this configuration, the first plurality of composition sites 135 may comprise a skin care benefit agent. In such forms, the distal ends 54 of the protrusions 32 would be in contact with the skin of the wearer and could provide effective transfer of the skin care benefit agent. And in such configurations, the skin care benefit agent may be distanced to some extent from the absorbent core which can reduce the likelihood of contamination of the absorbent core by the skin care benefit agent. Additionally, in such configurations, the hydrophobic composition can reduce the amount of urine/menses which can be trapped in interfiber regions of the protrusion 32. This is particularly beneficial where the fibers of the protrusion 32 are hydrophilic.

Regarding FIG. 18B, the textured nonwoven webs 30 of the present invention may comprise protrusions 32 which extend in the negative Z-direction (subjacent to the first surface 34 of the textured web 30). In such forms, if the textured nonwoven web 30 were utilized as a topsheet of a disposable absorbent article, the distal ends 54 of the protrusions 32 would be oriented toward the absorbent core. Similar to the configuration shown in FIG. 18A, the first composition site 135 may be disposed on the protrusion 32 as described heretofore with regard to FIG. 18A. Additionally, the textured nonwoven web 30 may comprise a plurality of second composition sites 137 as described heretofore with regard to FIGS. 17A and 17B. However, in contrast to the depiction of FIG. 18A, the second composition may be disposed adjacent the opening 44 as opposed to the protrusion 32. In such forms, the first composition of the first composition sites 135 may be hydrophilic and the second composition of the second composition sites 137 may be hydrophobic. In some forms, the first composition may be more hydrophilic than the second composition. And, the first composition may be more hydrophilic than the constituent chemistry of the plurality of fibers of the textured nonwoven web 30. Similarly, the second composition may be more hydrophobic than the constituent chemistry of the plurality of fibers of the textured nonwoven web 30. And for those forms where the textured nonwoven web 30 comprises the first layer 30A and the second layer 30B (shown in FIGS. 11A-11F), the first composition may be more hydrophilic than at least the plurality of fibers of the first layer 30A and/or the second layer 30B. Similarly, the second composition may be more hydrophobic than at least the plurality of fibers of the first layer 30A and/or the second layer 30B.

Additionally, forms of the present invention are contemplated where the first plurality of composition sites are provided sans the second plurality of composition sites. In such configurations, the first composition may be more hydrophilic than the constituent chemistry of the plurality of fibers of the textured nonwoven web 30. And, in such configurations, the plurality of fibers of the textured nonwoven web 30 may comprise hydrophobic fibers. In such forms, particularly where the textured nonwoven web 30 is being utilized as a topsheet—such that the distal ends 54 of the protrusions 32 are oriented toward the absorbent core—the hydrophobic fibers of the textured nonwoven web 30 can provide a clean dry surface which can increase the comfort to the wearer of the absorbent article. And, the provision of the hydrophilic composition on the distal ends 54 and/or sidewalls 56 can provide for good liquid acquisition by the topsheet.

Other forms are contemplated where the second plurality of composition sites are provided sans the first plurality of composition sites. In such forms, the second composition may be more hydrophobic than the constituent chemistry of the plurality of fibers of the textured nonwoven web 30. And, in such configurations, the plurality of fibers of the textured nonwoven web may comprise hydrophilic fibers. In such forms of the present invention where the textured nonwoven web 30 forms a portion of a topsheet of an absorbent article—such that the protrusions 32 are oriented toward an absorbent core—the plurality of second composition sites 137 can improve the dryness of the topsheet which in turn can provide additional comfort to a wearer of the absorbent article. And, for those forms, where the protrusions are formed in the topsheet and in the acquisition layer, the provision of the plurality of second composition sites 137 and low density regions of the protrusions 32 in the acquisition layer can allow for good fluid acquisition. Also, in some forms, as noted herein, the plurality of second composition sites 137 may comprise a skin care benefit composition. In such forms, the plurality of second composition sites 137 may provide for more effective transfer to the skin of the wearer of the absorbent article.

With regard to FIGS. 17A-18B, for those forms of the present invention where the textured nonwoven web 30 comprises a plurality of layers, the first composition sites may be disposed on a portion of the distal ends of the primary protrusion which forms the outermost facing surface of the protrusion with respect to either the positive Z or negative Z-direction. Regardless of whether the textured nonwoven web 30 comprises layers, in some forms, it may be beneficial for composition to be provided to an interior surface of the protrusion 32 and/or an exterior surface of the protrusion 32. For example, in some forms, the first plurality of composition sites 135 may be disposed on an outer surface 54B of the distal ends 54 and/or on the outer surface 56B of the sidewalls 56. Such forms may be beneficial where the textured nonwoven web 30 forms a portion of a topsheet of a disposable absorbent article—with the distal ends 54 forming a portion of a wearer-facing surface of the disposable absorbent article—in that a hydrophobic composition on the outer surface 54B and/or 56B can ensure a clean dry surface for a wearer. In contrast, if the hydrophobic composition were instead disposed on an inner surface 54A and/or 56A, the hydrophobic composition may actually retain liquid insults in the distal end 54 and sidewalls 56 of the protrusion 32. This aspect may be particularly relevant where the constituent chemistry of the fibers of the textured nonwoven web 30 is hydrophilic.

Additional forms are contemplated where the first composition is disposed on the inner surface 56A of the sidewalls and/or inner surface 54A of the distal end. Such forms may be beneficial where the textured nonwoven web 30 forms a portion of a topsheet of a disposable absorbent article—with the distal ends 54 oriented toward an absorbent core of the disposable absorbent article—in that a hydrophilic composition on the inner surface 54A and/or 56A can improve acquisition speeds of liquid insults. In contrast, if the hydrophilic composition were instead disposed on an outer surface 54B and/or 56B, liquid insults may not have easy access to the hydrophilic composition which may negatively impact liquid acquisition speeds of the topsheet. This aspect may be particularly relevant where the constituent chemistry of the fibers of the textured nonwoven web 30 is hydrophobic.

In some forms, the composition disposed on the inner surface 56A of the sidewalls 56 and/or inner surface 54A of the distal end 54 may be a third composition, wherein the third composition is different than the first composition and/or second composition. Application of compositions to the inner surfaces of the protrusions 32 may be achieved via non-contact printing which is described hereafter. Additionally, methods of manufacturing the above configuration are also provided hereafter.

Additionally, forms of the present invention are contemplated where the textured nonwoven web 30 comprises multiple nonwoven strata. Nonwoven strata are spunbond nonwoven substrates which are produced by a spinbeam. For example, the textured nonwoven web may comprise a plurality of nonwoven strata formed from a first spinbeam and a second spinbeam. The first spinbeam may deposit a first plurality of continuous filaments onto a belt thereby forming a first nonwoven strata. A second spinbeam may deposit a second plurality of continuous filaments onto the belt over the top of the first plurality of continuous filaments. The second plurality of continuous filaments form a second nonwoven strata. Additional forms of the present invention are contemplated where additional spinbeams are provided to provide additional continuous filaments/nonwoven strata. Accordingly, the textured nonwoven web 30 of the present invention may comprise a third strata a fourth strata and so on. And, in some forms, the strata of the textured nonwoven web 30 may be configured such that at least two of the strata are different.

The first composition sites, second composition sites, and/or any additional composition sites of the textured web of the present invention may comprise any suitable shape. Some suitable examples include circles, squares, clovers, rainbows, letters, numbers, symbols, animals, etc. Other suitable shapes include, triangles, ovals, ellipses, stars, flowers, diamonds, hearts, trapezoids, toroid, the like, and/or combinations thereof. In some forms of the present invention, the composition sites may comprise outlines of shapes. For example, at least some of the compositions sites may comprise the outline of a star. As another example, the composition sites may comprise a star that is filled. These examples are applicable to any shape that is contemplated for the compositions sites. Additionally, the first composition sites, second composition sites, and/or additional composition sites may be applied to the textured nonwoven web in any suitable pattern to increase aesthetic appeal to a user. Some suitable compositions are discussed hereafter.

Referring back to FIGS. 1-8, the protrusions 32 of the present disclosure may have zones of variable fiber density. For example, in the first region, the fiber density may be higher than the fiber density in the sidewalls 56. And, as noted previously, the nonwoven materials of the present invention may comprise a composition or a plurality thereof. Due to the increased density in the first region (the undeformed areas of the textured nonwoven web) an increased amount of composition may be provided to the first region as opposed to the sidewalls 56 which comprise a lower fiber density. Composition deposition is discussed in additional detail hereafter.

Methods of Making the Textured Nonwoven Webs

The textured nonwoven web 30 comprising the generally planar first region 40 and the plurality of discrete integral second regions 42 that comprise deformations comprising protrusions 32 extending outward from the first surface 34 of the textured nonwoven webs 30 and openings in the second surface 36 can be formed according to the processes described in U.S. Patent Application Publication No. 2016/0074256 (Of course, forms of the present invention are contemplated where the protrusions will extend outward from the second surface 36 of the textured nonwoven web 30 and the openings will be formed in the first surface 34 of the textured nonwoven web 30.) In general, a precursor web is supplied to a mechanical deformation process which forms the protrusions 32.

Non-Contact Printing of Compositions

One suitable method by which compositions may be deposited on textured nonwoven webs 30 of the present invention is via non-contact printing. In some forms, as disclosed with regard to FIG. 19A, the compositions may be deposited on the textured nonwoven web 30 post formation of the protrusions 32 (shown in FIGS. 1-8). In other forms, as disclosed with regard to FIGS. 20A, 21B, and 23, composition(s) may be deposited on the precursor web prior to formation of the protrusions 32 (shown in FIGS. 1-8). We begin though with a discussion of composition deposition—post protrusion formation.

Figure 19A:
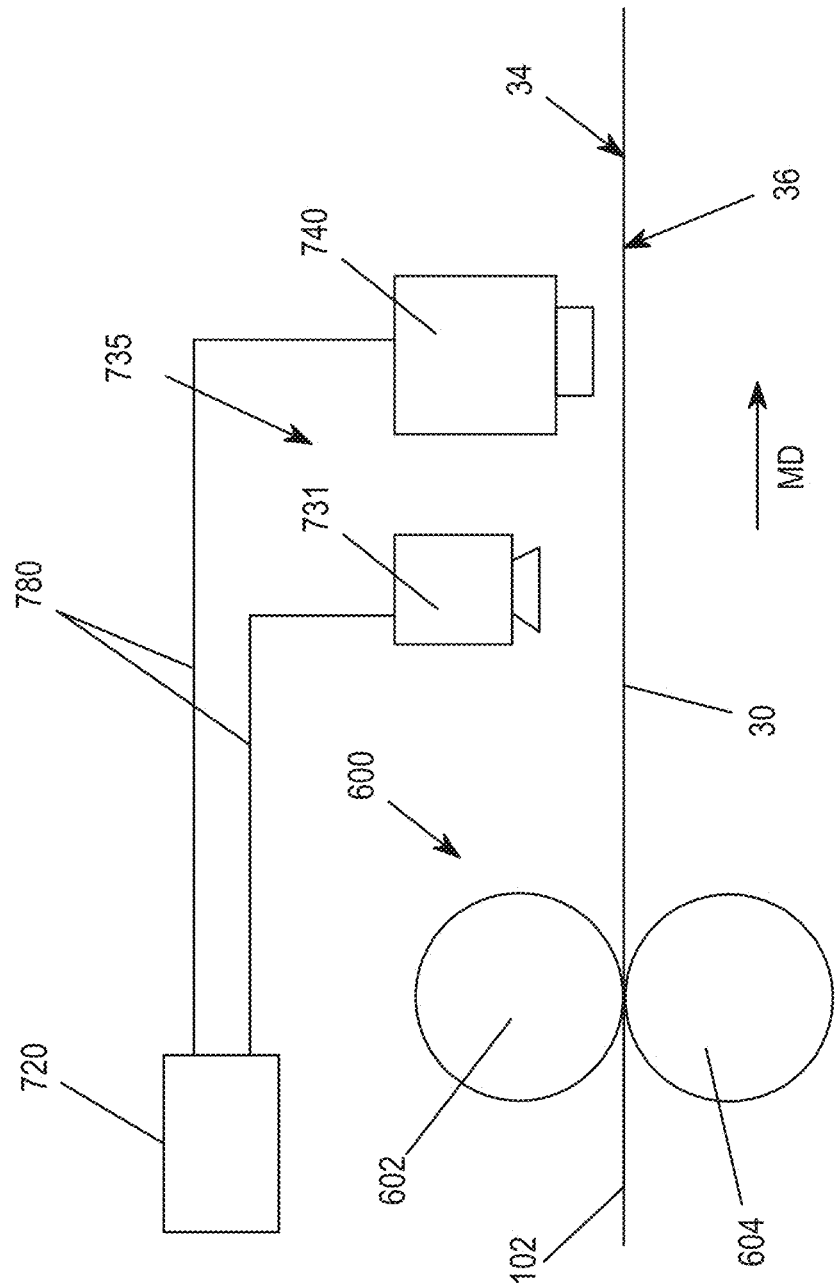
FIG. 19A is a schematic diagram showing an exemplary process for printing compositions on the textured nonwoven webs in accordance with the present disclosure.

FIG. 19A depicts an exemplary process for non-contact printing of compositions on the textured webs 30 of the present invention. The process shown in FIG. 19A allows for the deposition of one or more composition sites post formation of the protrusions 32 (shown in FIG. 1) in the textured nonwoven web 30. As shown, in some forms of the present invention, the precursor web 102 may be provided to the apparatus 600 as described heretofore.

Figure 19B:
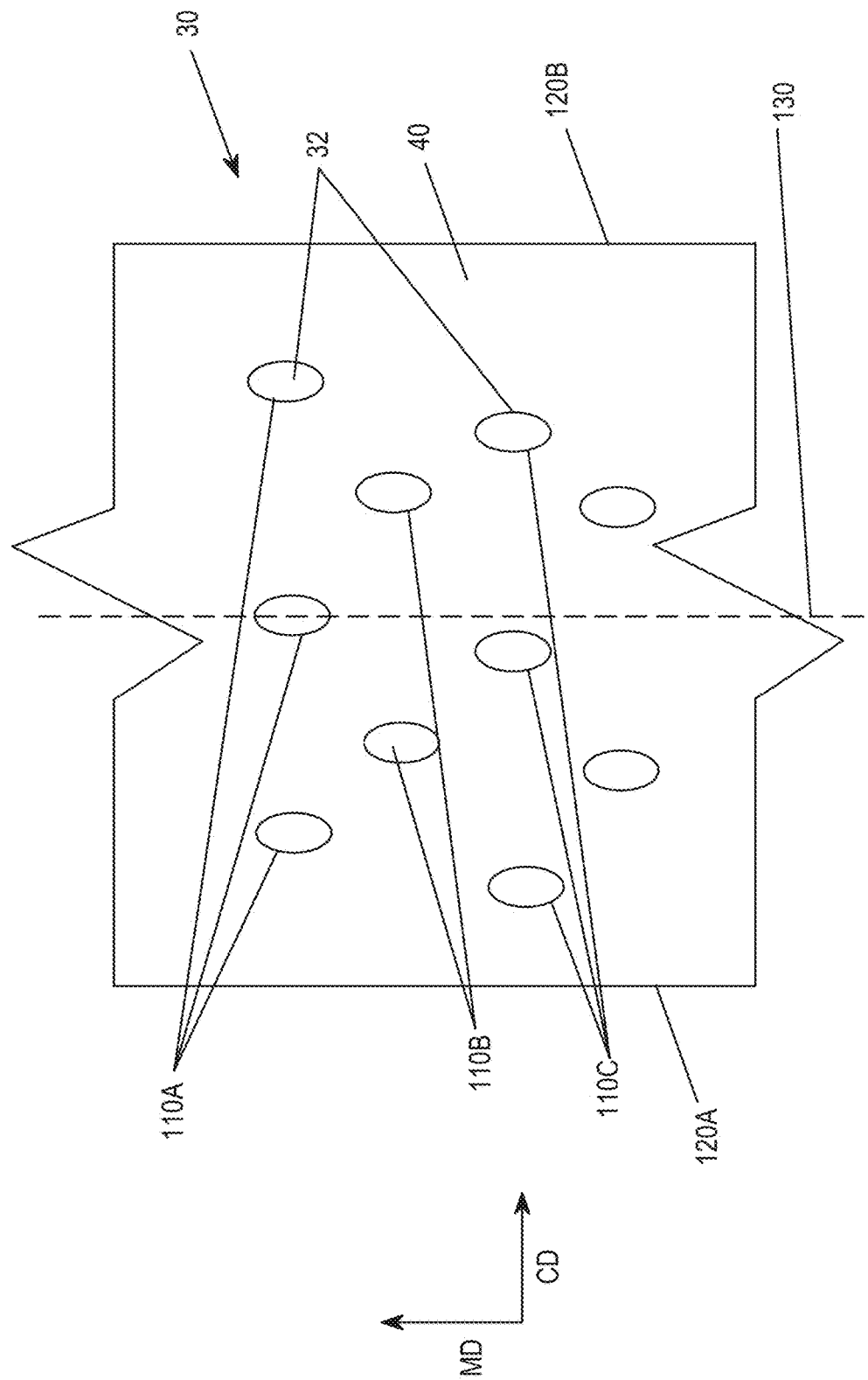
FIG. 19B is a schematic representation of a textured nonwoven web in accordance with the present disclosure.

Referring to FIGS. 19A and 19B, a precursor web 102 may be supplied to a mechanical deformation apparatus 600 which produces the protrusions on the precursor web 102. Downstream of the apparatus 600, the precursor web 102 becomes the textured nonwoven web 30. The textured nonwoven web 30 may comprise the protrusions 32 arranged in a plurality of groups, 110A, 110B, and 110C, etc. As shown, the textured nonwoven web 30 may comprise side edges 120A and 120B each of which extend generally parallel to the MD. As shown, the protrusions 32 may comprise a phase shift with respect to a machine centerline 130. For example, the protrusions 32 comprised by a first group 110A may be positioned at a phase shift of zero degrees. This means that the protrusions 32 are positioned where they were intended to be with respect to the textured nonwoven web 30. However, due to web tracking in the CD the protrusions 32 can be offset to some extent. For example, the protrusions 32 comprised by a second group 110B may comprise a phase shift of positive 15 degrees as the protrusions 32 are shifted slightly to the left of the machine centerline 130. As another example, the protrusions 32 comprised by a third group 110C may comprise a phase shift of positive 30 degrees as the protrusions 32 are shifted to the left of the machine centerline 130 to a greater extent than the protrusions 32 of the second group 110B. The phase shift may comprise a negative value as well. For example, where the protrusions 32 are shifted to the right of the machine centerline 130, these protrusions 32 would comprise a negative phase shift, e.g. negative 15 degrees.

It is worth noting that the machine centerline 130 is a fixed reference. The protrusions 32 described herein are not required to straddle the machine centerline 130. For example, the protrusions 32 may be—by design—spaced from the machine centerline 130. In such cases, the can be evaluated as described herein regarding their predetermined location from the machine centerline 130. Any offset from the predetermined location would be evaluated as a phase shift of greater than or less than zero.

Still referring to FIGS. 19A and 19B, the textured nonwoven web 30 may pass through an inspection/print station 735. As shown, inspection/print station 735 may comprise a camera 731 which is in signal communication 780 with a computational device 720 and a printer 740 in signal communication with the computational device 720. An image captured by the camera 731 can vary. For example, the camera 731 can capture an image of the first group 110A of protrusions 32. As another example, the camera 731 can capture an image(s) of the first group 110A, the second group 110B, and/or third group 110C of protrusions 32. In some forms, the camera 731 may capture an image of at least a portion of the first group 110A, second group 110B and/or third group 110C of protrusions 32.

The camera 731 may transmit the image of the first group 110A, the second group 110B and/or the third group 110C, or at least a portion(s) thereof, to the computational device 720. The computational device 720 analyzes the transmitted image or images provided by the camera 731 to detect the protrusions 32 of the submitted image(s) and determine the phase shift of the first group 110A, the second group 110B, and/or the third group 110C of protrusions 32. The determination of phase shift is discussed hereafter.

After the determination of the phase shift of the first group 110A, second group 110B and/or third group 110C, the computational device 720 may compare the determined phase shift to a plurality of stored pre-rendered patterns. For example, in some forms of the present invention, the computational device 720 may comprise a stored pattern for a positive 15 degree phase shift, a negative 15 degree phase shift, a positive 30 degree phase shift, a negative 30 degree phase shift, a positive 45 degree phase shift, a negative 45 degree phase shift, a positive 60 degree phase shift, a negative 60 degree phase shift, a positive 75 degree phase shift, a negative 75 degree phase shift, a positive 90 degree phase shift, a negative 90 degree phase shift, and so on up to 180 degrees (positive and negative). The phase shift increments described above may be increased or reduced. For example, the computational device 720 may comprise stored patterns corresponding to phase shifts of 12 degrees, 13 degrees, 14 degrees, etc. This may ensure that the tolerance of the printed composition associated with the protrusions 32 and or first region 40 is relatively high. In another example, the increment between adjacent phase shift patterns may be increased, e.g. phase shift of 15 degrees, 30 degrees, 45 degrees, etc.

The computational device 720 may then choose which of the stored patterns most closely correlates to the determined phase shift of the first group 110A, second group 110B, and/or third group 110C. The computational device 720 may then provide the chosen stored pattern to the printer 740 for the first group 110A, second group 110B, and/or third group 110C such that composition could be applied to the textured nonwoven web 30. Where the determined phase shift falls between stored patterns, e.g. a phase shift of positive 20 degrees, the computational device 720 may provide the printer 740 with the stored pattern which most closely correlates to the determined phase shift, e.g. positive 15 degrees versus positive 30 degrees.

Accordingly, in some forms, the printer 740 may deposit a first plurality of composition sites according to a first stored pre-rendered pattern. The first plurality of composition sites may be based upon the determined phase shift of the first group 110A of protrusions 32. The printer 740 may also deposit a second plurality of composition sites according to a second stored pre-rendered pattern. The second plurality of composition sites may be based upon the determined phase shift of the second group 110B of protrusions 32. In some forms, the first stored pre-rendered pattern may be different than the second stored pre-rendered pattern. Additionally, the printer 740 may also deposit a third plurality of composition sites according to a third stored pre-rendered pattern. The third plurality of composition sites may be based upon the determined phase shift of the third group 110C of protrusions 32. In some forms, the first stored, pre-rendered pattern, the second stored, pre-rendered pattern, and/or the third stored, pre-rendered pattern may be different.

In some forms, the stored pre-rendered patterns may provide one or more compositions sites which are registered with the protrusions 32. In some forms, the pre-rendered patterns may provide one or more composition sites which are offset from the protrusions 32. In some forms, the stored pre-rendered patterns may provide one or more composition sites which partially overlap protrusions 32. In some forms, a combination of configurations may be provided to the composition sites. For example, a stored pre-rendered pattern may provide a first composition site registered with the protrusions 32 while a second composition site is offset from the protrusions 32, and/or while a third composition site partially overlaps protrusions 32. In addition to the foregoing or independent therefrom, in some forms, the stored pre-rendered patterns may provide one or more composition sites which are disposed between adjacent groups of protrusions 32. The inspection/print station 735 may similarly analyze the second surface 36 of the textured nonwoven web 30 and determine the phase shift of the openings 44 (shown in FIG. 2) as described above.

The inspection/print station 735 may be provided in a variety of configurations. For example, the camera 731 may be positioned downstream of the printer 740. In such arrangements, the camera 731 may capture an image or images of the textured nonwoven web 30 with the composition disposed thereon. The image or images may be provided to the computational device 720 to analyze whether the composition sites are phase shifted to the same or close to the same extent as the protrusions 32. Utilizing the image or images from the camera 731, the computational device 720 could adjust any discrepancy between the phase shift of the protrusions 32 and the phase shift of the composition sites deposited on the textured nonwoven web 30. In such configurations however, detecting the composition on the textured nonwoven web 30 may require special lighting or excitation devices such that the composition can be highlighted in the image or images provided to the computational device 720. The inspection/print station 735 is discussed further hereafter.

In some forms, the protrusions 32 in the image(s) may be dilated and/or eroded to ensure adequate application of the composition sites. For example, the protrusions 32 of an image may be dilated by plus 1 mm such that the composition sites are plus 1 mm larger in all dimensions than the protrusions 32. The dilation can be any suitable adjustment. For example, the dilation can be in the range of plus 1 mm, 2 mm, 3 mm, 4 mm, 5 mm, 6 mm, 7 mm, 8 mm, 9 mm, specifically reciting all values within these ranges and any ranges formed thereby.

In some forms of the present invention, the camera 731 may provide images directly to the printer 740. For example, as noted previously, the camera 731 may capture an image or image(s) with respect to the protrusions 32. The camera 731 may then provide the image(s) directly to the printer 740 as a print file. The printer 740 may then apply compositions to the web in accordance with the image(s) provided by the camera 731. In such forms, there may be no need to have stored pre-rendered patterns for comparison.

Figure 20C:
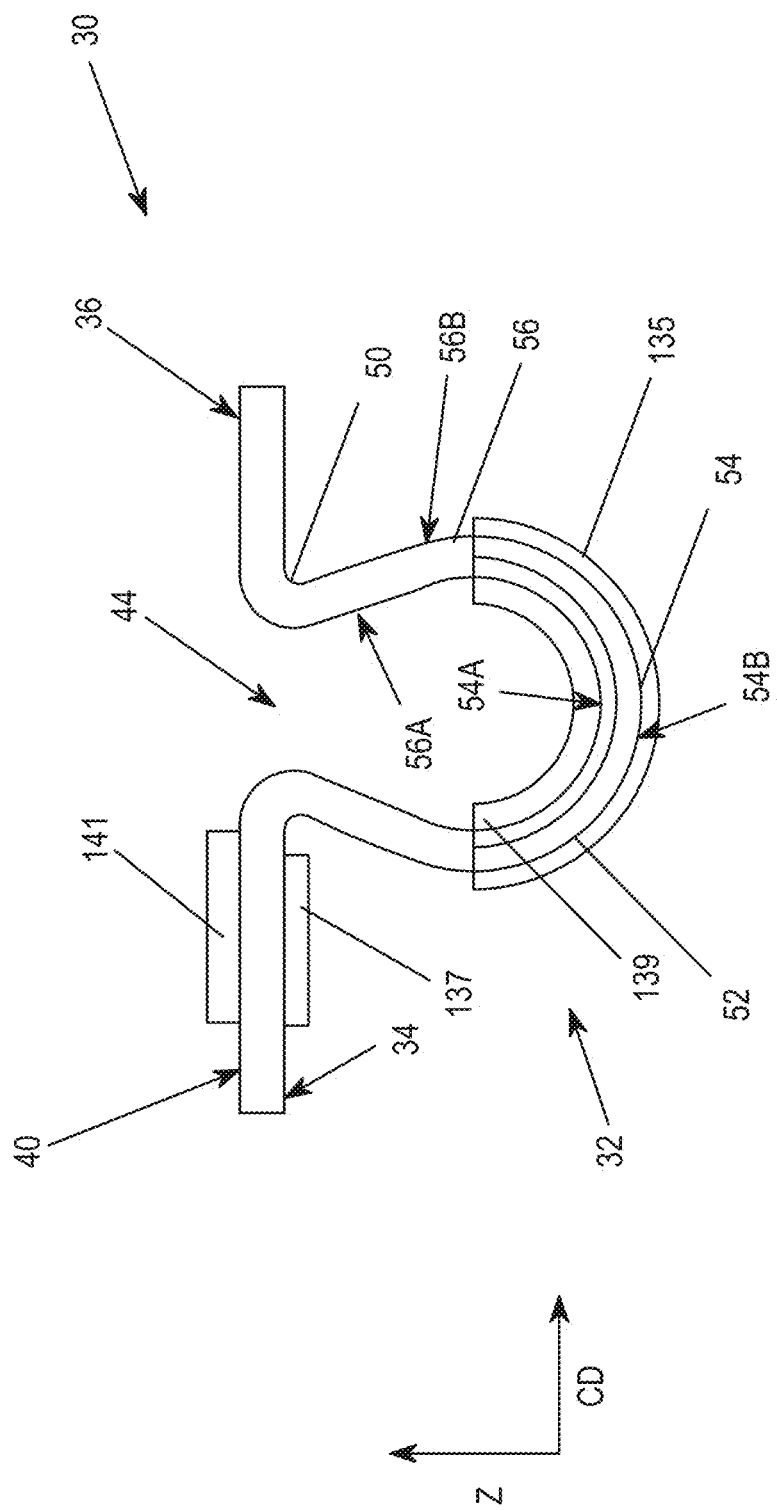
FIG. 20C is a schematic cross section of another exemplary textured nonwoven web comprising a plurality of composition sites.

Referring to FIGS. 20A-20C, as noted previously, in some forms of the present invention, one or more composition sites may be provided to the precursor web 102 prior to the formation of the protrusions 32. For example, the printer 740 may deposit one or more composition sites onto the first surface 34 of the precursor web 102. The camera 731 may provide an image or images to the computational device 720. The computational device 720 in such forms, may provide feedback to the apparatus 600 either advancing or retarding its timing based upon detected positions of the plurality of composition sites.

The resulting textured nonwoven web 30 may comprise one or more composition sites which correspond to one or more protrusions 32. For example, the one or more composition sites may be registered with the one or more protrusions 32. As another example, the one or more composition sites may be offset with respect to the one or more protrusions 32. Yet another example, the one or more composition sites may partially overlap the one or more protrusions 32. In some forms, the textured nonwoven web 30 may comprise a plurality of composition sites where at least some of the plurality of compositions sites are (i) registered with the one or more protrusions 32; (ii) offset with the one or more protrusions 32; and/or (iii) partially overlap the one or more protrusions 32.

In other forms, the camera 731 may be disposed downstream of the apparatus 600. In such forms, the computational device 720 may be in signal communication with the printer 740 and/or the apparatus 600. The computational device 720 may advance and/or retard the printer 740 and/or the apparatus 600. Additionally, the computational device 720 may also adjust the print pattern based upon the image(s) provided by the camera 731. In such forms, the image(s) provided by the camera 731 may also be utilized by the computational device 720 to determine any offset with the protrusions 32 and/or the plurality of composition sites in the MD direction.

Still referring to FIGS. 20A-20C, a second printer 742 may be provided in some forms of the present invention. The second printer 742 may be utilized to provide composition to the second surface 36 of the precursor web 102. With the addition of the second printer 742, composition may be applied to inner surfaces of the protrusion 32. As shown with regard to FIG. 20B, a third plurality of composition sites 139 may be provided to the inner surface 54A of the distal end and/or the inner surface 56A of the sidewall 56. The depiction of the third composition site 139 has been exaggerated for ease of explanation. Additionally, in some forms, a fourth plurality of composition sites 141 may be provided to the textured nonwoven web 30. As shown the fourth plurality of composition sites 141 may be disposed adjacent the openings 44 in the second surface 36 of the textured nonwoven web 30. As shown in FIG. 20C, the protrusion 32 is oriented in the negative Z-direction.

Although not shown, the second printer 742 may be in signal communication with a second controller. The second controller may receive input from the camera 731. Alternatively, the second controller may receive input from the controller 720 and base print instructions to the second printer 742 on the print instructions provided to the printer 740. Still in other forms of the present invention, the controller 720 may be utilized to control both the printer 740 and the second printer 742.

Other forms of the present invention are contemplated where the second printer 742 applies composition to the second surface 36 of the precursor web 102 in the absence of the first printer 740. In such forms, the composition may be disposed on the inner surface of the protrusions 32, e.g. inner surface 54A of the distal end 54 and/or inner surface 56A of the sidewalls 56.

With the utilization of non-contact printing, very sophisticated composition applications may be created. For example, as noted previously, composition may be deposited on inner surfaces of the protrusions 32, e.g. inner surface 54A and/or inner surface 56A. Similarly, compositions may be applied to select portions of the protrusions. With non-contact printing, the first plurality of composition sites 135 may be disposed only on the distal ends 54 of the protrusions 32, only on the outer surface 54B of the distal ends 54 of the protrusions 32, only on the sidewalls 56 of the protrusions 32, only on the outer surface 56B of the sidewalls 56, or only on the outer surface of the distal ends 54 and sidewalls 56. Similarly, the third plurality of composition sites 139 may be disposed only on the inner surface 54A of the distal ends 54 or only on the inner surface 56A of the sidewalls 56 of the protrusions 32.

Forms of the present invention are contemplated where the first plurality of composition sites 135 comprise a first composition, a second plurality of composition sites 137 comprise a second composition, a third plurality of composition sites comprise a third composition, and a fourth plurality of composition sites comprise a fourth composition. Forms of the present invention are contemplated where at least one of the first composition, the second composition, the third composition, and/or the fourth composition are different. For those forms which do not include a fourth plurality of composition sites, at least one of the first composition, second composition, and/or third composition are different. And, as noted previously, forms of the present invention are contemplated where the first plurality of composition sites, the second plurality of composition sites, the third plurality of composition sites, or the fourth plurality of composition sites are utilized independent from one another.

Figure 21B:
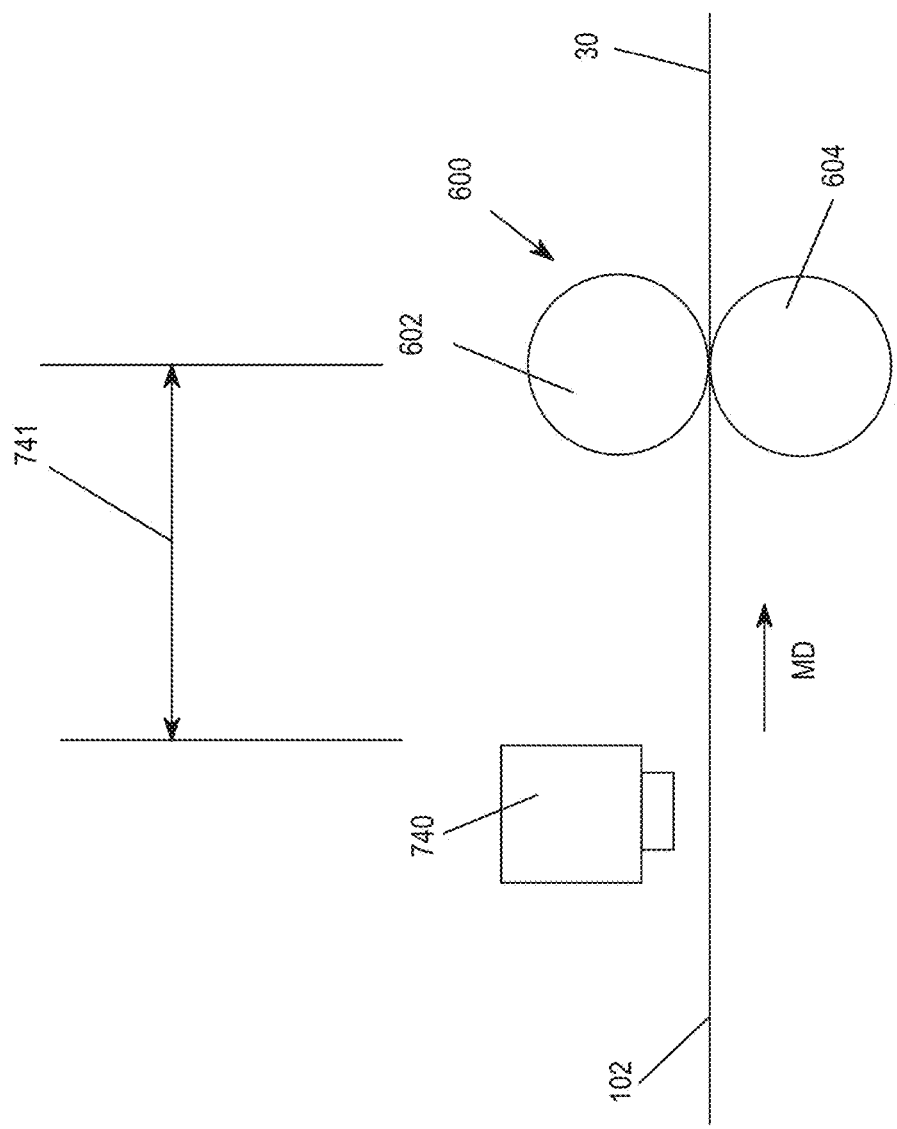
FIG. 21B is a schematic diagram showing exemplary spacing of particular elements in another exemplary apparatus in accordance with the present disclosure.

Addition processes are contemplated which do not utilize a visual system. Examples are provided with regard to FIGS. 21A-21B. In some forms of the present invention, compositions may be associated with protrusions without the use of a vision system. Regarding FIG. 21A, for those forms where a composition or composition(s) are applied to the textured web post formation of the protrusions, the printer 740 may be positioned within a distance 741 of the apparatus 600. Similarly, as shown in FIG. 21B, the printer 740 may be positioned within the distance 741 upstream of the apparatus 600. In some forms of the present invention, the distance 741 may be less than 5 times web width in the CD. In some forms, even where the distance 741 is 5 times the web width in the CD or less, a vision system may still be utilized. Distance 741 may be from a centerline of the first print head of the printer 740 to an axis of rotation of the first forming member 602 or second forming member 604. Where the forming members are plates, distance 741 may be with respect to the center of the forming plates.

Referring to FIGS. 19A-21B, the camera 731 can be fixed with respect to a manufacturing line such that the centerline of the camera 731 is co-linear with the machine centerline 130. In some forms, the centerline of the camera 731 is not co-linear with the machine centerline 730 but utilizes the machine centerline 730 and/or another fixed reference.

Any suitable camera may be utilized. For example, a camera having a bit depth of at least 8 may be utilized. In another example, a camera having a bit depth of at least 12 or at least 16 may be utilized. Cameras with higher bit depth can provide the computational device with much more numerical resolution allowing for better filtering of images by the computational device.

Any suitable computational device may be utilized with the present invention. Some suitable examples can include central processing units (CPU), graphical processing units (GPU), and/or field programmable gate arrays (FPGA). The processing power/speed of the computational device may vary depending on the speed of the manufacturing line of which images are being provided to the computational device. For example, faster line speeds may require additional processing power to ensure that the computational device can keep up with the images being provided by the camera. In some forms of the present invention, manufacturing line speeds can be greater than about 1 m/s, greater than about 3 m/s, greater than about 4 m/s, greater than about 5 m/s, greater than about 6 m/s, greater than about 7 m/s, greater than about 8 m/s, greater than about 9 m/s, greater than about 10 m/s, greater than about 11 m/s, greater than about 12 m/s, greater than about 13 m/s or greater than about 14 m/s specifically including all values within the above values and any ranges created thereby.

The computational device can comprise any suitable vision analysis software. Some suitable examples include National Instruments® Vision Development Module, MathWorks® Image Processing toolkit, OpenCV—open source computer vision library written in C++, or ImageJ. The vision analysis software can allow a user to extract a Fourier plane from the image provided by the camera and extract the phase plane from the image provided by the camera. Depending on the intermediate features and/or discontinuities being analyzed, settings may need to be adjusted. For example, apertures may be difficult to discern in low basis weight nonwovens without adjustment to the filtering to reduce the noise of the image signal. However, less filtering may be required for the same size apertures in a higher basis weight nonwoven. Samples of the images to be analyzed can be used in test runs to hone the filter settings and produce a signal which can provide accurate results.

Similarly, samples may be utilized to determine the best highlighting method for the protrusions 32. Different highlighting mechanisms can be used to determine which highlighting system provides the best image and best resolution for the computational device. Some suitable examples for highlighting protrusions 32 include backlighting, front lighting, side lighting, UV lighting, X-ray, thermal response, laser topography, the like or combinations thereof.

Additional forms of the present invention are contemplated where contrasting color materials may be utilized to facilitate visualization of features by the vision system. For example, a nonwoven laminate comprising contrasting color layers may facilitate viewing of the protrusions 32. Further examples of color enhancement of various discontinuities is described in U.S. Patent Application Serial No. US2016/0278986.

As noted previously, the vision analysis software can allow analysis of an image via the Fourier and phase plane of the image. Additionally, the vision analysis software can allow for comparisons between predetermined patterns and images from the camera—pattern recognition. Where the periodicity of the protrusions 32 is too disparate, Fourier analysis may not be appropriate. In such instances, pattern recognition may provide more accurate results/more accurate instructions to the printer. A pattern or a plurality of patterns of protrusions would need to be provided to the computational device and/or printer such that the comparison could be made between the transmitted image and the stored pattern(s).

For pattern recognition, a plurality of patterns may be stored in the computational device and/or printer to address potential phase shift of the pattern with respect to its web. The plurality of patterns may account for phase shifts of the protrusions in the textured nonwoven web.

Configurations are contemplated where the camera provides an image to the computational device which then creates a print file from the image. The print file can then be provided to the printer without the need for analysis. For example, the print file can account for any phase shift in the MD or CD. In this form, the need for predetermined patterns may be obviated.

Any suitable printer may be utilized with the present invention. As noted previously, the composition sites may comprise a plurality of discrete dots or droplets. The volume of the ink droplets can depend on the particular printing technology. By way of example, printing units that are VIDEOJET™ continuous ink jet printers can have ink drop volumes of about 240 pL and are delivered at relatively high drop velocities (e.g., about 13 m/s). Other printing technology (e.g. piezo drop on demand) can deliver ink drops having relatively small volumes, such as ink drops having a volume ranging from about 1 pL to about 80 pL, that are delivered at lower drop velocities (i.e., about ½ m/s) than continuous inkjet printing. Those skilled in the art know there are different inkjet technologies (e.g., continuous, piezo, thermal, valve) and different drop size ranges and different jet velocities. In general, smaller drop size infers that the CD dpi (resolution) is higher. The range 1-24 pL would equate to a CD resolution of 300-600 dpi. The VIDEOJET CD resolution is 128 dpi. So, more drops in CD can mean better opportunity to hit a fiber, which can result in better image quality and less ink blow-though. The slower the drop speed, the less ink blow-through.

An exemplary continuous ink jet printer is available from Videojet™ sold under the trade name of Videojet BX™. For the continuous ink jet printer, the ink droplets are dispensed from all of the jets of the print heads continuously, but only certain ink droplets are allowed to reach the precursor web or textured web at the composition sites. The other ink droplets can be prevented from reaching the precursor web or textured web by deflecting the ink droplets into a recycling flow for a continuous re-use. The operation of the individual ink jets of each print head can be controlled by a controller included in the Videojet BX™ system.

Exemplary drop on demand printers for use in the present invention may comprise multiple print heads allowing for the deposition of a plurality of compositions. In general, the printer of the present invention may comprise a controller, one or more print heads, and a composition management system. A suitable example of a printer includes the 1024 PH development kit available from FujiFilm Dimatix™ located in New Hampshire. A suitable example of the print heads which may be utilized, includes SG-1024 MA available from FujiFilm Dimatix™. Forms of the present invention are contemplated where the controller 120 (See FIGS. 1A, 2, 4A, and 4D) is utilized as the controller for the printer described above. Additional forms are contemplated where the printer described above comprises a separate controller in addition to the controller 120. Still in other forms of the present invention, where the need for a vision system is optional based upon the above disclosure, the controller for the printer may operate without the controller 120.

The webs of the present invention may be processed to a further extent to create disposable absorbent article. Some suitable examples include diapers, diaper pants, feminine pads, adult incontinence pads, etc. The webs of the present invention may form any suitable portion of a disposable absorbent article. For example, the webs of the present invention may form a portion of a topsheet, a backsheet, or an absorbent core which is disposed between the topsheet and the backsheet. In some forms, the webs of the present invention may be utilized to form barrier cuffs for a disposable absorbent article. In other forms, the webs of the present invention may be form a portion of at least one or more of the topsheet, backsheet, secondary topsheet, acquisition layer, distribution layer, absorbent core dusting layer, backsheet, barrier cuff, wing of a sanitary pad, ear on a diaper, or the like. Some exemplary disposable absorbent article are discussed hereafter.

Contact Application of Compositions

Another suitable method by which compositions may be deposited on textured nonwoven webs 30 of the present invention is via slot coating. In such forms, composition may be supplied to a slot gun so that the composition may be extruded through a nozzle having at least one very narrow elongated orifice, or slot. As shown in FIG. 22A, a nozzle 840 may provide composition to the textured nonwoven web 30 post formation of the protrusions. As shown, the textured nonwoven web 30 moves across the nozzle 840. As the textured nonwoven web 30 moves across the nozzle 840, composition is deposited on the textured nonwoven web 30. Where discrete composition sites are desired as described herein, the protrusions can face in the negative Z-direction in the form shown. In such forms, as the textured nonwoven web 30 moves across the nozzle 840, the protrusions contact the composition extruded through the nozzle 840 as opposed to the entire textured nonwoven web 30. In such forms, composition may be deposited on the distal ends and/or sidewalls of the protrusions which the first region of the textured nonwoven web remains without composition.

For the deposition of discrete composition areas, particularly on the distal ends of the protrusions, the nonwoven web 30 may require tensioning upstream and downstream of the nozzle 840 to minimize Z-direction movement of the nonwoven web 30 during processing. Additionally, depending on the height of the protrusions and the viscosity of the composition being extruded through the nozzle 840, the inlet/outlet angle of the nonwoven web 30 with respect to the nozzle 840 may need to be adjusted.

For those forms where the second surface 36 of the textured nonwoven web 30 is desired to comprise a plurality of composition sites, where interconnectedness of the composition sites is preferred, the protrusions of the textured nonwoven web 30 may be oriented in the positive Z-direction. In such forms, composition extruded by the nozzle 840 would be deposited on the second surface 36 of the textured nonwoven web 30 sans the openings in the second surface 36.

In some forms, as shown in FIG. 22B, a second nozzle 841 may be utilized to deposit composition on the textured nonwoven web 30. In such forms, assuming the protrusions are facing in the positive Z-direction, the first nozzle 840 may deposit composition on the second surface 36 sans the openings in the second surface 36, while the second nozzle 841 deposits a second composition on the distal ends and/or sidewalls of the protrusions. Forms of the present invention are contemplated where the first nozzle or second nozzle deposit composition(s) on the precursor web 102 prior to the formation of the protrusions by the apparatus 600.

Forms of the present invention are contemplated where one nozzle may comprise multiple slots from which compositions can be extruded. In such forms, one nozzle may deposit a plurality of compositions on a textured nonwoven web. For example, a nozzle may deposit a first composition in a center zone of a textured nonwoven web and deposit a second composition in a second and/or third zone spaced from one another in the CD via the central zone. In some forms, the first composition may be different than the second composition. In other forms, a third composition may be deposited on the third zone. In such forms, the third composition may be different than the second composition and the first composition.

In general, application of compositions via a slot gun can allow for much greater basis weight of composition deposition than non-contact printing. However, application of compositions via slot gun do not allow for precision application as described above with regard to non-contact printing.

The slot gun device is disclosed in additional detail in U.S. patent application Ser. No. 10/405,456 titled "Method and Device for Applying Fluids to Substrates" filed Apr. 2, 2003 by Lippelt and assigned to Nordson Corp. Versions of slot gun device are commercially available as Meltex Series Model No. EP-11 and EP-12 slot guns from Nordson Corp., Duluth, Ga.

Contact and Non-Contact Composition Deposition

Forms of the present invention are contemplated where a combination of non-contact printing and contact deposition are utilized. For example, as shown in FIG. 23, the printer 740 or second printer 742 may deposit the third plurality of composition sites on the inner surfaces of the protrusions 32. As shown, the printer 740 or second printer 742, in such forms would deposit composition on the first surface 34 or second surface 36, respectively, of the precursor web 102. The precursor web 102 would then be provided to the apparatus 600 forming protrusions in the precursor web thereby forming the textured nonwoven web 30. Post formation of the protrusions, the first nozzle 840 or 841 may deposit composition on the outer surface of the protrusions, e.g. distal end and/or sidewalls.

The configuration of the printers and nozzles in FIG. 23 is one example arrangement of these devices. Additional configurations are contemplated as disclosed in FIGS. 19A, 20A, 21A, 21B, 22A, and 22B.

Precursor Nonwoven Webs

The precursor nonwoven webs of the present invention can be made of any suitable nonwoven materials ("precursor materials"). As such, the textured nonwoven webs of the present invention can be made of any suitable nonwoven material. The nonwoven webs can be made from a single layer, or multiple layers (e.g., two or more layers). If multiple layers are used, they can be comprised of the same type of nonwoven material, or different types of nonwoven materials. In some cases, the precursor materials may be free of any film layers.

The fibers of the nonwoven precursor material(s) can be made of any suitable materials including, but not limited to natural materials, synthetic materials, and combinations thereof. Suitable natural materials include, but are not limited to cellulose, cotton linters, bagasse, wool fibers, silk fibers, etc. Cellulose fibers can be provided in any suitable form, including but not limited to individual fibers, fluff pulp, drylap, liner board, etc. Suitable synthetic materials include, but are not limited to nylon, rayon and polymeric materials. Suitable polymeric materials include, but are not limited to: polyethylene (PE), polyester, polyethylene terephthalate (PET), polypropylene (PP), and co-polyester. In some embodiments, however, the nonwoven precursor materials can be either substantially, or completely free, of one or more of these materials. For example, in some embodiments, the precursor materials may be substantially free of cellulose, and/or exclude paper materials. In some embodiments, one or more precursor materials can comprise up to 100% thermoplastic fibers. The fibers in some cases may, therefore, be substantially non-absorbent. In some embodiments, the nonwoven precursor materials can be either substantially, or completely free, of tow fibers.

The precursor nonwoven materials can comprise any suitable types of fibers. Suitable types of fibers include, but are not limited to: monocomponent, bicomponent, and/or biconstituent, non-round (e.g., shaped fibers (including but not limited to fibers having a trilobal cross-section) and capillary channel fibers). The fibers can be of any suitable size. The fibers may, for example, have major cross-sectional dimensions (e.g., diameter for round fibers) ranging from 0.1-500 microns. Fiber size can also be expressed in denier, which is a unit of weight per length of fiber. The constituent fibers may, for example, range from about 0.1 denier to about 100 denier. The constituent fibers of the nonwoven precursor web(s) may also be a mixture of different fiber types, differing in such features as chemistry (e.g., PE and PP), components (mono- and bi-), shape (i.e. capillary channel and round) and the like.

The nonwoven precursor webs can be formed from many processes, such as, for example, air laying processes, wetlaid processes, meltblowing processes, spunbonding processes, and carding processes. The fibers in the webs can then be bonded via spunlacing processes, hydroentangling, calendar bonding, through-air bonding and resin bonding. Some of such individual nonwoven webs may have bond sites 46 where the fibers are bonded together.

In the case of spunbond webs, the web may have a thermal point bond 46 pattern that is not highly visible to the naked eye. For example, dense thermal point bond patterns are equally and uniformly spaced are typically not highly visible. After the material is processed through the mating male and female rolls, the thermal point bond pattern is still not highly visible. Alternatively, the web may have a thermal point bond pattern that is highly visible to the naked eye. For example, thermal point bonds that are arranged into a macro-pattern, such as a diamond pattern, are more visible to the naked eye. After the material is processed through the mating male and female rolls, the thermal point bond pattern is still highly visible and can provide a secondary visible texture element to the material.

The basis weight of nonwoven materials is usually expressed in grams per square meter (gsm). The basis weight of a single layer nonwoven material can range from about 8 gsm to about 100 gsm, depending on the ultimate use of the material 30. For example, the topsheet of a topsheet/acquisition layer laminate or composite may have a basis weight from about 8 to about 40 gsm, or from about 8 to about 30 gsm, or from about 8 to about 20 gsm. The acquisition layer may have a basis weight from about 10 to about 120 gsm, or from about 10 to about 100 gsm, or from about 10 to about 80 gsm. The basis weight of a multi-layer material is the combined basis weight of the constituent layers and any other added components. The basis weight of multi-layer materials of interest herein can range from about 20 gsm to about 150 gsm, depending on the ultimate use of the material 30. The nonwoven precursor webs may have a density that is between about 0.01 and about 0.4 g/cm$^3$ measured at 0.3 psi (2 kPa).

The precursor nonwoven webs may have certain desired characteristics. The precursor nonwoven web(s) each have a first surface, a second surface, and a thickness. The first and second surfaces of the precursor nonwoven web(s) may be generally planar. It is typically desirable for the precursor nonwoven web materials to have extensibility to enable the fibers to stretch and/or rearrange into the form of the protrusions. If the nonwoven webs are comprised of two or more layers, it may be desirable for all of the layers to be as extensible as possible. Extensibility is desirable in order to maintain at least some non-broken fibers in the sidewalls around the perimeter of the protrusions. It may be desirable for individual precursor webs, or at least one of the nonwovens within a multi-layer structure, to be capable of undergoing an apparent elongation (strain at the breaking force, where the breaking force is equal to the peak force) of greater than or equal to about one of the following amounts: 100% (that is double its unstretched length), 110%, 120%, or 130% up to about 200%. It is also desirable for the precursor nonwoven webs to be capable of undergoing plastic deformation to ensure that the structure of the deformations is "set" in place so that the nonwoven web will not tend to recover or return to its prior configuration.

Figure 16:
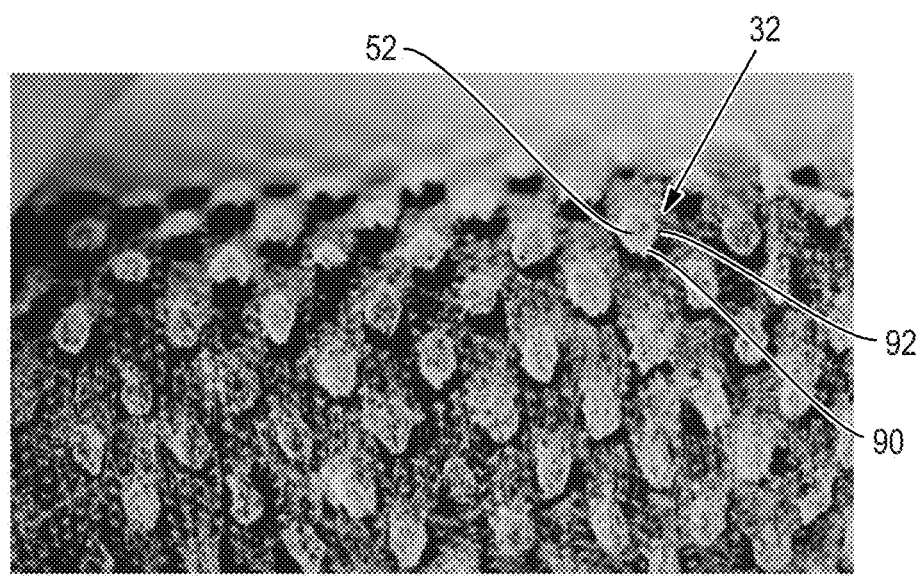
FIG. 16 is a perspective view photomicrograph of one layer of a multiple layer nonwoven material on the surface of a forming roll showing the "hanging chads" that can be formed in one of the layers when some nonwoven precursor web materials are used.

Materials that are not extensible enough (e.g., inextensible PP) may form broken fibers around much of the perimeter of the deformation, and create more of a "hanging chad" 90 (i.e., the cap 52 of the protrusions 32 (shown in FIG. 6) may be at least partially broken from and separated from the rest of the protrusion (as shown in FIG. 16). The area on the sides of the protrusion where the fibers are broken is designated with reference number 92. Materials such as that shown in FIG. 16 will not be suitable for a single layer structure, and, if used, will typically be part of a composite multi-layer structure in which another layer has protrusions 32 as described herein.

When the fibers of a nonwoven web are not very extensible, it may be desirable for the nonwoven to be underbonded as opposed to optimally bonded. A thermally bonded nonwoven web's tensile properties can be modified by changing the bonding temperature. A web can be optimally or ideally bonded, underbonded, or overbonded. Optimally or ideally bonded webs are characterized by the highest breaking force and apparent elongation with a rapid decay in strength after reaching the breaking force. Under strain, bond sites fail and a small amount of fibers pull out of the bond site. Thus, in an optimally bonded nonwoven, the fibers 38 (shown FIG. 7) will stretch and break around the bond sites 46 (shown in FIG. 3) when the nonwoven web is strained beyond a certain point. Often there is a small reduction in fiber diameter in the area surrounding the thermal point bond sites 46. Underbonded webs have a lower breaking force and apparent elongation when compared to optimally bonded webs, with a slow decay in strength after reaching the breaking force. Under strain, some fibers will pull out from the thermal point bond sites 46. Thus, in an underbonded nonwoven, at least some of the fibers 38 can be separated easily from the bond sites 46 to allow the fibers 38 to pull out of the bond sites and rearrange when the material is strained. Overbonded webs also have a lowered breaking force and elongation when compared to optimally bonded webs, with a rapid decay in strength after reaching the breaking force. The bond sites look like films and result in complete bond site failure under strain.

When the nonwoven web comprises two or more layers, the different layers can have the same properties, or any suitable differences in properties relative to each other. In some forms, the textured nonwoven web 30 can comprise a two layer structure that is used in an absorbent article. Referring to back to FIGS. 11A-11F, as described above, one of the layers, a second layer 30B, can serve as the topsheet of the absorbent article, and the first layer 30A can be an underlying layer (or sub-layer) and serve as an acquisition layer. The acquisition layer 30A receives liquids that pass through the topsheet and distributes them to underlying absorbent layers. In such a case, the topsheet 30B may be less hydrophilic than sub-layer(s) 30A, which may lead to better dewatering of the topsheet. In other embodiments, the topsheet can be more hydrophilic than the sub-layer(s). In some cases, the pore size of the acquisition layer may be reduced, for example via using fibers with smaller denier or via increasing the density of the acquisition layer material, to better dewater the pores of the topsheet. In other cases, the topsheet can have fibers with a smaller fiber diameter or fiber denier than the acquisition layer to enable a softer feel and better masking.

The second nonwoven layer 30B that may serve as the topsheet can have any suitable properties. Properties of interest for the second nonwoven layer, when it serves as a topsheet, in addition to sufficient extensibility and plastic deformation may include uniformity and opacity. As used herein, "uniformity" refers to the macroscopic variability in basis weight of a nonwoven web. As used, herein, "opacity" of nonwoven webs is a measure of the impenetrability of visual light, and is used as visual determination of the relative fiber density on a macroscopic scale. As used herein, "opacity" of the different regions of a single nonwoven deformation is determined by taking a photomicrograph at 20× magnification of the portion of the nonwoven containing the deformation against a black background. Darker areas indicate relatively lower opacity (as well as lower basis weight and lower density) than white areas.

Several examples of nonwoven materials suitable for use as the second nonwoven layer 30B include, but are not limited to: spunbonded nonwovens; carded nonwovens; and other nonwovens with high extensibility (apparent elongation in the ranges set forth above) and sufficient plastic deformation to ensure the structure is set and does not have significant recovery. One suitable nonwoven material as a topsheet for a topsheet/acquisition layer composite structure may be an extensible spunbonded nonwoven comprising polypropylene and polyethylene. The fibers can comprise a blend of polypropylene and polyethylene, or they can be bi-component fibers, such as a sheath-core fiber with polyethylene on the sheath and polypropylene in the core of the fiber. Another suitable material is a bi-component fiber spunbonded nonwoven comprising fibers with a polyethylene sheath and a polyethylene/polypropylene blend core.

The first nonwoven layer 30A that may, for example, serve as the acquisition layer can have any suitable properties. Properties of interest for the first nonwoven layer, in addition to sufficient extensibility and plastic deformation may include uniformity and opacity. If the first nonwoven layer 30A serves as an acquisition layer, its fluid handling properties must also be appropriate for this purpose. Such properties may include: permeability, porosity, capillary pressure, caliper, as well as mechanical properties such as sufficient resistance to compression and resiliency to maintain void volume. Suitable nonwoven materials for the first nonwoven layer when it serves as an acquisition layer include, but are not limited to: spunbonded nonwovens; through-air bonded ("TAB") carded nonwoven materials; spunlace nonwovens; hydroentangled nonwovens; and, resin bonded carded nonwoven materials. Of course, the composite structure may be inverted and incorporated into an article in which the first layer 30A serves as the topsheet and the second layer 30B serves as an acquisition layer. In such cases, the properties and exemplary methods of the first and second layers described herein may be interchanged.

The layers of a two or more layered nonwoven web structure can be combined together in any suitable manner. In some cases, the layers can be unbonded to each other and held together autogenously (that is, by virtue of the formation of deformations therein). For example, both precursor webs 30A and 30B contribute fibers to deformations in a "nested" relationship that joins the two precursor webs together, forming a multi-layer web without the use or need for adhesives or thermal bonding between the layers. In other embodiments, the layers can be joined together by other mechanisms. If desired an adhesive between the layers, ultrasonic bonding, chemical bonding, resin or powder bonding, thermal bonding, or bonding at discrete sites using a combination of heat and pressure can be selectively utilized to bond certain regions or all of the precursor webs. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together.

If adhesives are used, they can be applied in any suitable manner or pattern including, but not limited to: slots, spirals, spray, and curtain coating. Adhesives can be applied in any suitable amount or basis weight including, but not limited to between about 0.5 and about 30 gsm, alternatively between about 2 and about 5 gsm. Examples of adhesives could include hot melt adhesives, such as polyolefins and styrene block copolymers.

When the precursor nonwoven web comprises two or more layers, it may be desirable for at least one of the layers to be continuous, such as in the form of a web that is unwound from a roll. In some embodiments, each of the layers can be continuous. In alternative embodiments, one or more of the layers can be continuous, and one or more of the layers can have a discrete length. The layers may also have different widths. For example, in making a combined topsheet and acquisition layer for an absorbent article, the nonwoven layer that will serve as the topsheet may be a continuous web, and the nonwoven layer that will serve as the acquisition layer may be fed into the manufacturing line in the form of discrete length (for example, rectangular, or other shaped) pieces that are placed on top of the continuous web. Such an acquisition layer may, for example, have a lesser width than the topsheet layer. The layers may be combined together as described above.

Compositions

As mentioned previously, textured nonwoven webs of the present invention may comprise a plurality of composition sites each of which comprises a composition. The composition sites of the present invention may comprise a plurality of dots or droplets of composition particularly where ink jet printing is utilized. In some forms, the first plurality of composition sites may comprise a first density of discrete dots which are spaced apart at a particular dots per inch, "DPI" spacing. The second plurality of composition sites may comprise a second plurality of discrete dots which are spaced apart at a different DPI. In some forms, the DPI of the first plurality of discrete dots may be greater than the DPI of the second plurality of discrete dots. The third plurality of composition sites and the fourth plurality of composition sites may be similarly configured.

The plurality of composition sites applied to the precursor web and/or textured nonwoven web may comprise any suitable composition or combination of compositions. For example, in some forms, a plurality of composition sites may comprise a hydrophilic composition. Some suitable examples of hydrophilic compositions include non-ionic surfactants including esters, amides, carboxylic acids, alcohols, ethers—polyoxyethylene, polyoxypropylene, sorbitan, ethoxylated fatty alcohols, alyl phenol polyethoxylates, lecithin, glycerol esters and their ethoxylates, and sugar based surfactants (polysorbates, polyglycosides). Other suitable examples include anionic surfactants including sulfonates, sulfates, phosphates, alkali metal salts of fatty acids, fatty alcohol monoesters of sulfuric acid, linear alkyl benzene sulfonates, alkyl diphenyloxide sulfonates, lignin sulfonates, olefin sulfonates, sulfosuccinates, and sulfated ethoxylates of fatty alcohols. Other suitable examples include cationic surfactants including amines (primary, secondary, tertiary), quaternary ammoniums, pyridinium, quaternary ammonium salts-QUATS, alkylated pyridinium salts, alkyl primary, secondary, tertiary amines, and alkanolamides. Other suitable examples include zwiterionic surfactants including amino acids and derivatives, amine oxide, betaines, and alkyl amine oxides. Other suitable examples include polymeric surfactants including polyamines, carboxylic acid polymers and copolymers, EO/PO block copolymers, ethylene oxide polymers and copolymers, and polyvinylpyrrolidone. Other suitable examples include silicone surfactants including dimethyl siloxane polymers with hydrophile. And other suitable examples include perfluorocarboxylic acid salts and fluorosurfactants.

In some forms, a plurality of composition sites may comprise a hydrophobic composition. Some suitable examples of hydrophobic compositions include fluorinated or perfluorinated polymers; silicones; fluorochemicals; zirconium compounds; oils; latexes; waxes; crosslinking resins; and blends thereof; fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets; nanostructured particles selected from fumed silica, hydrophobic titania, zinc oxide, nanoclay, and mixtures thereof; fats and oils, glycerol derivatives; hydrophobic silicones or suitable combinations thereof.

In some forms, a plurality of composition sites may comprise a lotion. Any suitable lotion may be utilized as a composition of the present invention. Some suitable lotions are described in U.S. Patent Application Publication Nos. 2003/0206943 and 2007/0219515. Lotions suitable for use as compositions in the present invention may comprise from about 60-99.9 percent of a carrier. Suitable carrier compounds include petroleum-based hydrocarbons having from about 8 to about 32 carbon atoms, fatty alcohols having from about 12 to about 18 carbon atoms, polysiloxane compounds, fatty acid esters, alkyl ethoxylates, lower alcohols having from about 2 to about 6 carbon atoms, low molecular weight glycols and polyols, fatty alcohol ethers having from about 12 to about 22 carbon atoms in their fatty chain, lanolin and its derivatives, ethylene glycol derivatives of $C_{12}$-$C_{22}$ fatty acids, glyceride and its derivatives including acetoglycerides and ethoxylated glycerides of $C_{12}$-$C_{18}$ fatty acids, and mixtures thereof. Other suitable carriers include oils or fats, such as natural oils or fats, or natural oil or fat derivatives, in particular of plant or animal origin. Suitable carriers further encompass waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Suitable waxes which can be incorporated into the lotion composition include animal, vegetable, mineral or silicone based waxes which may be natural or synthetic, and including mixtures thereof.

Additionally, lotions suitable for use with the present invention may comprise optional ingredients such as skin treatment agents including hexamidine, zinc oxide, and niacinamide, glycerine, chamomile, panthenol, fats and oils, and/or skin conditioning agents, perfumes, deodorants, opacifiers, astringents, preservatives, emulsifying agents, film formers, stabilizers, proteins, lecithin, urea, colloidal oatmeal, pH control agents. Additional optional ingredients include particles, wetting agents, and/or viscosity or thickening agents.

Additional compositions are contemplated. For example, compositions utilized with the present invention may comprise health actives. Some examples include prebiotics which include mucopolysaccharides, oligosaccharides such as galactooligosaccharides ("GOS"), polysaccharides, amino acids, vitamins, nutrient precursors, harvested metabolic products of biological organisms, lipids, and proteins. Other suitable prebiotics are disclosed in PCT Patent Application Publication No. WO 2013122932 A2.

Other suitable health actives comprise organic acids including acetic acid, propionic acid, lactic acid, ascorbic acid, phenylalanine, citric acid, butyric acid, valeric acid, capronic acid, succinic acid and/or a salt thereof, soluble acrylic acid polymers known to the art as Carbopols®, alone or in combination with organic acids known to the art such as alphahydroxy acids, more preferably benzoic acid, alginic acid, sorbic acid, stearic acid, oleic acid, edetic acid, gluconodeltalactone, acetic acid, fumaric acid, lactic acid, citric acid, propionic acid, malic acid, succinic acid, gluconic acid, ascorbic acid and tartaric acid and the like.

Other suitable health actives include calcium salts, calcium lactate and/or calcium citrate malate, bacterial metabolites and extracellular products. In some forms, compositions useful with the present invention may comprise skin care actives including allantoin, aluminum hydroxide gel, calamine, cocoa butter, colloidal oatmeal, dimethicone, cod liver oil (in combination), glycerine, hard, fat, kaolin, petrolatum, lanolin, mineral oil, shark liver oil, white petrolatum, sodium bicarbonate, topical starch, zinc acetate, zinc carbonate, zinc oxide, and the like. Additional skin care actives are disclosed in PCT Patent Application Publication No. WO 2013/1222932.

Other suitable health actives include ingredients useful for regulating and/or improving a condition of mammalian skin. Some non-limiting examples of such ingredients include vitamins; peptides and peptide derivatives; sugar amines, phytosterols, salicylic acid compounds, hexamidines, dialkanoyl hydroxyproline compounds, flavonoids, retinoid compounds, botanicals, N-acyl amino acid compounds, their derivatives, and combinations thereof. Other examples include a sugar amine, which is also known as an amino sugar. Exemplary sugar amines suitable for use herein are described in PCT Publication No. WO 02/076423 and U.S. Pat. No. 6,159,485.

Other examples of suitable compositions include a vitamin B3 compound (e.g., niacinamide). Vitamin B3 compounds may regulate skin conditions as described in U.S. Pat. No. 5,939,082. Some exemplary derivatives of the foregoing vitamin B3 compounds include nicotinic acid esters, including non-vasodilating esters of nicotinic acid (e.g., tocopheryl nicotinate, myristyl nicotinate). Other examples include a salicylic acid compound, its esters, its salts, or combinations thereof. Still other examples include hexamidine compounds, its salts and derivatives. Other suitable examples include a flavonoid compound. Flavonoids are broadly disclosed in U.S. Pat. Nos. 5,686,082 and 5,686,367.

Additional examples include one or more N-acyl amino acid compounds. The amino acid can be one of any of the amino acids known in the art. A list of possible side chains of amino acids known in the art are described in Stryer, Biochemistry, 1981, published by W.H. Freeman and Company.

Additional examples include a retinoid. "Retinoid" as used herein means natural and synthetic analogs of Vitamin A, or retinol-like compounds which possess the biological activity of Vitamin A in the skin, as well as the geometric isomers and stereoisomers of these compounds.

Other suitable examples may comprise a peptide, including but not limited to, di-, tri-, tetra-, penta-, and hexapeptides and derivatives thereof. Peptides may contain ten or fewer amino acids and their derivatives, isomers, and complexes with other species such as metal ions (e.g., copper, zinc, manganese, magnesium, and the like). Peptide refers to both naturally occurring and synthesized peptides. Also useful herein are naturally occurring and commercially available compositions that contain peptides.

Compositions of the present invention may also include one or more water-soluble vitamins Examples of water-soluble vitamins including, but are not limited to, water-soluble versions of vitamin B, vitamin B derivatives, vitamin C, vitamin C derivatives, vitamin K, vitamin K derivatives, vitamin D, vitamin D derivatives, vitamin E, vitamin E derivatives, provitamins thereof, such as panthenol and mixtures thereof.

Other suitable ingredients include a conditioning agent such as a humectant, a moisturizer, or a skin conditioner. Some non-limiting examples of conditioning agents include, but are not limited to, guanidine; urea; glycolic acid and glycolate salts (e g ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols;

sugars (e.g., melibiose) and starches; sugar and starch derivatives (e.g., alkoxylated glucose, fucose); hyaluronic acid; lactamide monoethanolamine; acetamide monoethanolamine; panthenol; allantoin; and mixtures thereof. Also useful herein are the propoxylated glycerols described in U.S. Pat. No. 4,976,953. Also useful are various $C_1$-$C_{30}$ monoesters and polyesters of sugars and related materials. These esters are derived from a sugar or polyol moiety and one or more carboxylic acid moieties.

Depending on the manner in which the compositions are provided to the web, it is important to consider the rheology of the compositions being applied. For example, viscosity of the composition can be an important factor as viscosities which are too low can migrate out of the applied area, e.g. first composition sites. In contrast, a composition with too high of a viscosity can be difficult to apply via digital printer. And, other forms of application of the composition may prove to be much slower than that of the digital printer.

The composition of the present invention may be formulated to optimize its deposition by non-contact printing, e.g. ink jet printing. For example, the components of the desired composition can be dissolved or dispersed in a suitable solvent, such as water or another organic solvent. Some suitable organic solvents include ketones such as acetone, diethyl ketone, cyclohexanone and the like. Additional suitable solvents include alcohols such as methanol, ethanol, n-propanol, isopropanol, n-butanol, 1-methoxy-2-propanol, and the like. Additional suitable solvents include esters such as ethyl acetate, propyl acetate, butyl acetate and the like. Additional examples include ethers, lactones and amides. If desired, a mixture of solvents may be used. Additionally surfactants, rheology modifiers, and colorants such as dyes or pigments may be added to the formulation.

With regard to the compositions being applied via non-contact printing, inkjet printing generally relies on the generation of sequences of droplets. Behavior of the composition during droplet ejection is dependent on material properties such as density, viscosity and surface tension. The behavior of a composition when inkjet printed can be predicted via two dimensionless numbers, i.e. Ohnesorge number and Weber number. The equation for determining the Oh number is provided below.

$$Oh = \frac{\eta}{\sqrt{\rho \gamma L}}$$

where $\eta$ is viscosity, $\rho$ is density, $\gamma$ is surface tension of the composition, and L is the characteristic diameter (print head nozzle diameter for inkjet printing in meters).

Stable drop formation can be characterized by the reciprocal of the Ohnesorge number, namely Z=1/Oh. Stable drop formation can be expected from compositions when $14 \geq Z \geq 1$. The viscosity of the desired composition should be measured at target operating temperature with shear rates between 200 and 20 s−1. The surface tension should be recorded in N/m. The density should be calculated in kg/m3, and the viscosity should be recorded in Pa·s.

Additionally, a composition of the present invention may comprise a Weber number of between about 4 and 1000. The Weber number may be calculated as follows:

$$We = \frac{v^2 \rho L}{\gamma}$$

where $\rho$ is the density of the composition in kg/m3; v is the velocity of the composition in m/s; L is the characteristic diameter (print head nozzle diameter for inkjet printing; and $\gamma$ is the surface tension in N/m.

In some forms, the compositions of the present invention may comprise a viscosity of between about 5 and 25 centipoise. The compositions may comprise a surface tension of between about 25 and 40 dyne/cm. In some forms of the present invention, the compositions may comprise a density of from about 0.6 grams/cubic cm to about 2.0 grams/cubic cm, specifically including all values within this range and any ranges created thereby.

Disposable Absorbent Articles

The textured nonwoven webs of the present invention may comprise any suitable portion of a disposable absorbent article and/or cleaning article. Some suitable examples, include a topsheet, backsheet, barrier cuff, intermediate layers between the topsheet and an absorbent core and/or intermediate layers between the backsheet and the absorbent core. Forms are contemplated where disposable absorbent articles utilize multiple textured nonwoven webs of the present invention in one or more of the preceding portions of the disposable absorbent article.

Referring to FIG. 24, an absorbent article 1710 which may utilize the material webs described herein may be a sanitary napkin/feminine hygiene pad. As shown, the sanitary napkin 1710 may comprise a liquid permeable topsheet 1714, a liquid impermeable, or substantially liquid impermeable, backsheet 1716, and an absorbent core 1718 positioned intermediate the topsheet 1714 and the backsheet 1716. The sanitary napkin 1710 may comprise wings 1720 extending outwardly with respect to a longitudinal axis 1780 of the sanitary napkin 1710. The sanitary napkin 1710 may also comprise a lateral axis 1790. The wings 1720 may be joined to the topsheet 1714, the backsheet 1716, and/or the absorbent core 1718. The sanitary napkin 1710 may also comprise a front edge 1722, a rear edge 1724 longitudinally opposing the front edge 1722, a first side edge 1726, and a second side edge 1728 laterally opposing the first side edge 1726. The longitudinal axis 1780 may extend from a midpoint of the front edge 1722 to a midpoint of the rear edge 1724. The lateral axis 1790 may extend from a midpoint of the first side edge 1726 to a midpoint of the second side edge 1728. The sanitary napkin 1710 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1718 may be any absorbent member which is generally compressible, conformable, non-irritating to the wearer's skin, and capable of absorbing and retaining liquids such as urine, menses, and/or other body exudates. The absorbent core 1718 may be manufactured from a wide variety of liquid-absorbent materials commonly used in disposable absorbent articles such as comminuted wood pulp which is generally referred to as airfelt. The absorbent core 1718 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1718 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1718 may comprise one or more channels, such as two, three, four, five, or six channels.

The absorbent core 1718 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1710 may comprise additional layers between the topsheet 1714 and the absorbent core 1718. For example, the absorbent article 1710 may comprise a secondary topsheet and/or an acquisition layer positioned between the topsheet 1714 and the absorbent core 1718. The secondary topsheet may comprise a nonwoven, and as mentioned herein, the protrusions may be formed, at least in part, in the secondary topsheet along with the topsheet. The secondary topsheet may comprise a nonwoven material. The nonwoven material may comprise airlaid fibers, spunalce fibers, needlepunch fibers. In some forms, the secondary topsheet may comprise a carded hi-loft nonwoven or may comprise crimped fibers.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. However, it should be noted that other flexible liquid impervious materials may be used as the backsheet. Herein, "flexible" refers to materials which are compliant and which will readily conform to the general shape and contours of the wearers body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

Still another example of a disposable absorbent article which may utilize the material webs of the present invention are diapers which include non-refastenable pants, re-fastenable pants and/or re-fastenable diapers. Diapers have can have a similar construction to that of sanitary napkins. An exemplary diaper is described below.

Referring to FIG. 25, a plan view of an example absorbent article that is a diaper 1900 in its flat-out, uncontracted state (i.e., with elastic induced contraction pulled out) with portions of the structure being cut-away to more clearly show the construction of the diaper 1900 and with its wearer-facing surface toward the viewer. This diaper is shown for illustration purpose only as the present disclosure may be used for making a wide variety of diapers and other absorbent articles.

Figure 26:
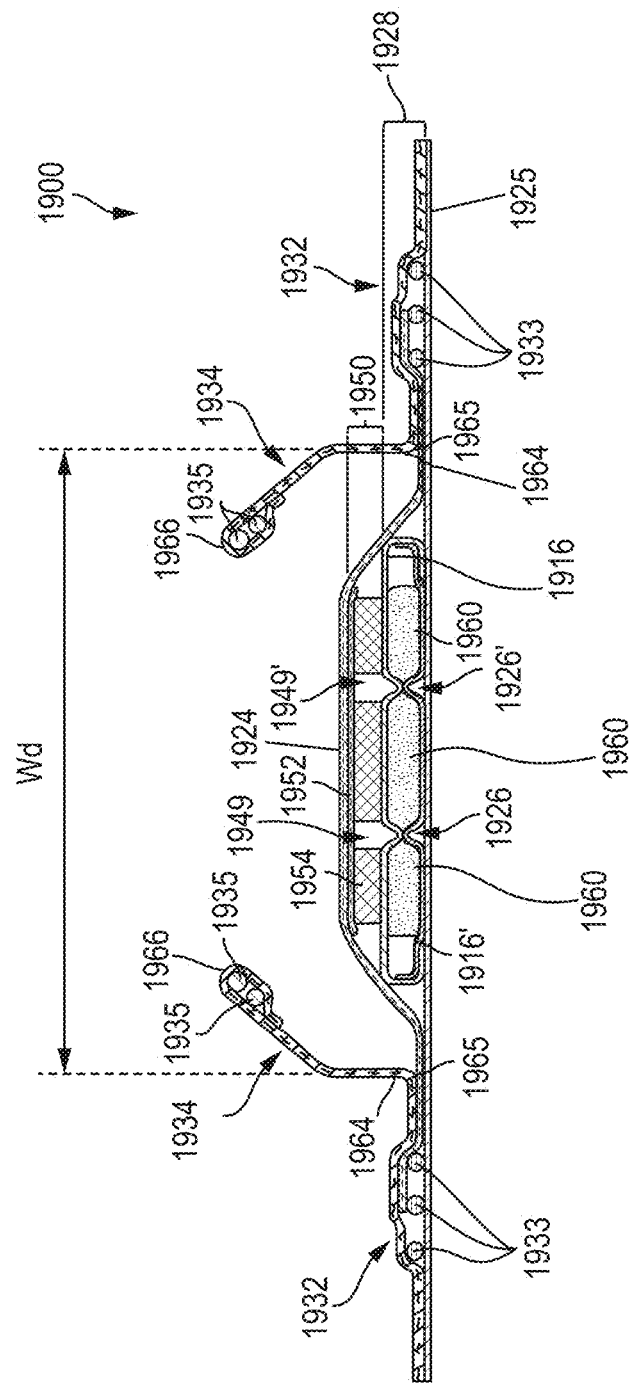
FIG. 26 is a cross-sectional view of the absorbent article taken about line 26-26 of FIG. 25 in accordance with the present disclosure.

The absorbent article may comprise a liquid permeable topsheet 1924, a liquid impermeable backsheet 1925, an absorbent core 1928 positioned at least partially intermediate the topsheet 1924 and the backsheet 1925, and barrier leg cuffs 1934. The absorbent article may also comprise a liquid management system ("LMS") 1950 (shown in FIG. 26), which, in the example represented, comprises a distribution layer 1954 and an acquisition layer 1952 that will both be further discussed below. In various forms, the acquisition layer 1952 may instead distribute bodily exudates and the distribution layer 1954 may instead acquire bodily exudates or both layers may distribute and/or acquire bodily exudates. The LMS 1950 may also be provided as a single layer or two or more layers. The absorbent article may also comprise elasticized gasketing cuffs 1932 joined to the chassis of the absorbent article, typically via the topsheet and/or backsheet, and substantially planar with the chassis of the diaper.

The Figures also show typical taped diaper components such as a fastening system comprising adhesive tabs 1942 or other mechanical fasteners attached towards the rear edge of the absorbent article 1900 and cooperating with a landing zone on the front of the absorbent article 1900. The absorbent article may also comprise other typical elements, which are not represented, such as a rear elastic waist feature and a front elastic waist feature, for example.

The absorbent article 1900 may comprise a front waist edge 1910, a rear waist edge 1912 longitudinally opposing the front waist edge 1910, a first side edge 1903, and a second side edge 1904 laterally opposing the first side edge 1903. The front waist edge 1910 is the edge of the absorbent article 1900 which is intended to be placed towards the front of the user when worn, and the rear waist edge 1912 is the opposite edge. Together the front waist edge 1910 and the rear waist edge form waist opening when the absorbent article 1900 is donned on a wearer. The absorbent article 1900 may have a longitudinal axis 1980 extending from the lateral midpoint of the front waist edge 1910 to a lateral midpoint of the rear waist edge 1912 of the absorbent article 1900 and dividing the absorbent article 1900 in two substantially symmetrical halves relative to the longitudinal axis 1980, with article placed flat and viewed from the wearer-facing surface as illustrated FIG. 19. The absorbent article may also have a lateral axis 1990 extending from the longitudinal midpoint of the first side edge 1903 to the longitudinal midpoint of the second side edge 1904. The length L of the absorbent article 1900 may be measured along the longitudinal axis 1980 from the front waist edge 1910 to the rear waist edge 1912. The crotch width of the absorbent article 1900 may be measured along the lateral axis 1990 from the first side edge 1903 to the second side edge 1904. The absorbent article 1900 may comprise a front waist region 1905, a rear waist region 1906, and a crotch region 1907. The front waist region, the rear waist region, and the crotch region each define ⅓ of the longitudinal length of the absorbent article. Front and back portions may also be defined on opposite sides of the lateral axis 1990.

The topsheet 1924, the backsheet 1925, the absorbent core 1928, and the other article components may be assembled in a variety of configurations, in particular by gluing or heat embossing, for example. Example diaper configurations are described generally in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core 1928 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

Figure 27:
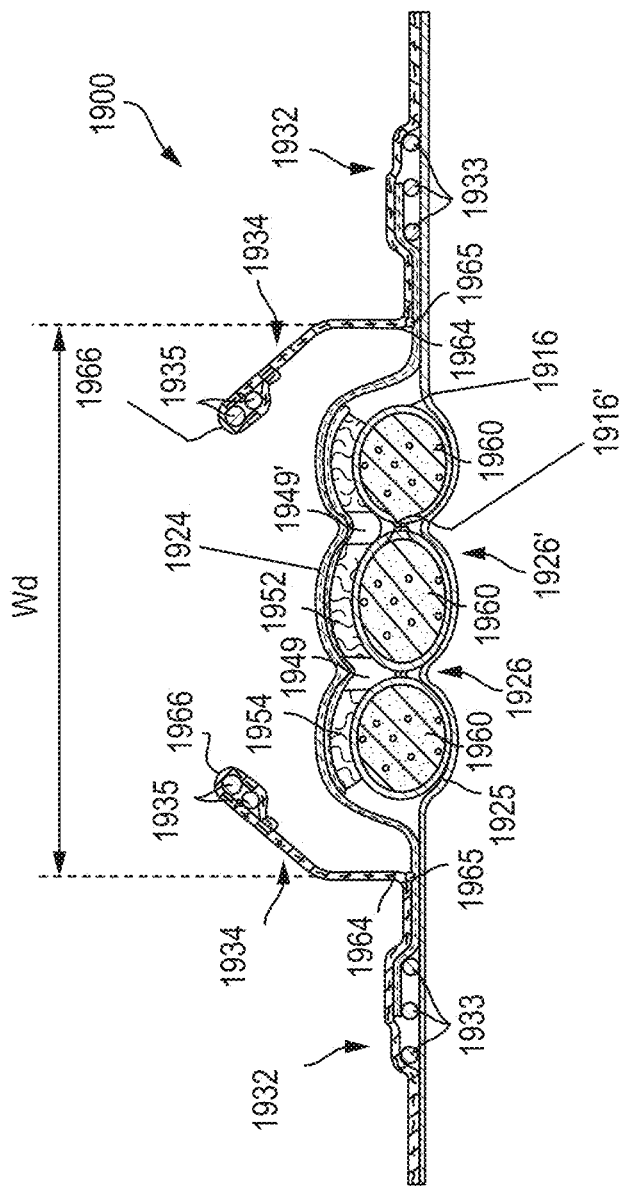
FIG. 27 is a view of the absorbent article of FIG. 26 where the absorbent article has been at least partially loaded with fluid in accordance with the present disclosure.

The absorbent core 1928 may comprises one or more channels, represented in FIG. 19 as the four channels 1926, 1926' and 1927, 1927'. Additionally or alternatively, the LMS 1950 may comprises one or more channels, represented in FIGS. 25-27 as channels 1949, 1949'. In some forms, the channels of the LMS 1950 may be positioned within the absorbent article 1900 such they aligned with, substantially aligned with, overlap, or at least partially overlap, the channels of the absorbent core 1928. These and other components of the absorbent articles will now be discussed in more details.

The topsheet 1924 is the part of the absorbent article that is directly in contact with the wearer's skin. The topsheet 1924 may be joined to the backsheet 1925, the core 1928 and/or any other layers as is known to those of skill in the art. Usually, the topsheet 1924 and the backsheet 1925 are joined directly to each other in some locations (e.g., on or close to the periphery of the article) and are indirectly joined together in other locations by directly joining them to one or more other elements of the absorbent article 1900.

The backsheet 1925 is generally that portion of the absorbent article 1900 positioned adjacent the garment-facing surface of the absorbent core 1928 and which prevents, or at least inhibits, the bodily exudates absorbed and contained therein from soiling articles such as bedsheets and undergarments. The backsheet 1925 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm Example backsheet films include those manufactured by Tredegar Corporation, based in Richmond, Va., and sold under the trade name CPC2 film. Other suitable backsheet materials may include breathable materials which permit vapors to escape from the absorbent article 1900 while still preventing, or at least inhibiting, bodily exudates from passing through the backsheet 1925. Example breathable materials may include materials such as woven webs, non-woven webs, and composite materials such as film-coated nonwoven webs, microporous films, and monolithic films.

The backsheet 1925 may be joined to the topsheet 1924, the absorbent core 1928, and/or any other element of the absorbent article 1900 by any attachment methods known to those of skill in the art. Suitable attachment methods are described above with respect to methods for joining the topsheet 1924 to other elements of the absorbent article 1900.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 1928 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 1928 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 1928 may also comprise a generally planar top side and a generally planar bottom side. The core 1928 may have a longitudinal axis 80' corresponding substantially to the longitudinal axis 80 of the absorbent article, as seen from the top in a planar view as in FIG. 19. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 1916, 1916' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 1916 may at least partially surround the second material, substrate, or nonwoven 1916' to form the core wrap. The first material 1916 may surround a portion of the second material 1916' proximate to the first and second side edges 1903 and 1904.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 1928 may comprise a first absorbent layer and a second absorbent layer. The first absorbent layer may comprise the first material 1916 and a first layer of absorbent material 1960, which may be 100% or less of SAP. The second absorbent layer may comprise the second material 1916' and a second layer of absorbent material 1960, which may also be 100% or less of SAP.

The fibrous thermoplastic adhesive material may be at least partially in contact with the absorbent material 1960 in the land areas and at least partially in contact with the materials 1916 and 1916' in the junction areas. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 1928 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article 1900 may comprise a pair of barrier leg cuffs 1934. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 1934 are delimited by a proximal edge 1964 joined directly or indirectly to the topsheet 1924 and/or the backsheet 1925 and a free terminal edge 1966, which is intended to contact and form a seal with the wearer's skin. The barrier leg cuffs 1934 extend at least partially between the front waist edge 1910 and the rear waist edge 1912 of the absorbent article on opposite sides of the longitudinal axis 1980 and are at least present in the crotch region 1907. The barrier leg cuffs 1934 may be joined at the proximal edge 1964 with the chassis of the absorbent article by a bond 1965 which may be made by gluing, fusion bonding, or combination of other suitable bonding processes. The bond 1965 at the proximal edge 64 may be continuous or intermittent. The bond 1965 closest to the raised section of the leg cuffs 1934 delimits the proximal edge 1964 of the standing up section of the leg cuffs 1934.

The barrier leg cuffs 1934 may be integral with the topsheet 1924 or the backsheet 1925 or may be a separate material joined to the absorbent article's chassis. The material of the barrier leg cuffs 1934 may extend through the whole length of the diapers but may be "tack bonded" to the topsheet 1924 towards the front waist edge 1910 and rear waist edge 1912 of the absorbent article so that in these sections the barrier leg cuff material remains flush with the topsheet 1924.

Each barrier leg cuff 1934 may comprise one, two or more elastic strands or strips of film 1935 close to this free terminal edge 1966 to provide a better seal.

In addition to the barrier leg cuffs 1934, the absorbent article may comprise gasketing cuffs 1932, which are joined to the chassis of the absorbent article, in particular to the topsheet 1924 and/or the backsheet 1925 and are placed externally relative to the barrier leg cuffs 1934. The gasketing cuffs 1932 may provide a better seal around the thighs of the wearer. Each gasketing leg cuff may comprise one or more elastic strings 1933 or elastic elements in the chassis of the absorbent article between the topsheet 1924 and backsheet 1925 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 1946 and rear ears 1940. The ears may be an integral part of the chassis, such as formed from the topsheet 1924 and/or backsheet 1925 as side panel. Alternatively, as represented on FIG. 26, the ears (1946, 1940) may be separate elements attached by gluing, heat embossing, and/or pressure bonding. The rear ears 1940 may be stretchable to facilitate the attachment of the tabs 1942 to the landing zone 1944 and maintain the taped diapers in place around the wearer's waist. The rear ears 1940 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 1950 is to quickly acquire the fluid and distribute it to the absorbent core 1928 in an efficient manner. The LMS 1950 may comprise one or more layers, which may form a unitary layer or may remain as discrete layers which may be attached to each other. The LMS 1950 may comprise two layers: a distribution layer 1954 and an acquisition layer 1952 disposed between the absorbent core and the topsheet, but the present disclosure is not limited to such a configuration.

The LMS 1950 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Grace, for example.

The LMS 1950 may comprise a distribution layer 1954. The distribution layer 1954 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 1950 may alternatively or additionally comprise an acquisition layer 1952. The acquisition layer 1952 may be disposed, for example, between the distribution layer 1954 and the topsheet 1924. The acquisition layer 1952 may be or may comprise a non-woven material, such as an SMS or SMMS material, comprising a spunbonded, a melt-blown and a further spunbonded layer or alternatively a carded chemical-bonded nonwoven. The acquisition layer 1952 may comprise air or wet-laid cellulosic, cross-linked cellulosic, or synthetic fibers, or blends thereof. The acquisition layer 1952 may comprise a roll-stock web of synthetic fibers (which may be processed to increase void space, such as by solid state formation), or a combination of synthetic and cellulosic fibers, bonded together to form a highloft material. Alternatively, the acquisition layer 1952 may comprise absorbent open cell foam. The nonwoven material may be latex bonded.

The LMS 1950 of the absorbent article 1900 may comprise channels that may generally enable better conformation of the absorbent article to the wearer's anatomy, leading to increased freedom-of-movement and reduced gapping. One or more of the channels of the LMS 1950 may be configured to work in concert with various channels in the absorbent core 1928, as discussed above. Furthermore, channels in the LMS 1950 may also provide increased void space to hold and distribute urine, BM or other bodily exudates within the absorbent article, leading to reduced leakage and skin contact Channels in the LMS 1950 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the material webs of the present invention may be utilized as a topsheet for a disposable absorbent article, examples of which include the sanitary napkin 1710 and diaper 1900 discussed heretofore.

The material webs of the present disclosure may be used as components of absorbent articles. More than one material web may be used in a single absorbent article. In such a context, the material webs may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) forms the backsheet and a nonwoven web forms the outer cover; a leg cuff; an ear or side panel; a fastener; a waist band; belt or any other suitable portion of an absorbent article. The number of strata in a nonwoven web may also be determined by the nonwoven laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article.

Arrays of Absorbent Articles

As mentioned heretofore, textured nonwoven webs of the present invention may be utilized in a plurality of absorbent articles. Forms of the present invention are contemplated where each in an array of absorbent articles comprise a topsheet, backsheet, and an absorbent core disposed therebetween. The array comprises a first plurality of absorbent articles and a second plurality of absorbent articles. At least one of the first plurality of absorbent articles comprises a textured nonwoven web of the present invention. For example, the first plurality of absorbent articles may comprise a first textured nonwoven web which comprises a first plurality protrusions arranged on a wearer-facing surface of the topsheet. The first textured nonwoven web may comprise a first composition disposed in the first region of the first textured nonwoven web.

Each of the second plurality of absorbent articles comprises a second textured nonwoven web which forms a wearer-facing surface of the topsheet of the second plurality of absorbent articles. The second textured nonwoven web may comprise a second plurality protrusions. Additionally, the second textured nonwoven web may comprise a second composition in the first region of the second textured nonwoven web. The second composition may be different than the first composition. For example, the first composition may be more hydrophilic than the second composition. This may be beneficial where the first plurality of absorbent articles comprises baby diapers or adult incontinence products and where the second plurality of absorbent articles comprises menstrual pads.

In some forms, the first plurality of absorbent articles may comprise a first textured nonwoven web as a topsheet, where the first textured nonwoven web comprises a first plurality of protrusions extending in a negative Z-direction (away from a wearer of the absorbent article). A second plurality of absorbent articles may comprise a second textured nonwoven web which forms a portion of the topsheet of the second plurality of absorbent articles and which comprise a second plurality of protrusions which form a portion of the wearer-facing surface of the absorbent articles.

Forms of the present invention are contemplated where the array comprises additional pluralities of absorbent articles and/or cleaning articles. Such additional pluralities may comprise material webs of the present invention. These material webs may be different than the first material web and/or second material web.

Zones

The protrusions may be provided in zones in the textured nonwoven webs of the present invention. The zones in textured nonwoven webs of the present invention may be positioned in the machine direction, the cross direction, or may be concentric. If a product, such as an absorbent article, has two different zones in the machine direction, the zones may have the same or a similar cross-direction width (e.g., +/−2 mm) for ease in processing. One or more of the zones may have curved or straight boundaries or partial boundaries.

Any suitable number of zones, including more than two, of different or the same zones for a nonwoven web are envisioned within the scope of the present disclosure. The various zones may be in the topsheet as mentioned above, but may also be present on an outer cover or a cuff for example. In some instances, the same or a different pattern of zones of nonwoven webs may be used on the wearer-facing surface (e.g., topsheet) and the garment-facing surface (e.g., outer cover).

In one example, a topsheet or other portion of an absorbent article may have two or more zones in a textured nonwoven web. For example, a first zone of the textured nonwoven web may have a protrusions extending in a positive Z-direction while protrusions in a second zone comprise protrusions extending in a negative Z-direction. The first zone and the second zone may have different functionalities owing to the different orientations of the protrusions. Benefits of such a zoned nonwoven webs can be better use of an absorbent core and more efficient liquid bodily exudate distribution within the absorbent core. This is especially important if an air-felt free core is used in that typical air-felt free cores somewhat struggle with liquid bodily exudate distribution once the liquid bodily exudate is received therein.

Figure 28:
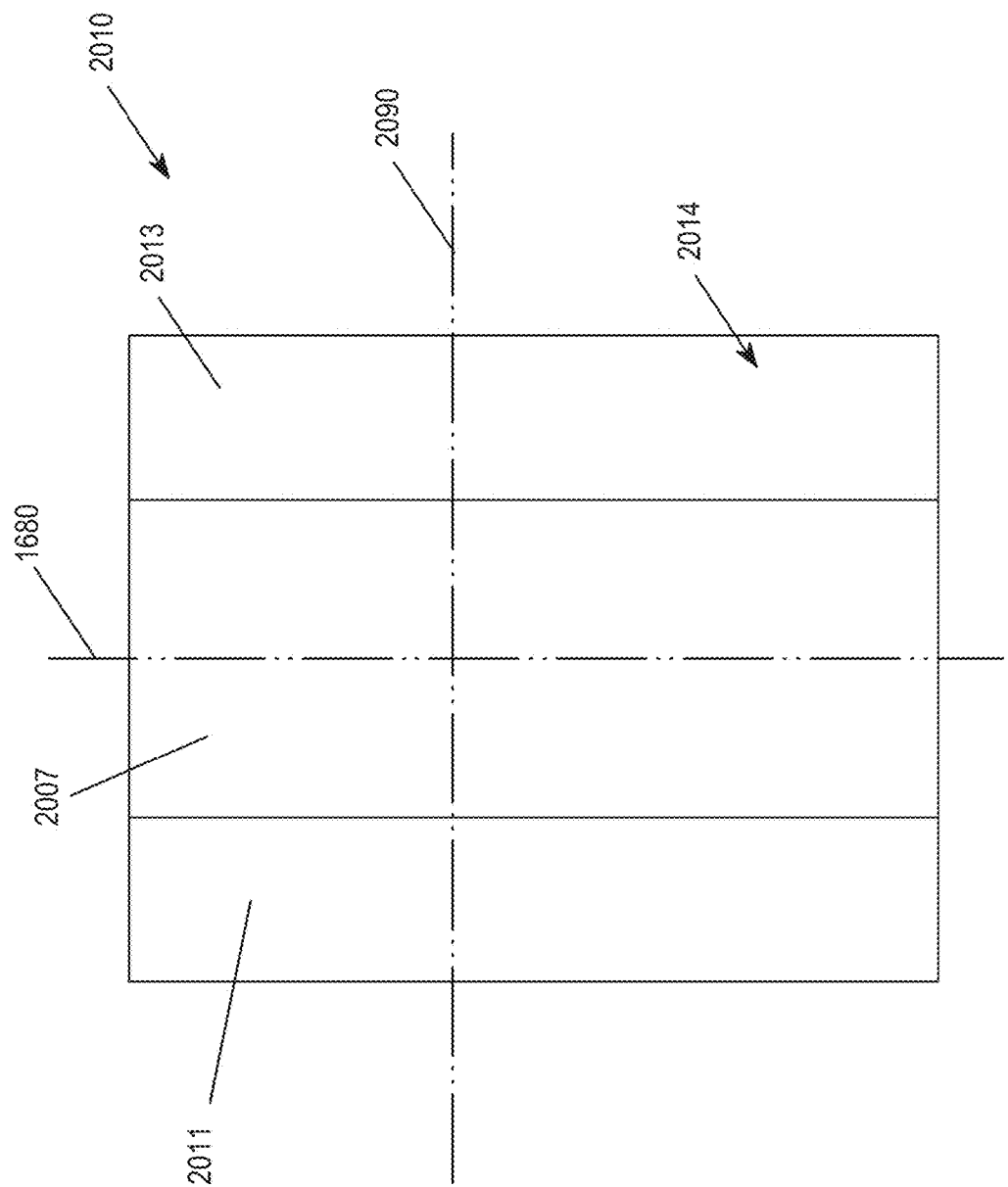
FIGS. 28-32 are schematic plan views of absorbent articles comprising a plurality of zones.

As stated previously, the textured nonwoven webs of the present invention may be utilized in a number of different components of absorbent articles. Referring to FIG. 28, in one specific example, disposable absorbent articles utilizing the nonwoven webs of the present invention may comprise a plurality of zones. As shown, a topsheet 2014 of a disposable absorbent article 2010, may comprise a first zone 2007, a second zone 2011 and a third zone 2013. Absorbent articles may comprise more zones or less zones as described hereafter.

The first zone 2007 may comprise a first plurality of discontinuities, e.g. apertures. As shown the first zone 2007 may have a width parallel to a lateral axis 2090 which does not extend the full width of the topsheet 2014. Instead, the second zone 2011 and the third zone 2013 may be placed on either side of the first zone 2007. In some forms, the first zone 2007 may comprise protrusions while the second zone 2011 and third zone 2013 are sans protrusions. In such forms, the protrusions of the first zone 2007 may be oriented in the negative Z-direction (into the plane of the sheet showing FIG. 28). In addition or independent of the foregoing, the second zone 2011 and the third zone 2013 may comprise a plurality of protrusions which extend in the positive Z-direction. Additionally, differing compositions may be applied across the first zone 2007, second zone 2011, and third zone 2013. For example, the first zone 2007 may comprise a first composition that corresponds to the distal ends and/or sidewalls of the protrusions in the first zone while no composition is applied to the second zone 2011 and third zone 2013. In other example, the second zone 2011 and/or third zone 2013 may comprise a second composition which is different than the first composition. And, the second composition may correspond to the distal ends and/or sidewalls of the protrusions in the second zone 2011 and/or third zone 2013 or may correspond to the first region of the textured nonwoven web in the second zones 2011 and third zones 2013. As a specific example, where the textured nonwoven web is a topsheet, the subjacent acquisition layer generally does not extend widthwise to the same extent as the topsheet. In such configurations, protrusions in the second zone 2011 and third zone 2013 oriented in the negative Z-direction may provide little additional benefit.

Additional configurations of zones are described with regard to FIGS. 29-32. FIGS. 29-32 may represent a portion of a wearer-facing surface of an absorbent article, such as a diaper, an adult incontinence product, and/or a sanitary napkin.

Figure 29:
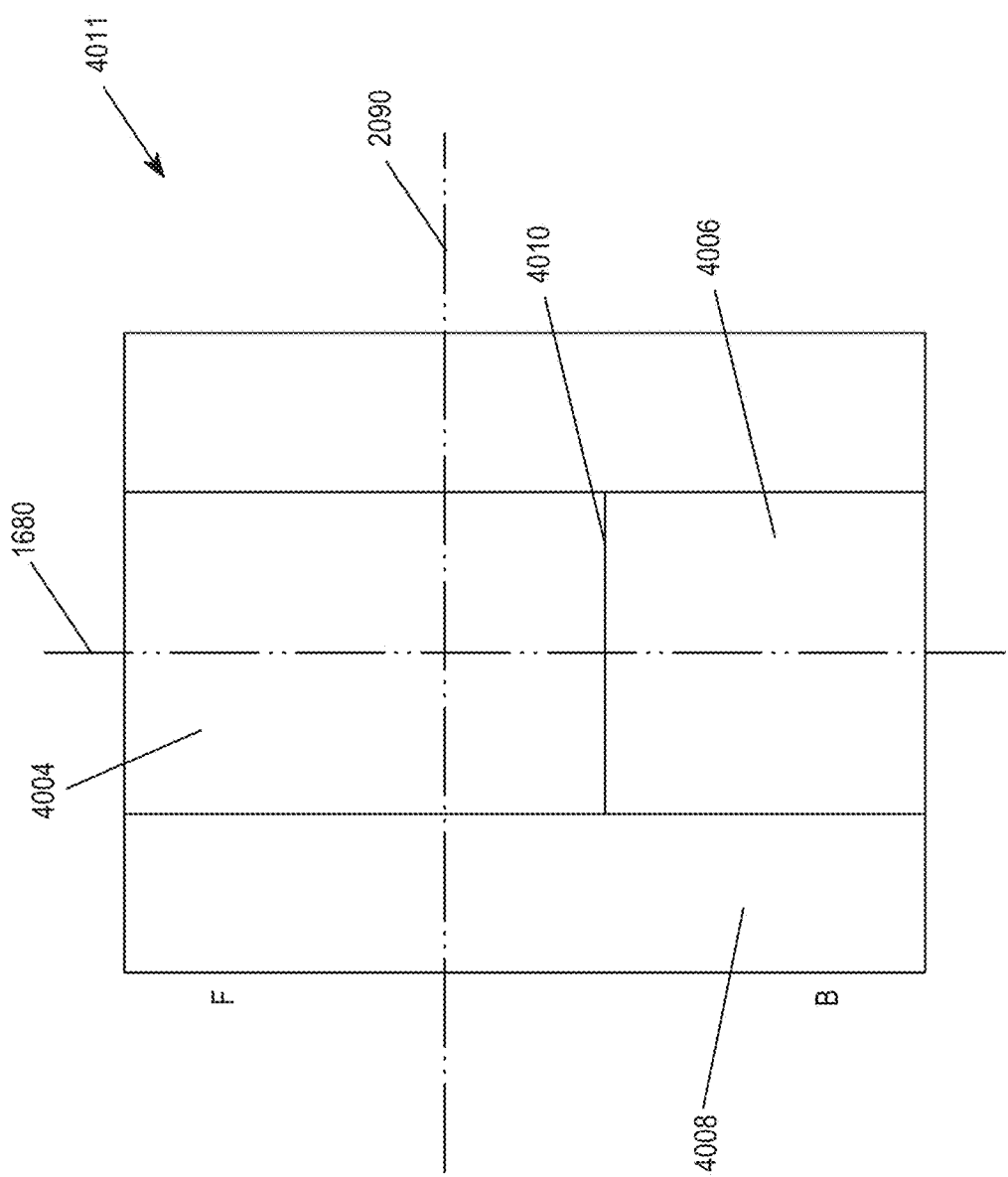

FIG. 29 illustrates an example of a substrate having three zones. The front portion, F, may be positioned in a front portion of an absorbent article or a back portion of an absorbent article. The back portion, B, may be positioned in a front portion of an absorbent article or a back portion of an absorbent article. A first zone 4004 and a second zone 4006 may be positioned intermediate two portions of the third zone 4008. The first zone 4004 may comprise a first plurality of protrusions as described above. The second zone 4006 may comprise a second plurality of protrusions. In some forms, the first composition applied in the first zone 4004 may be different than the second composition applied in the second zone 4006. Additionally, the first composition may be applied to the textured nonwoven web in a different region than the first composition, e.g. first region versus a plurality of discrete second regions. And, in some forms, the protrusions of the first zone 4004 may be oriented in a different direction than those of the second zone. As shown, a substantially-laterally extending separation element, 4010, may extend between the intersection of the first zone 4004 and the second zone 4006.

Figure 30:
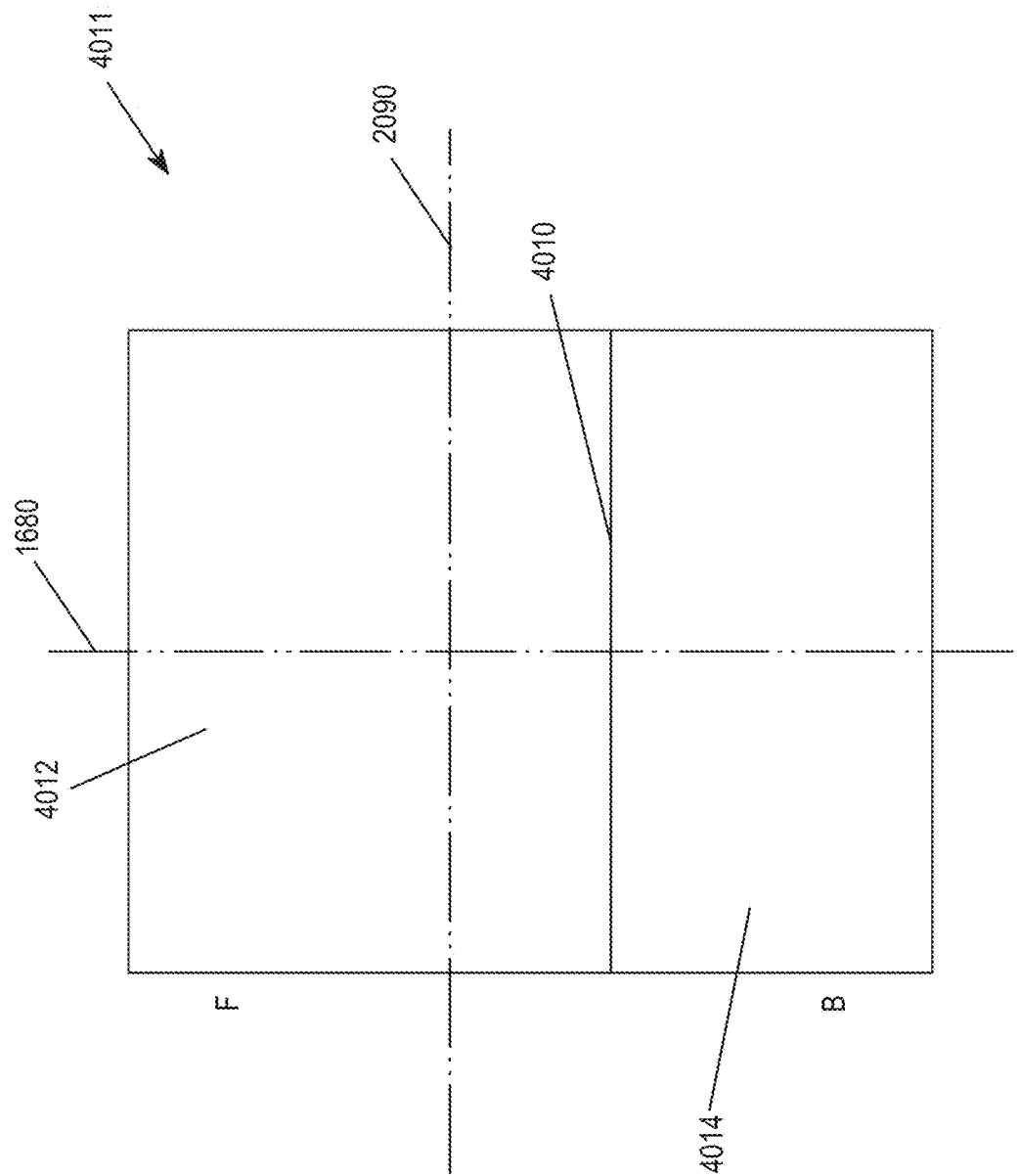

FIG. 30 illustrates an example of a substrate having a first zone 4012 and a second zone 4014. The front portion, F, may be positioned in a front portion of an absorbent article or a back portion of an absorbent article. The back portion, B, may be positioned in a front portion of an absorbent article or a back portion of an absorbent article.

Figure 31:
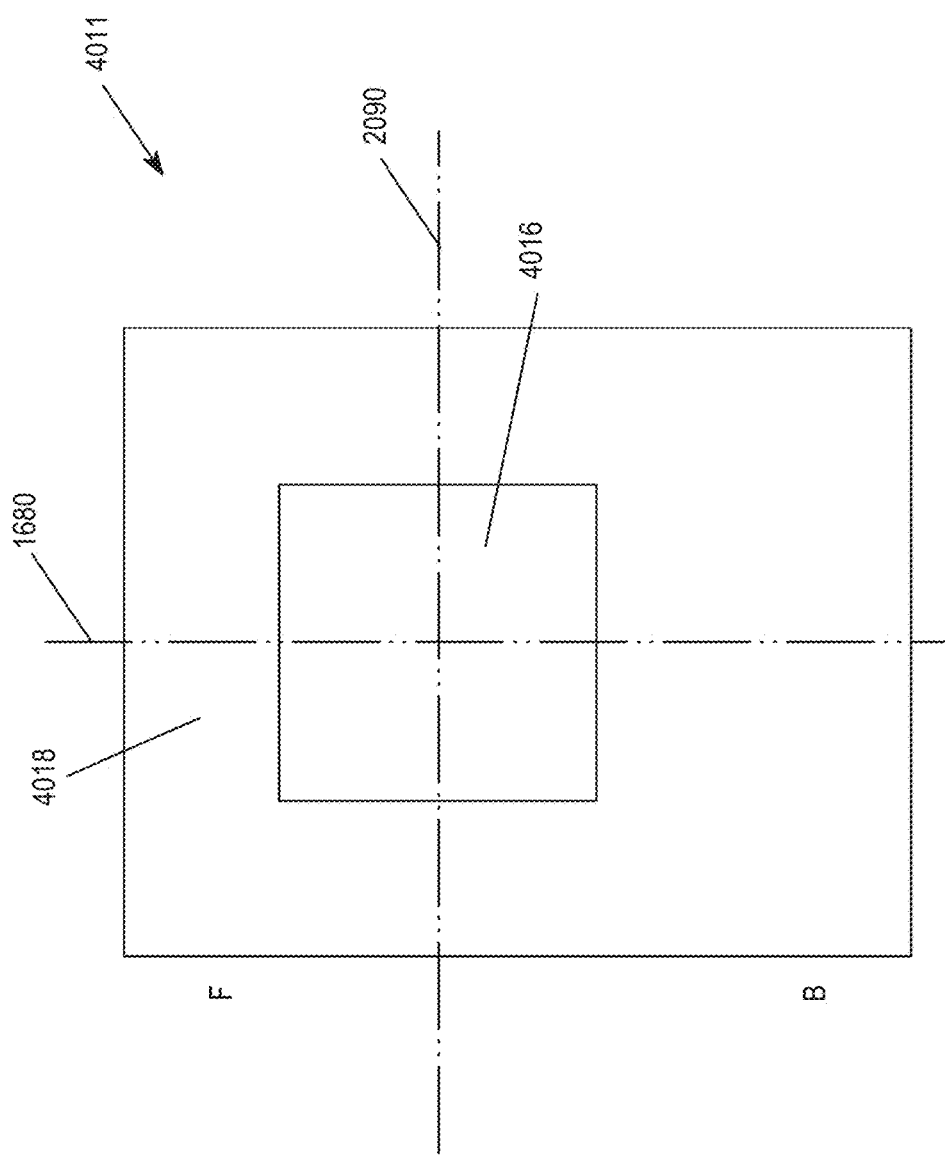

FIG. 31 illustrates an example of a nonwoven web having a first zone 4016 and a second zone 4018. The front portion, F, may be positioned in a front portion of an absorbent article or a back portion of an absorbent article. The back portion, B, may be positioned in a front portion of an absorbent article or a back portion of an absorbent article. The second zone 4018 may at least partially, or fully, surround the first zone 4016.

Figure 32:
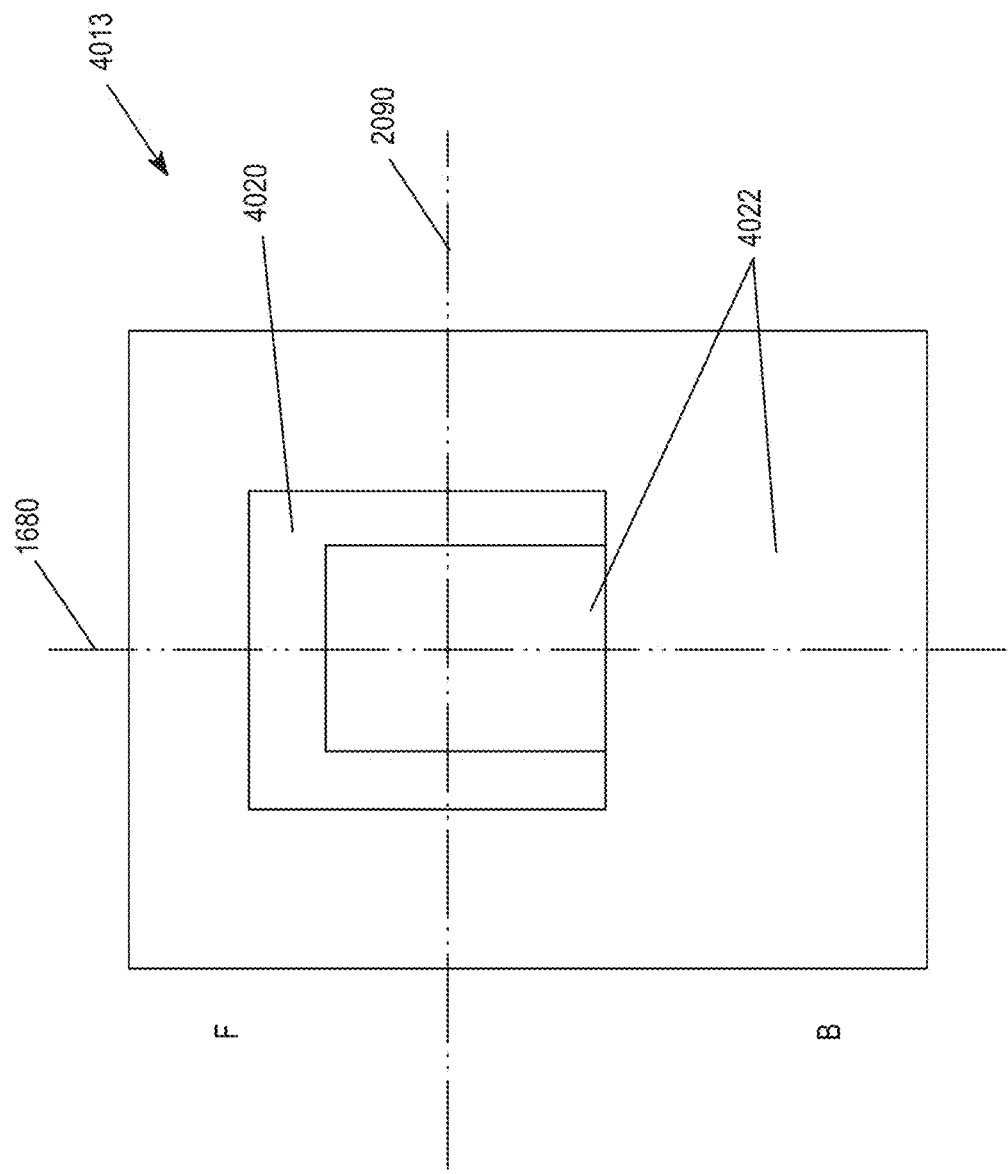

FIG. 32 illustrates an example of a nonwoven web having a first zone 4020 and a second zone 4022. The front portion, F, may be positioned in a front portion of an absorbent article or a back portion of an absorbent article. The back portion, B, may be positioned in a front portion of an absorbent article or a back portion of an absorbent article. The second zone 4022 may at least partially, or fully, surround the first zone 4020.

Regarding the zones of FIGS. 28-32, a myriad of possible configurations may be realized. Some zones may include protrusions while others do not. Some zones may comprise protrusions oriented in the positive Z-direction while others have protrusions oriented in the negative Z-direction. Compositions applied in one zone may be different than compositions applied to in other zones of the textured web. And, the compositions may be applied in different regions of the textured web in addition to the different zones, e.g. first region versus a plurality of discrete second regions.

EXAMPLES

For the following examples 1-5, a topsheet and acquisition layer were attached to each other to form a composite web using H.B. Fuller of St. Paul, Minn., U.S.A. D3166ZP hot melt adhesive applied in the form of spirals with a basis weight of 3 gsm. The topsheet and acquisition layer were simultaneously mechanically deformed by passing them between a pair of intermeshing male and female rolls to provide the topsheet/acquisition layer laminate with protrusions. For examples 1 and 2, the topsheet of the topsheet/acquisition layer laminate was in contact with the female roll and the acquisition layer of the topsheet/acquisition layer laminate was in contact with the male roll. For Examples 3, 4 and 5, the topsheet of the topsheet/acquisition layer laminate was in contact with the male roll and the acquisition layer of the topsheet/acquisition layer laminate was in contact with the female roll. The teeth on the male roll had rounded diamond shape like that shown in FIG. 18B, with vertical sidewalls. The forming elements were 0.186 inch (4.72 mm) long and 0.125 inch (3.18 mm) wide with a CD spacing of 0.300 inch (7.62 mm) and an MD spacing of 0.346 inch (8.79 mm). The recesses in the mating female roll also have a rounded diamond shape, similar to that of the male roll, with a clearance between the rolls of 0.032-0.063 inch (0.813-1.6 mm). The process speed was run at 61 meters/minute and the depth of engagement (DOE) was 0.135 inch (3.43 mm).

The topsheet of the topsheet/acquisition layer laminate was a hydrophilic coated PE/PP sheath/core bicomponent nonwoven material with a basis weight of 28 gsm by Fitesa of Simpsonville, S.C., U.S.A. Such a material is described in Fitesa's U.S. patent application Ser. No. 14/206,699 entitled "Extensible Nonwoven Fabric". The average fiber diameter of the topsheet is 17.5 microns or 2 denier. The fiber diameter is determined using an average of 10 measurements made under a light microscope. The fiber denier can be calculated from the fiber diameter using the following equation: Fiber denier=Cross-sectional area (in $m^2$)*density (in $kg/m^3$)*9000 m*1000 g/kg.

$$\text{Cross-sectional area} = \frac{(\pi * D^2)}{4}$$

where D is the diameter.

The density for a 50/50 polyethylene/polypropylene bi-component fiber, for example, may be taken as 925 $kg/m^3$. The nonwoven material was first coated with a finish made of a fatty acid polyethylene glycol ester for the production of a permanent hydrophilic nonwoven material. The topsheet of the topsheet/acquisition layer laminate had a width of 168 mm.

The acquisition layer of the topsheet/acquisition layer laminate was an air through bonded nonwoven with a basis weight of 65 gsm. The acquisition layer comprised 4 denier coPET/PET (polyethylene terephthalate) bicomponent fibers which was treated with a surfactant. The acquisition layer of the topsheet/acquisition layer laminate had a width of 90 mm.

For some of the examples, as shown in Table 1, after the topsheet and acquisition layer were mechanically deformed, the topsheet of the topsheet/acquisition layer laminate was coated with GTM (glycerol trimyristate) using a slot coater that was located downstream of the male and female rolls. The amount of GTM applied to the web was varied by varying the pump speed of the pump feeding the slot coater. For Examples 1 and 2, the protrusions contacted the slot coater and the GTM was applied primarily to the distal ends of the protrusions and not to the sidewalls of the protrusions or the planar area between the protrusions. For Examples 3-5, the second surface of the web that comprises base openings from the protrusions contacted the slot coater and the GTM was applied primarily to the planar region surrounding the base openings and not to the interior of the protrusions. The GTM basis weight applied to the web was calculated using the following formula:

Basis weight (grams per square meter)=GTM flow rate (grams/minute)/(Web speed (meters/minute)×Slot coat width (meters)×Portion of Coated Area), where the Portion of Coated Area for the protrusion side (Examples 1 and 2) was 0.3 and the Portion of Coated Area for the planar side with the base openings (Examples 3, 4 and 5) was 0.75.

TABLE 1

| | Protrusion Orientation | Calculated GTM Basis Weight (gsm) |
|---|---|---|
| Example 1 | Protrusion towards body | 0 |
| Example 2 | Protrusion towards body | 34.3 |
| Example 3 | Protrusion towards core | 0 |
| Example 4 | Protrusion towards core | 6.1 |
| Example 5 | Protrusion towards core | 13.7 |

Prototype Diapers for the Examples

Diaper prototypes incorporating the above Examples were produced using the materials of Pampers® New Baby S2 (size 2) diaper commercially available in Germany Pampers® New Baby S2 (size 2) diaper comprises a topsheet, an acquisition layer beneath the topsheet, a distribution layer beneath the acquisition layer, an absorbent core between the distribution and a backsheet beneath the absorbent core. The commercial topsheet and acquisition layer of the Pampers® New Baby diaper were replaced with the example topsheet acquisition layer laminates described above. For each diaper prototype a hot melt adhesive was applied on the side of the diaper core and the carrier layer/distribution layer composite was placed with the distribution layer side facing the core on top of it, so that the edge of the carrier layer was 40 mm from the diaper chassis front edge with respect to the MD and centered with respect to the CD direction.

The carrier layer of the carrier layer/distribution layer laminate was a hydrophilically coated PP (polypropylene) nonwoven material, composed of two spunlaid and two meltblown layers (SMMS). The basis weight of the carrier layer was 8 gsm. The material was consolidated and thermopoint-bonded, then it was coated with a finish made of a mixture of cationic surfactants to render the carrier layer hydrophilic. The carrier layer had a width of 105 mm and a length of 259 mm.

The distribution layer of the carrier layer/distribution layer laminate was composed of intra-fiber crosslinked cellulose fibers, polyacrylic acid was used as cross-linking agent. The distribution layer has a basis weight of 200 gsm. The distribution layer had a width of 80 mm and a length of 239 mm. The distribution layer and carrier layer were attached to each other with a hot melt adhesive applied in form of spirals with a basis weight of 2.2 gsm, the distribution layer was centered in MD and CD with respect to the carrier layer.

A hot melt adhesive was applied on the side of the carrier layer and the topsheet/acquisition layer laminate was placed with the acquisition layer side facing the carrier layer on top of it, so that the edge of the acquisition layer was 40 mm from the diaper chassis front edge with respect to MD and centered with respect to CD direction. The hot melt adhesive was applied in form of spirals with a basis weight of 5 gsm.

Each prototype diaper was compacted in a bag at an In Bag Stack Height, i.e. the total caliper of 10 bi-folded diapers, of 90 mm for 1 week at 23° C.+/−2° C. and 50%+/−10% Relative Humidity (RH). Then the bag was opened and the diapers out of the bag were conditioned at least 24 hours prior to any testing at 23° C.+/−2° C. and 50%+/−10% Relative Humidity (RH).

Experimental Results

The data was measured according to the respective Flat acquisition and Post Acquisition Collagen Rewet test methods as disclosed herein. The size 2 protocols were used. The data provided below in Table 2 reflects those topsheet/acquisition layer laminates with protrusions facing toward the user—(tufts up).

TABLE 2

| Option | Example 1 | | Example 2 | |
|---|---|---|---|---|
| Protrusion Orientation | Towards body | | Towards body | |
| Calculated GTM Basis Weight (gsm) | 0 | | 34.3 | |
| | Avg | Stdev | Avg | Stdev |
| First Gush Acquisition Time, sec | 9.3 | 1.5 | 9.3 | 1.3 |
| Second Gush Acquisition Time, sec | 12.8 | 2.2 | 13.8 | 1.5 |
| Third Gush Acquisition Time, sec | 19.0 | 3.6 | 20.5 | 3.8 |
| Fourth Gush Acquisition Time, sec | 24.5 | 5.1 | 24.3 | 1.3 |
| Flat acquisition-Total times [s] | 65.6 | 11.7 | 67.9 | 6.6 |
| Post acquisition collagen Rewet [mg] | 258.3 | 5.7 | 193.0 | 7.3 |

The data of Table 2 demonstrates that coating of the distal ends of the protrusions did not impact the speed of acquisition to a large extent. However, the coating of the distal ends did improve the rewet performance of the absorbent article which in turn improves dryness.

The data provided below in Table 3 reflects those topsheet/acquisition layer laminates with protrusions facing toward the absorbent core—(tufts down).

TABLE 3

| Option | Example 3 | | Example 4 | | Example 5 | |
|---|---|---|---|---|---|---|
| Protrusion Orientation | Towards core | | Towards core | | Towards core | |
| Calculated GTM Basis Weight (gsm) | 0 | | 6.1 | | 13.7 | |
| | Avg | Stdev | Avg | Stdev | Avg | Stdev |
| First Gush Acquisition Time, sec | 11.0 | 0.8 | 12.5 | 0.6 | 14.0 | 0.8 |
| Second Gush Acquisition Time, sec | 17.0 | 1.2 | 18.8 | 2.5 | 18.8 | 1.3 |
| Third Gush Acquisition Time, sec | 26.5 | 2.6 | 26.5 | 4.2 | 25.3 | 1.3 |
| Fourth Gush Acquisition Time, sec | 33.8 | 5.6 | 36.3 | 8.7 | 31.0 | 3.5 |
| Flat acquisition - Total times [s] | 88.3 | 10.0 | 94.1 | 15.6 | 89.1 | 5.8 |
| Post acquisition collagen Rewet [mg] | 281.5 | 7.6 | 232.5 | 9.7 | 130.5 | 3.3 |

Recall that for samples 4 and 5, GTM was provided on the second surface of the topsheet/acquisition layer laminate—the second surface is the wearer-facing surface for examples 3-5. As shown, the addition of GTM negatively impacted the fluid acquisition time by a few seconds for the first gush. The fluid acquisition times, particularly for example 5—the highest loaded GTM—the fluid acquisition times more closely matched those of the untreated example 3 for subsequent liquid insults. And, the rewet performance of example 5 was much better than the rewet performance of either example 3 or example 4.

While conventional wisdom would generally not look favorably upon a hydrophobically treated topsheet, the above examples 4 and 5 demonstrate that these hydrophobically treated topsheets may perform on par, generally, with the untreated example 3. Additionally, conventional wisdom may suggest that in order for a hydrophobic topsheet to properly operate, apertures must be provided to allow quick access to more hydrophilic layers beneath the topsheet. However, the data of Table 3 contradicts that notion as well. Recall that the base openings are not apertures. Instead, they are simply openings which lead to the inner surfaces of the protrusions. So, the hydrophobically treated example 5, even without apertures, provides reasonable fluid acquisition speeds while greatly reducing rewet.

Additional data was collected via the SEM Method for determining contact angle on fibers (described in detail hereafter) on the Examples 1-5 mentioned heretofore in Tables 1-3. See Table 6 regarding the SEM water contact angle data.

TABLE 6

|  | Protrusion Orientation | Calculated GTM Basis Weight (gsm) | Water Contact angle on the distal end (std dev.) | Water Contact angle on the land region (std dev.) | Water Contact angle on the "wall" region (std dev.) |
| --- | --- | --- | --- | --- | --- |
| Example 1 | Protrusion towards body | 0 | 64.9 (9.0) | n.a. | n.a. |
| Example 2 | Protrusion towards body | 34.3 | 109.9 (15.0) | 62.5 (11.9) | 69 (11.5) |
| Example 3 | Protrusion towards core | 0 | n.a. | n.a. | n.a. |
| Example 4 | Protrusion towards core | 6.1 | n.a. | n.a. | n.a. |
| Example 5 | Protrusion towards core | 13.7 | 58.7 (14.9) | 83.1 (15.7) | n.a. |

Test Methods

Unless indicated otherwise, all tests described herein are made with samples conditioned at least 24 hours at 23° C.+/−2° C. and 50%+/−10% Relative Humidity (RH). Densities are referred at 2.1 kPa.

Ratio of Protrusion Circumference to Length of Second Surface Opening

Figure 33:
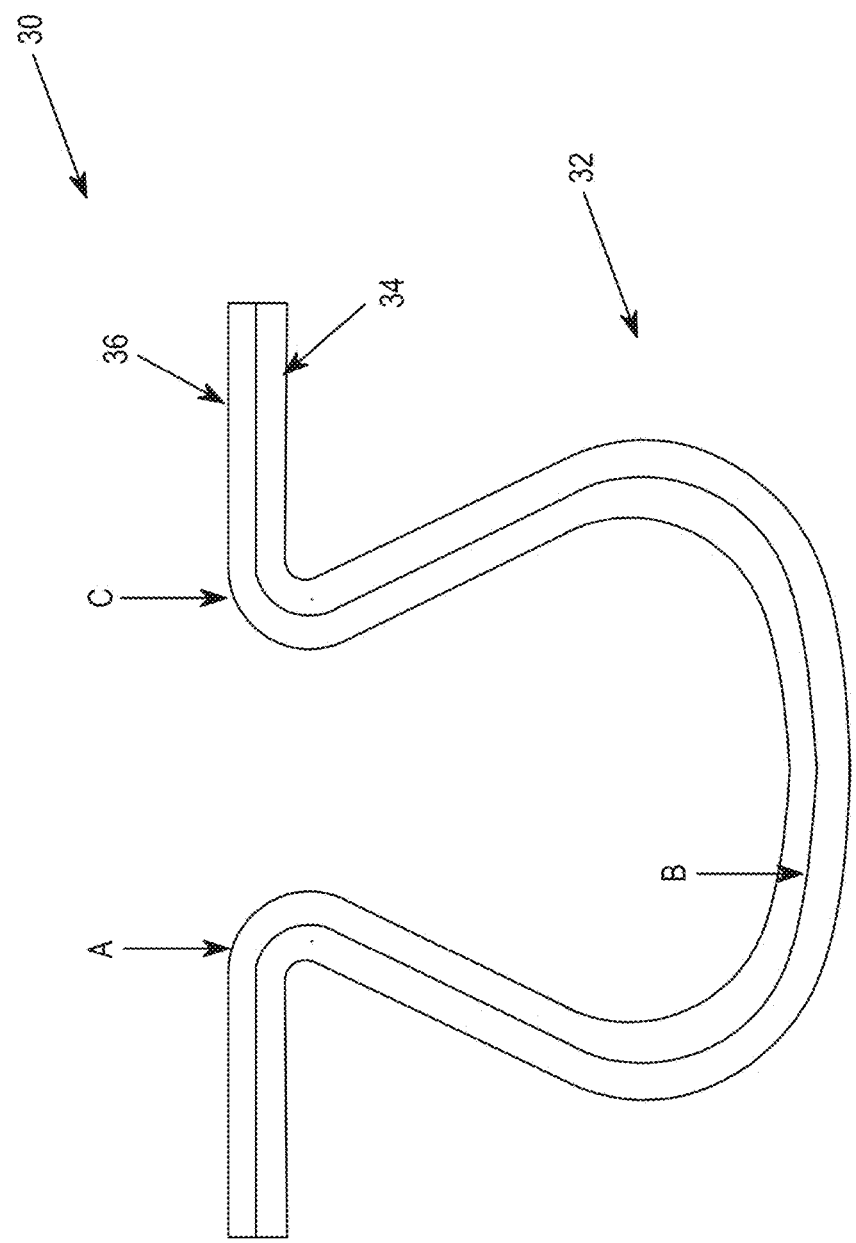
FIG. 33 is a schematic view of the protrusion shown in FIG. 7.

Referring to FIG. 33, to measure the loop circumference length, arrange the textured nonwoven web 30 comprising the protrusions 32 so that the viewing direction is co-linear with the longitudinal axis (MD) of the protrusion 32. Using a microscope, adjust the magnification so that one protrusion 32 is completely in view. If necessary, a cross-section of the protrusion 32 can be obtained by cutting the protrusion 32 perpendicular to the longitudinal axis using sharp scissors or a razor blade, taking care in preserving the overall geometry of the protrusion while cutting it. Measure and record the loop circumference length by starting the measurement at a first origination point A, proceeding along the median path of the loop fibers B, and terminating the measurement at the second origination point C. Measure and record the base length of the second surface opening 64, parallel to the second surface 36 between the first origination point A and the second origination point C. The loop base length of the second surface opening 64 is measured parallel to the plane of the web and may be at the plane of the web or above the plane of the web. The protrusions are measured where the protrusions are not under any pressure or strain.

Flat Acquisition Test Method

This method determines the acquisition times of a baby diaper. The method settings are depending on the diaper size tested. Table 4 shows commonly used diaper size descriptions to be used as reference.

TABLE 4 commonly used size descriptions for diapers

| Size | Alternative Size Descriptions | | |
| --- | --- | --- | --- |
| 1 | newborn | | |
| 2 | S | P | Infant |
| 3 | M | | Crawler |

TABLE 4-continued commonly used size descriptions for diapers

| Size | Alternative Size Descriptions | | |
| --- | --- | --- | --- |
| 4 | L | G | Toddler |
| 5 | XL | XG | Walker |
| 6 | XXL | XXG | Junior |

Apparatus

Figure 34:
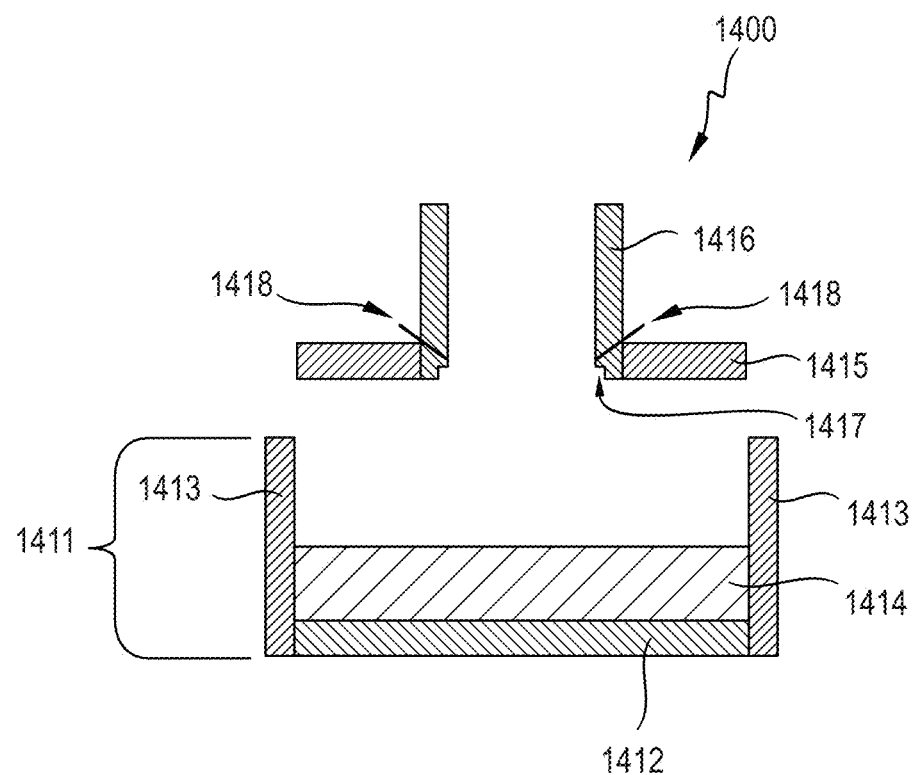
FIG. 34 shows an equipment assembly used in the Flat Acquisition Test Method.

The test apparatus 1400 is shown in FIG. 34 and comprises a trough 1411 made of polycarbonate (e.g. Lexan®) nominally 12.5 mm (0.5 inch) in thickness. The trough 1411 comprises a rectilinear horizontal base 1412 having a length of 508 mm (20.0 inches), and a width of 152 mm (6.0 inches). Two rectilinear vertical sides 1413, 64 mm (2.5 inches) tall×508 mm (20 inches) in length are affixed to the long edges of the base 1412 to form a U-shaped trough 1411 having a length of 508 mm (20.0 inches), an internal width of 152 mm (6.0 inches), and an internal depth of 51 mm (2.0 inches). The front and back ends of the trough 1411 are not enclosed.

A slab of open-cell polyurethane foam 1414 with dimensions 508×152×25 mm is wrapped in polyethylene film and placed in the bottom of the trough 1411 in such a way that the edges of the foam 1414 and the trough 1411 are aligned, and the upper surface of the polyethylene film is smooth and free of seams, wrinkles or imperfections. The polyurethane foam 1414 has a compression hardness at 40% compression $CV_{40}$ of 2.4 kPa+/−0.4 kPa as determined according to DIN EN ISO 3386 and a density of 16 kg/m³+/−2 kg/m³ as determined according to DIN EN ISO 845, e.g. a film wrapped foam can be purchased from Crossroads Machine Inc., Englewood Ohio 45322, USA under the description of "FOAM BASE FOR LIQUID ACQUISITION TEST", or equivalent film-wrapped foam may be used. A reference line is drawn across the width of the upper surface of the polyethylene cover 121 mm (6.0 inches) from one end (the front edge) parallel to the transverse centerline using an indelible marker: such reference line distance must be adjusted according to size based on the table 1.

A rectilinear polycarbonate top plate 1415 has a nominal thickness of 12.5 mm (0.5 inch), a length of 508 mm (20.0 inches), and a width of 146 mm (5.75 inches). A 51 mm (2.0 inch) diameter hole is bored in the center of the top plate 1415 (i.e. the center of the hole is located at the intersection of the longitudinal and transverse axes of the upper surface of the top plate 1415). A polycarbonate cylinder 1416 with an outside diameter of 51 mm (2.0 inches), an internal diameter of 37.5 mm (1.5 inches) and a height of 102 mm (4.0 inches) is glued into the hole in the top plate 1415 so that the bottom edge of the cylinder 1416 is flush with the lower surface of the top plate 1415 and the cylinder 1416 protrudes vertically 89 mm (3.5 inches) above the upper surface of the top plate 1415, and the seam between the cylinder 1416 and the top plate 1415 is watertight. An annular recess 1417 with a height of 2 mm (0.08 inch) and a diameter of 44.5 mm (1.75 inches) is machined into the bottom internal edge of the cylinder 1416. A nylon wire mesh (the opening of this nylon mesh is 1.5 mm, the nylon wire diameter is 0.5 mm) is glued into the recess 1417. The mesh is prepared via cutting a circle of 44.5 mm diameter and cutting of 5 mm of the diameter at each opposite side (i.e. 180° apart). Two 1 mm diameter holes are drilled at a 45° angle to the upper surface of the top plate 1415 so that the holes intersect the inner surface of the cylinder 1416 immediately above the recess 1417 and are at opposite sides of the cylinder 1416 (i.e. 180° apart). Two stainless steel wires 1418 having a diameter of 1 mm are glued into the holes in a watertight fashion so that one end of each wire is flush with the inner cylinder wall and the other end protrudes from the upper surface of the top plate 1415. These wires are referred to as electrodes herein below. A reference line is scribed across the width of the top plate 1415 at a specific distance from the front edge parallel to the transverse centerline. The distance is size specific and shown in table 2 below. For example 121 mm is the distance for size 4. The top plate 1415/cylinder 1416 assembly has a weight of approximately 1180 grams.

TABLE 5

Size specific distances, gush volumes and rates

| Size | Reference line distance [mm] | Gush volume [ml] | Gush rate [ml/s] |
|------|------|------|------|
| 1 | 160 | 24 | 8 |
| 2 | 147 | 40 | 8 |
| 3 | 134 | 50 | 10 |
| 4 | 121 | 75 | 15 |
| 5 | 121 | 75 | 15 |
| 6 | 121 | 75 | 15 |

Two steel weights each weighing 4.5 Kg and measuring 146 mm (5.75 inches) wide, 38 mm (1.5 inches) deep, and approximately 100 mm (4 inches tall) are also required.

Procedure

All testing is carried out at 23±2° C. and 50±10% relative humidity.

The polycarbonate trough 1411 containing the wrapped foam slab 1414 is placed on a suitable flat horizontal surface. A disposable absorbent product is removed from its packaging and the cuff elastics are cut at suitable intervals to allow the product to lay flat. The product is weighed to within ±0.1 grams on a suitable top-loading balance then placed on the covered foam slab 1414 in the acquisition apparatus with the front waist edge of the product aligned with the reference mark on the polyethylene cover. The product is centered along the longitudinal centerline of the apparatus with the topsheet (body-side) of the product facing upwards and the rear waist edge toward the rear end of the foam slab 1414. The top plate 1415 is placed on top of the product with the protruding cylinder facing upwards. The scribed reference line is aligned with the front waist edge of the product and the rear end of the top plate 1415 is aligned with the rear edge of the foam slab 1414. The two 4.5 Kg weights are then gently placed onto the top plate 1415 so that the width of each weight is parallel to the transverse centerline of the top plate, and each weight is 83 mm (3.25 inches) from the front or rear edge of the top plate 1415. The point of the topsheet of the product falling at the center of the cylinder is marked as loading point of the article.

A suitable electrical circuit is connected to the two electrodes to detect the presence of an electrically conductive fluid between them.

A suitable pump; e.g. Model 7520-00 supplied by Cole Parmer Instruments, Chicago, USA, or equivalent; is set up to discharge a 0.9 mass % aqueous solution of sodium chloride through a flexible plastic tube having an internal diameter of 4.8 mm (3/16 inch), e.g. Tygon® R-3603 or equivalent. The end portion of the tube is clamped vertically so that it is centered within the cylinder 1416 attached to the top plate 1415 with the discharge end of the tube facing downwards and located 50 mm (2 inches) below the upper edge of the cylinder 1416. The pump is operated via a timer and is pre-calibrated to discharge a gush of 75.0 ml of the 0.9% saline solution at a rate of 15 ml/sec (for size 4 or equivalent). The volume and rate to be used for specific sizes is illustrated in the table 1 above.

In the following the case of size 4 is exemplified: for other sizes the only difference will be to replace the reference line distance, gush volume and gush rate for the specific size as defined in the table 1. The pump is activated and a timer started immediately upon activation. The pump delivers 75 mL of 0.9% NaCl solution to the cylinder 1416 at a rate of 15 ml/sec, then stops. As test fluid is introduced to the cylinder 1416, it typically builds up on top of the absorbent structure to some extent. This fluid completes an electrical circuit between the two electrodes in the cylinder. After the gush has been delivered, the meniscus of the solution drops as the fluid is absorbed into the structure. When the electrical circuit is broken due to the absence of free fluid between the electrodes in the cylinder, the time is noted.

The acquisition time for a particular gush is the time interval between activation of the pump for that gush, and the point at which the electrical circuit is broken.

Four gushes are delivered to the product in this fashion; each gush is 75 ml and is delivered at 15 ml/sec. The time interval between the end of a certain gush, i.e. when the electrical circuit is broken after the liquid acquisition, and the beginning of the next gush is 300 seconds.

The acquisition time for four gushes is recorded to the nearest 1.0 s. Eight products for each option are tested in this fashion and the average gush time for each of the respective gushes (first through fourth) is calculated.

A new foam base 1414 is taken for each test or let the foam base relax for at least 24 hours before re-using it.

The total acquisition time is the sum of the acquisition time of gush 1, the acquisition time of gush 2, the acquisition time of gush 3 and the acquisition time of gush 4. The total acquisition time is expressed in seconds.

Post Acquisition Collagen Rewet Test Method

This method requires a collagen film having a Fixed Height Frit Absorption (FHFA-0 cm) between 0.48 g/g and 0.66 g/g and FHFA −20 cm between 0.15 g/g and 0.21 g/g as measured according to the method described below. The collagen film has also a basis weight of 31.5+/−3.5 g/m². The collagen film can be purchased from Viscofan Group, 31192 Tajonar-Navarra, Spain, under the designation of Naturin COFFI clear, or equivalent material having the characteristics and basis weight as described above.

Before executing the test, the collagen film as is prepared by being cut into circular sheets of 90 mm (3.54 inches) diameter e.g. by using a sample cutter device, and by equilibrating the film in the controlled environment of the test room (see Flat Acquisition Test Method) for at least 12 hours (tweezers are to be used for all handling of the collagen film).

At least 5 minutes, but not more than 6 minutes after the last gush, which has been performed in the above Flat Acquisition Test Method, is absorbed, the cover plate and weights are removed, and the test sample is carefully placed flat on a lab bench.

Figure 35:
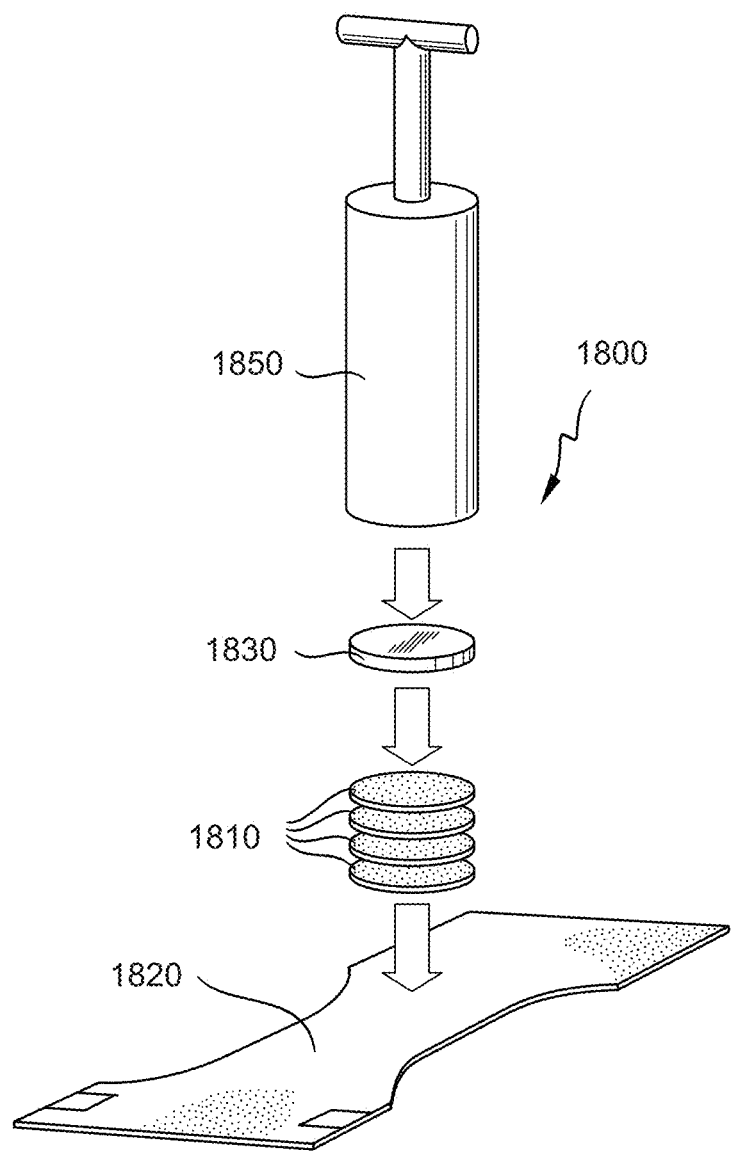
FIG. 35 shows an equipment assembly used in the Post Acquisition Collagen Rewet Test Method.

Four sheets of the precut and equilibrated collagen material (1810) are weighed with at least one milligram accuracy, and then positioned centered onto the loading point of the article, as defined in the Flat Acquisition Test Method, and covered by a plate (1830) made of Poly(methyl methacrylate) (PMMA) (e.g. Perspex®) of 90 mm (3.54 inches) diameter, and about 20 mm (0.78 inches) thickness. A weight (1850) of 15 kg is carefully added (also centered). After 30+/−2 seconds the weight and Perspex plate are carefully removed again, and the collagen films are reweighed (See the system 1800 in FIG. 35).

The Rewet result is the moisture pick up of the collagen film, expressed in mg. Four products for each option are tested in this fashion and the average rewet is calculated.

Fixed Height Frit Absorption (FHFA) at 20 cm and at 0 cm Test Methods

This test is suitable of measuring the uptake of a material under the conditions of suction pressures of 20 cm or of 0 cm of fluid, for example of a saline solution (0.9% wt. NaCl solution) after 30 s.

Figure 36:
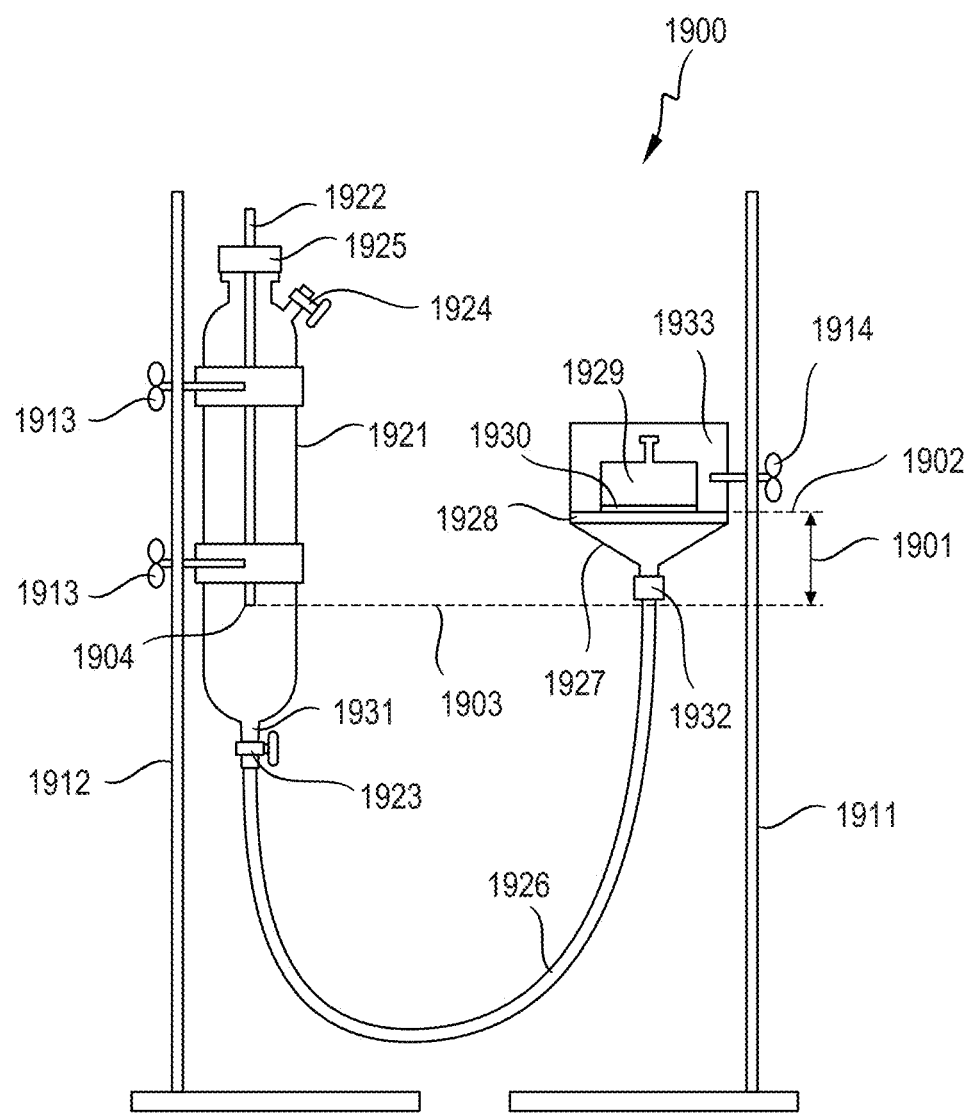
FIG. 36 shows an equipment assembly used in the Fixed Height Frit Absorption (FHFA) Test Methods.

General Apparatus Setup:

FIG. 36 shows the FHFA measurements setup 1900: a suitable fluid delivery reservoir 1921, has an air tight stopcock 1924 to allow the air release during the filling of the equipment. An open-ended glass tube 1922 having an inner diameter of 10 mm extends through a port 1925 in the top of the reservoir such that there is an airtight seal between the outside of the tube and the reservoir, this allows maintaining the required zero level of the hydro head during the experiment regardless the amount of liquid in the reservoir. Reservoir 1921 is provided with delivery tube 1931 having an inlet at the bottom of the reservoir, a stopcock 1923, with the outlet connected to the bottom 1932 of the sample holder funnel 1927 via flexible plastic tubing 1926 (e.g. Tygon®). The Fluid reservoir is firmly held in position by means of standard lab clamps 1913 and a suitable lab support 1912. The internal diameter of the delivery tube 1931, stopcock 1923, and flexible plastic tubing 1926 enables fluid delivery to the sample holder funnel 1927 at a high enough flow rate such that such flowrate is higher than the flowrate absorbed by the collagen sample in the conditions of the experiment and exclude that the measured uptake is limited by the fluid flowrate supplied by the equipment system. The reservoir 1921 has a capacity of approximately 1 liter. Other fluid delivery systems may be employed provided that they are able to deliver the fluid to the sample holder funnel 1927 maintaining the zero level of the hydrostatic liquid pressure 1903 at a constant height during the whole experiment.

The sample holder funnel 1927 has a bottom connector with an internal diameter of 10 mm, a measurement and a chamber 1933 where a glass frit 1928 is accommodated. The sample holder chamber has a suitable size to accommodate the sample 1930 and the confining pressure weight 1929. The frit is sealed to the wall of the chamber 1933. The glass frit has pore of specific size of 16-40 μm (glass frit type P 40, as defined by ISO 4793) and a thickness of 7 mm.

The confining pressure weight 1929 is a cylinder with a diameter identical to the sample size (6 cm) and a weight of 593.94 g so to apply exactly 2.06 kPa of confining pressure to the sample 1930. The sample holder funnel 1927 is precisely held in position using a suitable lab support 1911 through a standard lab clamp 1914. The clamp should allow an easy vertical positioning of the sample holder funnel 1927 such that the top of the glass frit 1928 can be positioned at a) the same height (+/−1 mm) of the bottom end 1904 of the open ended glass tube 1922 and b) exactly 20 cm (+/−1 mm) above the bottom end 404 of the open ended glass tube 1922. Alternatively two separated clamps are positioned at the abovementioned setups a and b and the sample holder funnel is alternatively moved from one to the other. During the non-usage time, the instrument is kept in proper operating conditions flooding the sample holder funnel 1927 with an excess of liquid to guarantee a proper wetting of the glass frit 1928 that should be completely below the liquid level. The sample holder funnel 1927 is also covered with an air tight cap (not shown) to avoid evaporation and therefore a change in solution salinity. During storage stopcocks 1923 and 1924 are also accordingly closed to avoid evaporation as well as the open ended tube 1922 air tight sealed with a cap (not shown).

Sample Preparation

During the sample preparation, the sample is only touched with the tweezers. Discs of 6 cm diameter are cut out of the collagen material using any suitable die cutter. The samples are then stored in a closed container, e.g. a petri dish with lid, and conditioned in the controlled environment of the test room for at least 24 hours.

Material Used:
Saline solution at a concentration of 0.9% by weight
FHFA equipment (as set out above)
Bubble level
Analytical balance with a resolution of ±0.001 g with air draft protections.
Funnel
Tweezers
Timer Experiment Setup
Before starting the experiment:
1) The caps to the open ended tube 1922 and the sample holder funnel 1927 are removed.
2) Ensuring the stopcock 1923 is closed, the stopcock 1924 is opened to allow the air to flow out of the liquid reservoir as displaced by liquid during the refilling phase. The liquid reservoir 1921 is refilled through top end of the open-end tube 1922 with the 0.9% Saline solution with the help of suitable means such a funnel (not shown) at the end of the filling the stopcock 1924 is closed.
If during all the experiments the liquid level would be close to the bottom 1904 of the open-ended tube 1922, before running the next sample, the liquid reservoir must be refilled repeating this step number 2.
3) The sample holder funnel 1927 is removed from the lab clamp 1914 and the excess of liquid is removed pouring it away.
4) Manually holding the sample holder funnel 1927 such that the top of the glass frit 1928 lies around 20 cm below the bottom end 1904 of the open-ended tube 1922 the stop cock 1923 is carefully open until the air liquid interface in the open ended tube 1922 reaches the bottom end 1904 and a few bubble of air escape from tube 1922. At this point the stop cock 1923 is closed.

5) The excess of liquid now present in the sample holder funnel 1927 is again disposed and the system is now ready to start the measurements.

For measuring the Fixed Height Frit Absorption (FHFA) at 20 cm, for each replicate:

1) The sample holder is positioned on the clamp 414 such that the top of the glass frit 1928 lies exactly 20 cm (+/−1 mm) above the bottom end 404 of the open-ended tube 1922. To ensure a reliable measure it is checked that the glass frit 1928 is perfectly horizontal with the help of a bubble level.
2) Any remaining droplets of liquid on top of the glass frit are carefully removed by means of a filter paper of any other suitable material.
3) The sample is weighed with an analytical balance with a resolution of ±0.001 g. The Weight is recorded as Dry Sample Weight ($W_D$) to the nearest 0.001 g when the readings on the balance become constant.
4) 4 sheets of collagen material are carefully aligned on top of each other using tweezers. This stack of 4 sheets of collagen is subsequently referred to as "sample". The sample 1930 is positioned in the center of the sample holder with the help of tweezers with particular care in not altering the orientation and relative position of each of the layers of the acquisition system.
5) The confining weight 1929 is positioned centered on the sample
6) The stopcock 1923 is opened for 30+/−1 seconds allowing liquid to flow in the sample and then closed again.
7) The confining weight 1929 and the sample 1930 are carefully removed from the glass frit 1928 with the help of tweezers.
8) The sample 1930 is weighed with the analytical balance with a resolution of ±0.001 g. The Weight is recorded as 20 cm Sample Weight ($W_{20}$) to the nearest 0.001 g when the readings on the balance become constant.

The measurements of a sample are now completed and a subsequent replicate can be measured repeating the above steps. Once terminated the series of experiment around 1 cm of liquid is added on the Sample Holder funnel 1927 to completely submerge the glass frit 1928. All the stopcocks are closed and the cap positioned according to the storage condition explained above to avoid evaporation and ensure reliability of the subsequent measurements.

Calculations:

The FHFA at 20 cm ($FHFA_{20}$) is defined according to the following formula:

$$FHFA_{20} = (W_{20} - W_D)/W_D \text{ and has unit of g/g.}$$

For measuring the Fixed Height Frit Absorption (FHFA) at 0 cm, for each replicate:

1) The sample holder is positioned on the clamp 1914 such that the top of the glass frit 1928 lies exactly 0 cm (+/−1 mm) above the bottom end 404 of the open-ended tube 1922. To ensure a reliable measure it is checked that the glass frit 1928 is perfectly horizontal with the help of a bubble level.
2) Any remaining droplet of liquid on top of the glass frit are carefully removed by means of a filter paper of any other suitable material.
3) The sample is weighed with an analytical balance with a resolution of ±0.001 g. The Weight is recorded as Dry Sample Weight ($W_D$) to the nearest 0.001 g when the readings on the balance become constant.
4) 4 sheets of collagen material are carefully aligned on top of each other using tweezers. This stack of 4 sheets of collagen is subsequently referred to as "sample". The sample 1930 is positioned in the center of the sample holder with the help of tweezers with particular care in not altering the orientation and relative position of each of the layers of the acquisition system. It is important that the topsheet facing side of each layer is facing now downwards during the experiment in the direction of the glass frit 1928, reproducing the liquid flow entrance direction correctly.
5) The confining weight 1929 is positioned centered on the sample
6) The stopcock 1923 is opened for 30+/−1 seconds allowing liquid to flow in the sample and then closed again.
7) The confining weight 1929 and the sample 1930 are carefully removed from the glass frit 1928 with the help of tweezers.
8) The sample 1930 is weighed with the analytical balance with a resolution of ±0.001 g. The Weight is recorded as 0 cm Sample Weight ($W_0$) to the nearest 0.001 g when the readings on the balance become constant.

The measurements of a sample are now completed and a subsequent replicate can be measured repeating the above steps. Once terminated the series of experiment around 1 cm of liquid is added on the Sample Holder funnel 1927 to completely submerge the glass frit 1928. All the stopcocks are closed and the cap positioned according to the storage condition explained above to avoid evaporation and ensure reliability of the subsequent measurements.

Calculations:

The FHFA at 0 cm ($FHFA_0$) is defined according to the following formula:

$$FHFA_0 = (W_0 - W_D)/W_D \text{ and has unit of g/g.}$$

Accelerated Compression Method

1. Cut 10 samples of the topsheet/acquisition layer laminate 245 (called herein specimen) to be tested and 11 samples of paper towel into a 3 inch×3 inch (7.6 cm×7.6 cm) square.
2. Measure the caliper of each of the 10 specimens at 0.5 kPa and a dwell time of 2 seconds using a Thwing-Albert ProGage Thickness Tester or equivalent with a 50-60 millimeter diameter circular foot. Record the pre-compression caliper to the nearest 0.01 mm
3. Alternate the layers of the specimens to be tested with the paper towels, starting and ending with the paper towels. The choice of paper towel does not matter and is present to prevent "nesting" of the protrusions in the deformed samples. The samples should be oriented so the edges of each of the specimens and each of the paper towels are relatively aligned, and the protrusions in the specimens are all oriented the same direction.
4. Place the stack of samples into a 40° C. oven and place a weight on top of the stack. The weight must be larger than the foot of the thickness tester. To simulate high pressures or low in-bag stack heights, apply 35 kPa (e.g. 17.5 kg weight over a 70×70 mm area). To simulate low pressures or high in-bag stack heights, apply 7 kPa (e.g. 3.5 kg weight over a 70×70 mm area), 4 kPa (e.g., 1.9 kg weight over a 70×70 mm area) or 1 kPa (e.g., 0.49 kg weight over a 70×70 mm area).
5. Leave the samples in the oven for 15 hours. After the time period has elapsed, remove the weight from the samples and remove the samples from the oven.
6. Within 30 minutes of removing the samples from the oven, measure the post-compression caliper as directed in step 2 above, making sure to maintain the same order in which the pre-compression caliper was recorded. Record the post-compression caliper of each of the 10 specimens to the nearest 0.01 mm
7. Let the samples rest at 23±2° C. and at 25±3% relative humidity for 24 hours without any weight on them.
8. After 24 hours, measure the post-recovery caliper of each of the 10 specimens as directed in step 2 above, making sure to maintain the same order in which the pre-compression and post-compression calipers were recorded. Record the post-recovery caliper of each of the 10 specimens to the nearest 0.01 mm Calculate the amount of caliper recovery by subtracting the post-compression caliper from the post-recovery caliper and record to the nearest 0.01 mm.
9. If desired, an average of the 10 specimens can be calculated for the pre-compression, post-compression and post-recovery calipers.

Protrusion Base Width and Protrusion Height Test Methods

1) General Information

The Measured Protrusion Base Width and Measured Protrusion Height of the three-dimensional protrusions of the topsheet or topsheet laminate of an absorbent article are measured using a GFM Primos Optical Profiler instrument commercially available from GFMesstechnik GmbH, Warthestraβe 21, D14513 Teltow/Berlin, Germany. Alternative suitable non-touching surface topology profilers having similar principles of measurement and analysis, can also be used, here GFM Primos is exemplified. The GFM Primos Optical Profiler instrument includes a compact optical measuring sensor based on a digital micro mirror projection, consisting of the following main components:
  a) DMD projector with 800×600 direct digital controlled micro-mirrors
  b) CCD camera with high resolution (640×480 pixels)
  c) Projection optics adapted to a measuring area of at least 30×40 mm
  d) Recording optics adapted to a measuring area of at least 30×40 mm
  e) A table tripod based on a small hard stone plate
  f) A cold light source (an appropriate unit is the KL 1500 LCD, Schott North America, Inc., Southbridge, Mass.)
  g) A measuring, control, and evaluation computer running ODSCAD 6.3 software Turn on the cold-light source. The settings on the cold-light source are set to provide a color temperature of at least 2800K.

Turn on the computer, monitor, and open the image acquisition/analysis software. In the Primos Optical Profiler instrument, select "Start Measurement" icon from the ODSCAD 6.3 task bar and then click the "Live Image button".

The instrument is calibrated according to manufacturer's specifications using calibration plates for lateral (X-Y) and vertical (Z). Such Calibration is performed using a rigid solid plate of any non-shiny material having a length of 11 cm, a width of 8 cm and a height of 1 cm. This plate has a groove or machined channel having a rectangular cross-section, a length of 11 cm, a width of 6.000 mm and an exact depth of 2.940 mm. This groove is parallel to the plate length direction. After calibration, the instrument must be able to measure the width and depth dimensions of the groove to within ±0.004 mm.

All testing is performed in a conditioned room maintained at 23±2° C. and 50+/−10% relative humidity. The surface to be measured may be lightly sprayed with a very fine white powder spray. Preferably, the spray is NORD-TEST Developer U 89, available from Helling GmbH, Heidgraben, Germany.

2) Protrusion Base Width Test Method

The topsheet or topsheet laminate (if more than one layer comprises the protrusion) is extracted from the absorbent article by attaching the absorbent article to a flat surface in a taut planar (i.e. stretched planar) configuration with the topsheet facing up. Any leg or cuff elastics are severed in order to allow the absorbent article to lie flat. Using scissors, two longitudinal cuts are made through all layers above the absorbent core (i.e. the core wrap) along the edges of the topsheet. Two transversal cuts are made through the same layers following the front and back waist edges of the absorbent article.

The topsheet or laminate and any other layers above the absorbent core are then removed without perturbing the topsheet or laminate. Freeze spray (e.g. CRC Freeze Spray manufactured by CRC Industries, Inc. 885 Louis Drive, Warminster, Pa. 18974, USA), or equivalent aid may be used to facilitate removal of the uppermost layers from the absorbent article. The topsheet or laminate is then separated from any other layers, including any carrier layer (e.g. a nonwoven carrier layer, a tissue layer), using freeze spray if necessary. If a distribution layer, e.g. a pulp containing layer is attached to the topsheet or laminate, any residual cellulose fibers are carefully removed with tweezers without modifying the acquisition layer.

The topsheet or laminate with three-dimensional protrusions (conditioned at a temperature of 23° C.±2° C. and a relative humidity of 50%±10% for at least 24 hours) namely "the specimen" is laid down on a hard flat horizontal surface with the body-facing side upward, i.e. the topsheet being upward. Ensure that the specimen is lying in planar configuration, without being stretched, with the specimen uncovered.

A nominal external pressure of 1.86 kPa (0.27 psi) is then applied to the specimen. Such nominal external pressure is applied without interfering with the topology profile measurement. Such an external pressure is applied using a transparent, non-shining flat Plexiglas® plate 200 mm by 70 mm and appropriate thickness (approximately 5 mm) to achieve a weight of 83 g. The plate is gently placed on top of the specimen, such that the center point of the Plexiglas® plate is at least 40 mm away from any folds, with the entire plate resting on the specimen. A fold corresponds to a part of the absorbent article (e.g. the topsheet/acquisition layer laminate) where the absorbent article has been folded for packaging purposes.

Two 50 mm×70 mm metal weights each having a mass of 1200 g (approximate thickness of 43 mm) are gently placed on the Plexiglas® plate such that a 70 mm edge of each metal weight is aligned with the 70 mm edges of the Plexiglas® plate. A metal frame having external dimensions of 70 mm×80 mm and interior dimensions of 42 mm×61 mm, and a total weight of 142 g (approximate thickness 6 mm), is positioned in the center of the Plexiglas® plate between the two end weights with the longest sides of the frame aligned with the longest sides of the plate.

If the specimen is smaller than 70×200 mm, or if a large enough area without a fold is not present, or if an area of interest is close to the edges of the specimen and can't be analyzed with the Plexiglas and weights settings described above, then the X-Y dimensions of the Plexiglas® plate and the added metal weights may be adjusted to reach a nominal external pressure of 1.86 kPa (0.27 psi) while maintaining a minimum 30×40 mm field of view. At least 10 complete three-dimensional protrusions of the specimen should be captured in the field of view of 30 mm×40 mm.

Position the projection head to be normal to the specimen surface (i.e. to the topsheet of the topsheet/acquisition layer laminate).

Adjust the distance between the specimen and the projection head for best focus.

In the Primos Optical Profiler instrument, turn on the button "Pattern" to make a red cross appear on the screen ross and a black cross appears on the specimen.

Adjust the focus control until the black cross is aligned with the red cross on the screen.

Adjust image brightness then capture a digitized image.

In the Primos Optical Profiler instrument, change the aperture on the lens through the hole in the side of the projector head and/or altering the camera "gain" setting on the screen. When the illumination is optimum, the red circle at the bottom of the screen labeled "I.O." will turn green.

Click on the "Measure" button.

The topology of the upper surface of the topsheet/acquisition layer laminate specimen is measured through the Plexiglas plate over the entire field of view 30 mm×40 mm. It is important to keep the specimen still stationary during this time in order to avoid blurring of the captured image. The image should be captured within the 30 seconds following the placement of the Plexiglas plate, metal weights and frame on top of the specimen.

After the image has been captured, the X-Y-Z coordinates of every pixel of the 40 mm×30 mm field of view area are recorded. The X direction is the direction parallel to the longest edge of the rectangular field of view, the Y direction is the direction parallel to the shortest edge of the rectangular field of view. The Z direction is the direction perpendicular to the X-Y plane. The X-Y plane is horizontal while the Z direction is vertical, i.e. orthogonal to the X-Y plane.

These data are smoothed and filtered using a polynomial filter (n=6), a median filter 11 pixels by 11 pixels, and a structure filter 81 pixels by 81 pixels. The polynomial filter (n=6) approximates the X-Y-Z coordinate surface with a polynomial of order 6 and returns the difference to the approximated polynomial. The median filter 11 pixels by 11 pixels divides the field of view (40 mm×30 mm) in X-Y squares of 11 pixels by 11 pixels. The Z coordinate of the pixel located at the center of a given 11 pixels by 11 pixels square will be replaced by the mean Z value of all the pixels of this given square. The structure filter 81 pixels by 81 pixels, removes the waviness of the structure and translates all the Z peak values belonging to the bottom surface of the Plexiglas plate to a top X-Y plane.

A Reference Plane is then defined as the X-Y plane intercepting the surface topology profile of the entire field of view (i.e. 30 mm×40 mm), 100 microns below this top X-Y plane. In the Primos Optical Profiler instrument, to measure the Material Area of the Reference Plane (Z=−0.1 mm), click on the button "Evaluate". Then, apply a pre-filtering routine including a polynomial filter (n=6), a median filter 11 by 11 and a structure filter (n=81) using the function "Filter". Save the image to a computer file with ".omc" extension.

The same above procedure is then executed on the topsheet/acquisition layer laminate with the garment-facing side upward (i.e. the acquisition layer of the topsheet/acquisition layer laminate being upward), the 40 mm×30 mm field of view being located at the exact same X-Y position of the topsheet/acquisition layer laminate.

The Empty Area of the reference plane can be defined as the area of the Reference Plane that is above the surface profile. The Empty Areas having boundaries strictly located inside the field of view area (i.e. 30 mm×40 mm) without crossing or overlapping with the boundaries of the field of view area (i.e. 40 mm×30 mm) are defined as Isolated Empty Area(s). The Measured Protrusion Base Width is defined for an Isolated Empty Area as the diameter of the biggest circle that can be inscribed inside a given Isolated Empty Area. This circle should only overlap with the Isolated Empty Area.

In the Primos Optical Profiler instrument, this can be done by clicking on "Draw circle" and drawing the biggest inscribed circle possible in a chosen Isolated Empty Area. Click on "Show sectional picture", the circle diameter can be measure via clicking on the extremity of the sectional picture profile and then clicking on "Horizontal distance" to obtain the Protrusion Base Width.

For both of the acquired and digitized images, the Protrusion Base Width of all the Isolated Empty Areas is determined. Then, the Measured Protrusion Base Width is calculated as the arithmetic average of the 6 biggest Protrusion Base Widths.

3) Protrusion Height Test Method

The topsheet or laminate is extracted from the absorbent article as described above in the Protrusion Base Width Test Method.

The topsheet or laminate specimen comprising three-dimensional protrusions is then conditioned and scanned under a pressure of 1.86 kPa (0.27 psi) with the body-facing side upward, i.e. the topsheet being upward as described above in the Protrusion Base Width Test Method.

After the image has been captured, the X-Y-Z coordinates of every pixel of the 40 mm×30 mm field of view area are recorded and smoothed/filtered as described above in the Protrusion Base Width Test Method. A reference plane is also defined as described above in the Protrusion Base Width Test Method.

In the Primos Optical Profiler instrument, to measure the Material Area of the Reference Plane (Z=−0.1 mm), click on the button "Evaluate". Then apply a pre-filtering routine including a polynomial filter (n=6), a median filter 11 by 11 and a structure filter (n=81) using the function "Filter". Save the image to a computer file with ".omc" extension.

The same above procedure set out in the Protrusion Base Width Test Method is then executed on the topsheet or laminate with the garment-facing side upward (i.e. the underside of the topsheet or underside of the laminate being upward), the 40 mm×30 mm field of view being located at the exact same X-Y position of the topsheetor laminate.

The Empty Area of the reference plane can be defined as the area of the Reference Plane that is above the surface profile. The Empty Area having boundaries strictly located inside the field of view area (i.e. 30 mm×40 mm) without crossing or overlapping with the boundaries of the field of view area (i.e. 40 mm×30 mm) are defined as Isolated Empty Area(s). The Protrusion Height is defined for an Isolated Empty Area as the distance between the minimum Z value of the points of the topsheet/acquisition layer laminate surface profile having X-Y coordinates located in this Isolated Empty Area, and the Z value of the top X-Y plane.

Click on "Draw N parallel lines" and draw a first segment parallel to the X axis of the field of view (direction of the longest dimension of the field of view) passing through the center of the Isolated Empty Area and extending outside the Isolated Empty Area boundaries. The center of the Isolated Empty Area corresponds to the middle of the segment parallel to the Y axis of the field of view and joining the biggest and smallest Y value of the Isolated Empty Area. Then input the "number" of lines to be drawn and set the "distance" between lines to 0.05 mm Enough lines need to be drawn such to cover the entire Isolated Empty Area. Leave the averaging parameter to 0 then click "Ok". Then click on "Show sectional picture". Click on the point of the sectional picture profile having the minimum Z value and click on "Vertical distance" to obtain the Protrusion Height.

For both of the acquired and digitized images, the Protrusion Height of all the Isolated Empty Areas is determined. Then, the Measured Protrusion Height is calculated as the arithmetic average of the 6 biggest Protrusion Heights.

Measurements of the maximum interior width of the void area at the distal portion can be made on a photomicrograph at 20× magnification.

Tensile Method

The MD and CD tensile properties are measured using World Strategic Partners (WSP) (harmonization of the two nonwovens organizations of INDA (North American based) and EDANA (Europe based)) Tensile Method 110.4 (05) Option B, with a 50 mm sample width, 60 mm gauge length, and 60 mm/min rate of extension. Note that the gauge length, rate of extension and resultant strain rate are from different from that specified within the method.

Contact Angle Method

Contact angles on substrates are determined using ASTM D7490-13 modified with the specifics as describe herein, using a goniometer and appropriate image analysis software (a suitable instrument is the FTA200, First Ten Angstroms, Portsmouth, Va., or equivalent) fitted with a 1 mL capacity, gas tight syringe with a No. 27 blunt tipped stainless steel needle. One test fluid is used: Type II reagent water (distilled) in accordance with ASTM Specification D1193-99. All testing is to be performed at about 23° C.±2 C.° and a relative humidity of about 50%±2%.

A 50 mm by 50 mm specimen to be tested is removed from the topsheet of the article being tested taking care to not touch the region of interest or otherwise contaminate the surface during harvesting or subsequent analysis. Condition the samples at about 23° C.±2 C.° and a relative humidity of about 50%±2% for 2 hours prior to testing.

Set up the goniometer on a vibration-isolation table and level the stage according to the manufacturer's instructions. The video capture device must have an acquisition speed capable of capturing at least 10-20 images from the time the drop hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the sample. In the case of slow acquisition, the images should be acquired until 2% of the volume of the drop is absorbed into the specimen. If the acquisition is extremely fast, the first resolved image should be used if the second image shows more than 2% volume loss.

Place the specimen on the goniometer's stage and adjust the hypodermic needle to the distance from the surface recommended by the instrument's manufacturer (typically 3 mm). If necessary adjust the position of the specimen to place the target site under the needle tip. Focus the video device such that a sharp image of the drop on the surface of the specimen can be captured. Start the image acquisition. Deposit a 5 µL±0.1 µL drop onto the specimen. If there is visible distortion of the drop shape due to movement, repeat at a different, but equivalent, target location. Make two angle measurements on the drop (one on each drop edge) from the image at which there is a 2% drop volume loss. If the contact angles on two edges are different by more than 4°, the values should be excluded and the test repeated at an equivalent location on the specimen. Identify five additional equivalent sites on the specimen and repeat for a total of 6 measurements (12 angles). Calculate the arithmetic mean for this side of the specimen and report to the nearest 0.01°. In like fashion, measure the contact angle on the opposite side of the specimen for 6 drops (12 angles) and report separately to the nearest 0.01°.

For any sites which demonstrate an arithmetic mean which is higher or lower than another arithmetic mean—by at least 2 times the highest standard deviation the angle measurements comprised by the two arithmetic means—an equivalent site on a specimen from another article shall be measured in accordance to the SEM Method for determining contact angle on fibers. Any such sites shall be termed "area of interest."

Moreover, when an area of interest of the specimen is on a distal end and/or sidewall of a protrusion, the contact angle measurements with regard to the distal end and/or sidewall shall be performed in accordance with the SEM Method for determining contact angle on fibers described herein.

SEM Method for Determining Contact Angle on Fibers

A rectangular specimen measuring 1 cm×2 cm is cut from the topsheet of a disposable absorbent product taking care not to touch the surface of the specimen or to disturb the structure of the material. The specimen shall include the area of interest determined in the Contact Angle Method heretofore described. If multiple areas of interest are identified then additional specimens shall be obtained in accordance with this method to accommodate all areas of interest identified. The specimen has a length of (2 cm) aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby airbrush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. This is further discussed with regard to FIGS. 37-40. The contact angle between the droplet and the fiber is determined directly from the images taken as is shown via lines 3700A, 3700B, 3800A, 3800B, 3900A, 3900B, 4000A, and 4000B. Twenty separate droplets are imaged from which forty contact angle measurements are performed (one on each side of each imaged droplet), and the arithmetic average of these forty contact angle measurements is calculated and reported as the contact angle for that specimen.

Figure 37A:
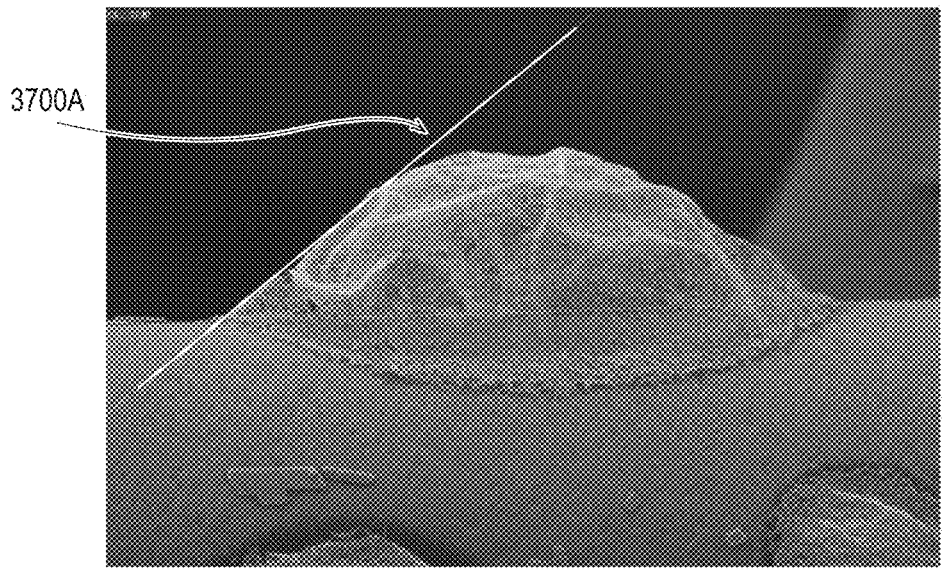
FIGS. 37A-40B are photomicrographs depicting exemplary water droplets on fibers for the SEM contact angle measurement method disclosed herein.
Figure 37B:
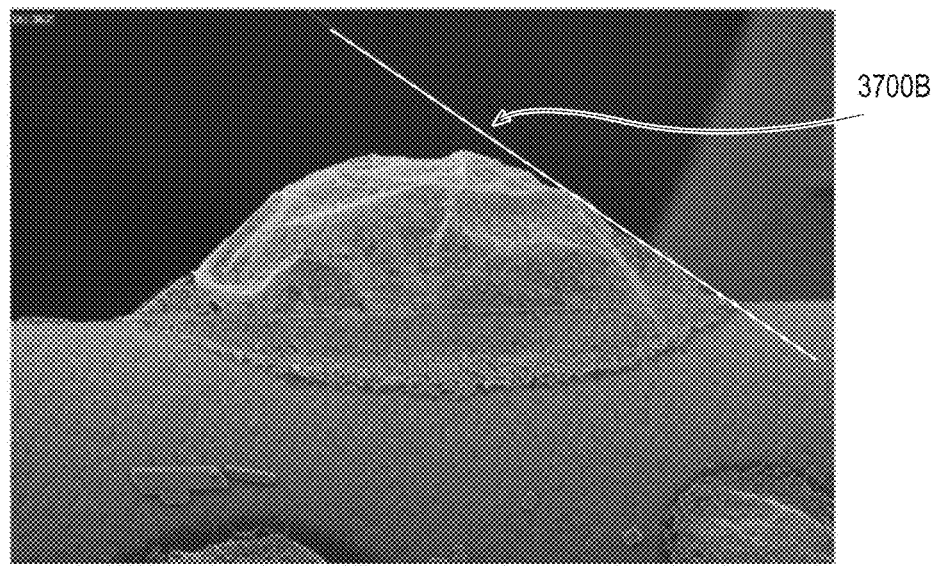
Figure 38A:
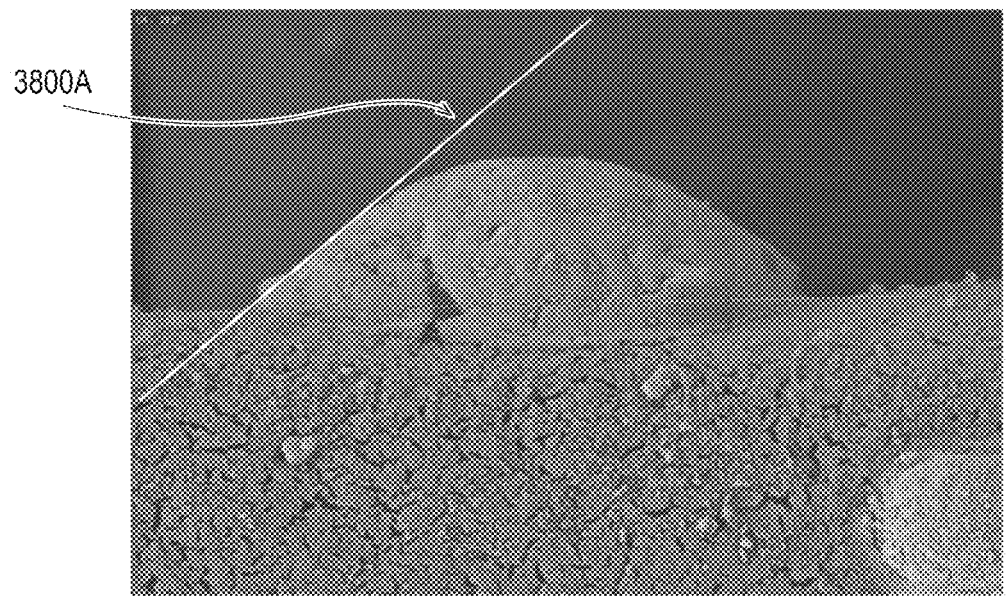
Figure 38B:
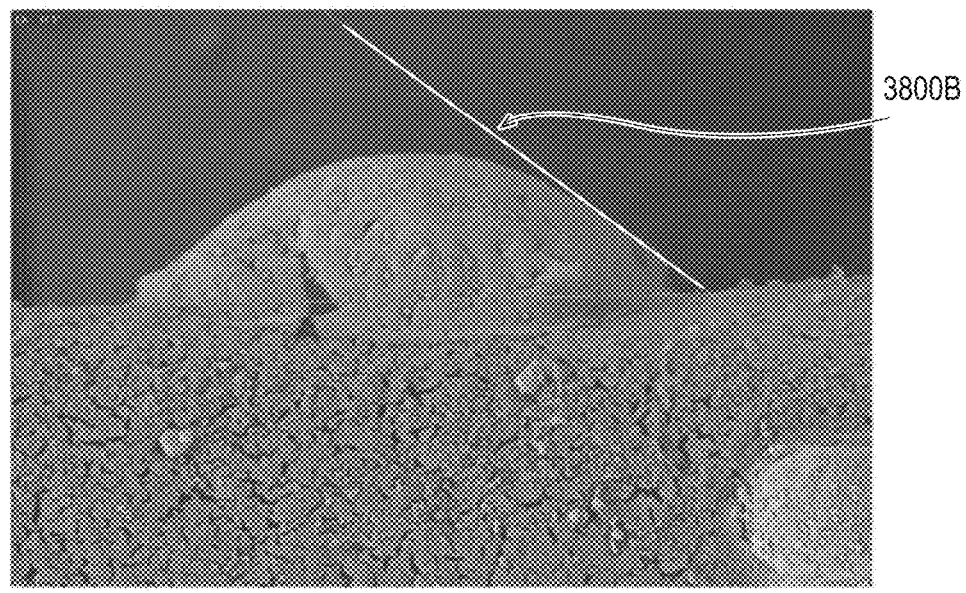
Figure 39A:
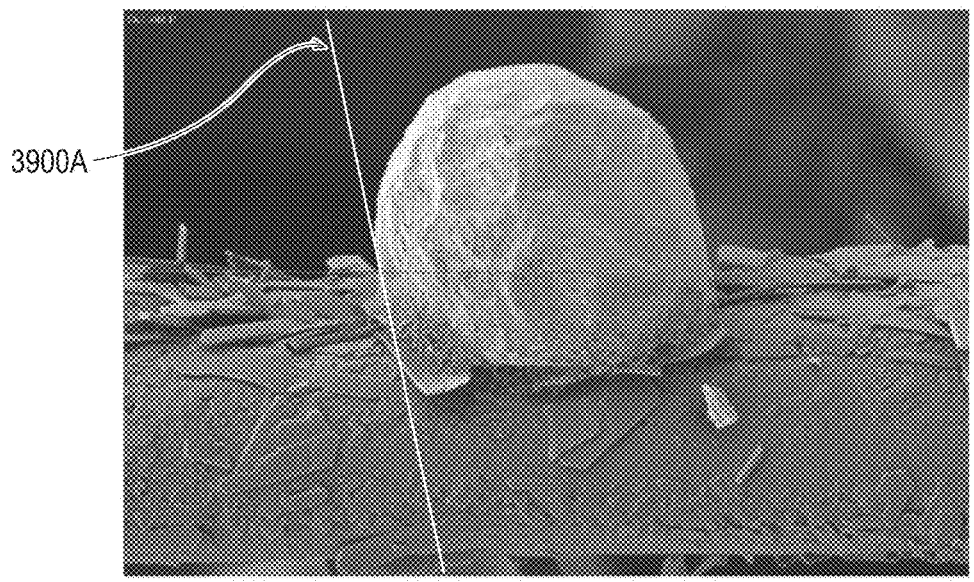
Figure 39B:
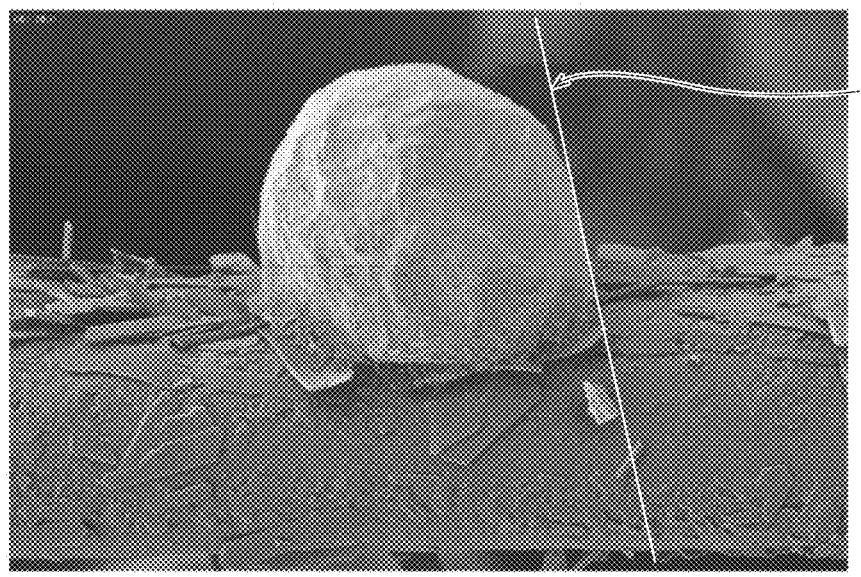
Figure 40A:
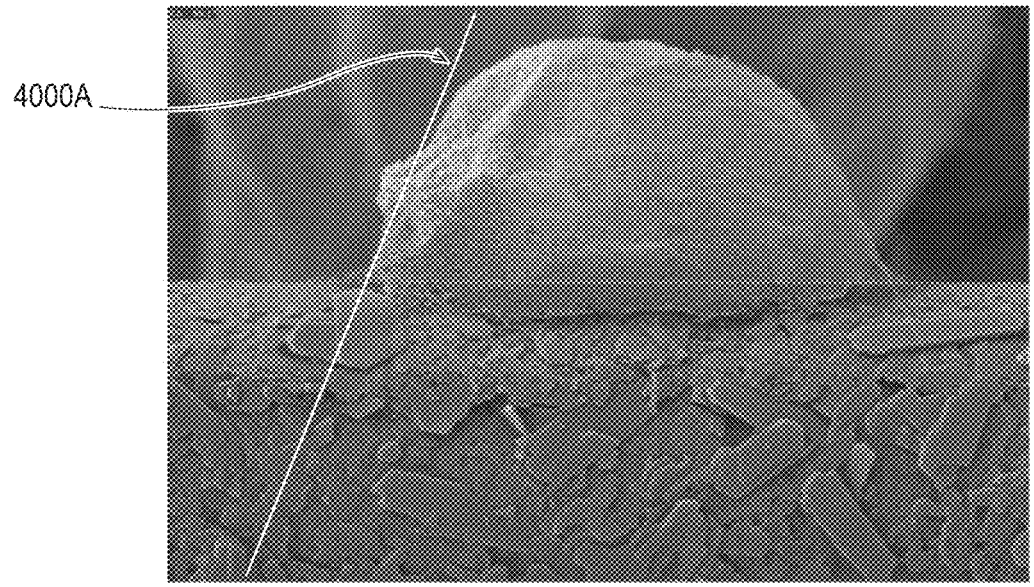
Figure 40B:
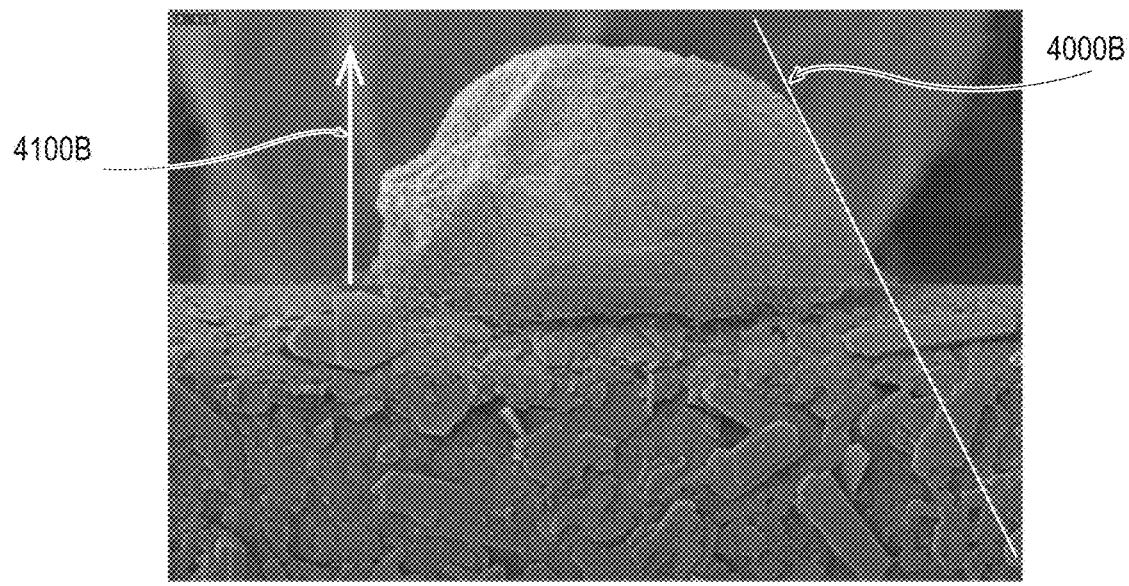

Examples of images are provided with regard to FIGS. 37-40. FIGS. 37 and 38 are exemplary images depicting water droplets cryogenically frozen on fibers upon which no composition has been applied. FIGS. 39 and 40 are exemplary images depicting water droplets cryogenically frozen on fibers upon which composition has been applied. As noted previously, the projection of the droplet should be maximized to ensure that the appropriate contact angle is measured. An exemplary droplet projection 4100B is shown in FIG. 40B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A textured nonwoven web having a plurality of fibers, a generally planar first region and a plurality of discrete integral second regions, the generally planar first region comprising a first and a second surface, the plurality of discrete integral second regions comprising protrusions extending outward from the first surface of said nonwoven material and openings in the second surface of the nonwoven material, said protrusions being formed from said fibers, wherein the protrusions comprise a base proximate the first surface of said nonwoven material, an opposed distal end extending outward from the base, sidewalls between said base and said distal end of said protrusion, and a cap comprising at least a portion of the sidewalls and the distal end of the protrusions, wherein each of said sidewalls and distal ends have inner surfaces and opposed outer surfaces, wherein multiple fibers extend from the base of the protrusions to the distal end of the protrusions, and contribute to form a portion of the sides and cap of a protrusion, and said fibers at least substantially surround the sides of the protrusions, wherein the inner surfaces of the sidewalls define a base opening at the base of the protrusion, and wherein a first composition is disposed on the textured nonwoven web in the first region and/or a portion of the plurality of discrete integral second regions, wherein the first composition is more hydrophilic than the plurality of fibers as measured by the SEM Method for determining contact angle on fibers and is disposed on at least a portion of the plurality of discrete integral second regions, and wherein the protrusions extend in a negative Z-direction.

2. The textured nonwoven web of claim 1, wherein the first composition is disposed on the inner surface of the distal ends and/or the inner surface of the sidewalls.

3. The textured nonwoven web of claim 1, wherein the plurality of fibers are more hydrophobic than the first composition as measured by the SEM Method for determining contact angle on fibers.

4. The textured nonwoven web of claim 1, wherein the first composition is disposed in the first region.

5. The textured nonwoven web of claim 4, wherein the first composition is more hydrophobic than the plurality of fibers as measured by the SEM Method for determining contact angle on fibers.

6. The textured nonwoven web of claim 1, further comprising a second composition disposed on the second surface.

7. The textured nonwoven web of claim 6, wherein the second composition is more hydrophobic than the first composition as measured by the SEM Method for determining contact angle of fibers.

8. The textured nonwoven web of claim 1, wherein the textured nonwoven web forms a portion of a disposable absorbent article, the disposable absorbent article comprising a wearer-facing surface and a garment-facing surface, wherein the textured nonwoven web forms a portion of the wearer-facing surface.

9. The textured nonwoven web of claim 8, wherein the disposable absorbent article further comprises an absorbent core, and an acquisition layer, wherein each of the protrusions comprises a primary protrusion and a secondary protrusion and wherein the acquisition layer forms the primary protrusion, and wherein the distal ends of the protrusions are oriented toward the absorbent core.

10. The textured nonwoven web of claim 9, wherein the disposable absorbent article exhibits a post acquisition collagen rewet of less than 260 mg in accordance with the Post Acquisition collagen Rewet test.

11. The textured nonwoven web of claim 9, wherein a width of the acquisition layer in a direction parallel to a lateral axis is less than a width of a topsheet in a direction parallel to the lateral axis.

12. The textured nonwoven web of claim 1, wherein the plurality of fibers comprise natural and synthetic fibers, and wherein the natural and synthetic fibers are hydrophobic.

13. The textured nonwoven web of claim 1, wherein the first composition is disposed on the outer surface of the distal ends and/or outer surface of the sidewalls.

14. A textured nonwoven web having a plurality of fibers, a generally planar first region and a plurality of discrete integral second regions, the generally planar first region comprising a first and a second surface, the plurality of discrete integral second regions comprising protrusions extending outward from the first surface of said nonwoven material and openings in the second surface of the nonwoven material, said protrusions being formed from said fibers, wherein the protrusions comprise a base proximate the first surface of said nonwoven material, an opposed distal end extending outward from the base, sidewalls between said base and said distal end of said protrusion, and a cap comprising at least a portion of the sidewalls and the distal end of the protrusions, wherein each of said sidewalls and distal ends have inner surfaces and opposed outer surfaces, wherein multiple fibers extend from the base of the protrusions to the distal end of the protrusions, and contribute to form a portion of the sides and cap of a protrusion, and said fibers at least substantially surround the sides of the protrusions, wherein the inner surfaces of the sidewalls define a base opening at the base of the protrusion, and wherein a first composition is disposed on the textured nonwoven web in the first region and/or a portion of the plurality of discrete integral second regions, wherein the first composition is more hydrophobic than the plurality of fibers and is disposed on at least a portion of the plurality of discrete integral second regions, and wherein the protrusions extend in a positive Z-direction, and wherein the textured nonwoven web further comprises a second composition disposed on the first surface in the first region.

15. The textured nonwoven web of claim 14, wherein the second composition is more hydrophilic than the first composition as measured by the SEM Method for determining contact angle on fibers.

16. The textured nonwoven web of claim 14, wherein the first composition is disposed on the outer surface of the distal ends and/or outer surface of the sidewalls.

17. A textured nonwoven web comprising a plurality of natural and synthetic fibers, wherein the natural and synthetic fibers are hydrophobic, a generally planar first region and a plurality of discrete integral second regions, the generally planar first region comprising a first and a second surface, the plurality of discrete integral second regions comprising protrusions extending outward from the first surface of the nonwoven material and openings in the second surface of the nonwoven material, the protrusions comprising the natural and synthetic fibers, wherein the protrusions comprise a base proximate the first surface of the nonwoven material, an opposed distal end extending outward from the base, sidewalls between the base and the distal end of the protrusion, and a cap comprising at least a portion of the sidewalls and the distal end of the protrusions, wherein each of the sidewalls and distal ends have inner surfaces and opposed outer surfaces, wherein the natural and synthetic fibers extend from the base of the protrusions to the distal end of the protrusions, and contribute to form a portion of the sides and cap of a protrusion, and the natural and synthetic fibers at least substantially surround the sides of the protrusions, wherein the inner surfaces of the sidewalls define a base opening at the base of the protrusion, wherein a first composition is disposed on the textured nonwoven web in the first region and/or a portion of the plurality of discrete integral second regions, wherein the first composition is more hydrophilic than the natural and synthetic fibers as measured by the SEM Method for determining contact angle on fibers and is disposed on at least a portion of the plurality of discrete integral second regions, and wherein the protrusions extend in a negative Z-direction.

18. The textured nonwoven web of claim 17, wherein the first composition is disposed on the inner surface of the distal ends and/or the inner surface of the sidewalls.

19. The textured nonwoven web of claim 17, wherein the first composition is disposed in the first region.

20. The textured nonwoven web of claim 17, wherein the first composition is disposed on the outer surface of the distal ends and/or outer surface of the sidewalls.

* * * * *